United States Patent [19]
Kriesel et al.

[11] Patent Number: 6,068,613
[45] Date of Patent: *May 30, 2000

[54] FLUID DELIVERY DEVICE

[76] Inventors: Marshall S. Kriesel, 80 N. Mississippi Rd., Saint Paul, Minn. 55104; Farhad Kazemzadeh, 9116 Vincent Ave., S., Bloomington, Minn. 55431; Matthew B. Kriesel, 80 N. Mississippi Rd., St. Paul, Minn. 55104; William W. Feng, 948 Kelley Ct., Lafayette, Calif. 94549; Steve C. Barber, 24395 Wood Dr., Shorewood, Minn. 55331; William J. Kluck, 664 Edie La., Hudson, Wis. 54016

[*] Notice: This patent is subject to a terminal disclaimer.

[21] Appl. No.: 08/991,928

[22] Filed: Dec. 16, 1997

Related U.S. Application Data

[60] Division of application No. 08/540,914, Oct. 11, 1995, Pat. No. 5,716,343, which is a continuation-in-part of application No. 08/451,520, May 26, 1995, Pat. No. 5,656,032, which is a continuation-in-part of application No. 08/129,693, Sep. 29, 1993, Pat. No. 5,419,771, which is a continuation-in-part of application No. 08/069,937, May 28, 1993, Pat. No. 5,336,188, which is a continuation-in-part of application No. 08/046,438, May 18, 1993, Pat. No. 5,411,480, which is a continuation-in-part of application No. 07/987,021, Dec. 7, 1992, Pat. No. 5,279,558, which is a continuation-in-part of application No. 07/879,269, Apr. 17, 1992, Pat. No. 5,205,820, which is a continuation-in-part of application No. 07/642,208, Jan. 16, 1991, Pat. No. 5,169,389, which is a continuation-in-part of application No. 07/367,304, Jun. 16, 1989, Pat. No. 5,019,047.

[51] Int. Cl.$^7$ .................................................. A61M 37/00
[52] U.S. Cl. ............................................. 604/132; 604/246
[58] Field of Search .................................. 604/82, 83, 86, 604/131, 132, 151, 153, 890.1

[56] References Cited

U.S. PATENT DOCUMENTS

| 5,167,631 | 12/1992 | Thompson et al. | 604/132 |
| 5,176,641 | 1/1993 | Idriss . | |
| 5,267,957 | 12/1993 | Kriesel et al. | 604/85 |
| 5,336,188 | 8/1994 | Kriesel | 604/132 |
| 5,368,570 | 11/1994 | Thompson et al. | 604/131 |
| 5,484,410 | 1/1996 | Kriesel et al. . | |
| 5,735,818 | 4/1998 | Kriesel et al. | 604/132 |
| 5,885,250 | 3/1999 | Kriesel et al. | 604/132 |

Primary Examiner—Ronald Stright, Jr.
Assistant Examiner—Jeremy Thissell
Attorney, Agent, or Firm—James E. Brunton

[57] ABSTRACT

An apparatus for accurately infusing fluids into a patient at specific rates over an extended period of time. The apparatus is of a low profile, laminate construction having a stored energy source in the form of a distendable membrane, which in cooperation with the base of the apparatus defines one or more fluid reservoirs each having a fluid inlet and a fluid outlet. The apparatus further includes a novel, conformable ullage made of formable materials. The conformable ullage uniquely conforms to the shape of elastomeric membrane as the membrane returns to its less distend configuration and in so doing can move between a central chamber and a toroidal chamber formed in the cover of the apparatus. This arrangement will satisfy even the most stringent medicament delivery tolerance requirements and will elegantly overcome the limitations of materials selection encountered in devices embodying solely rigid ullage construction. Additionally, the infusion cannula of the apparatus is connected to the base in a novel manner which permits expeditious subdermal delivery to the patient via a cannula which extends generally perpendicularly relative to the base.

7 Claims, 50 Drawing Sheets

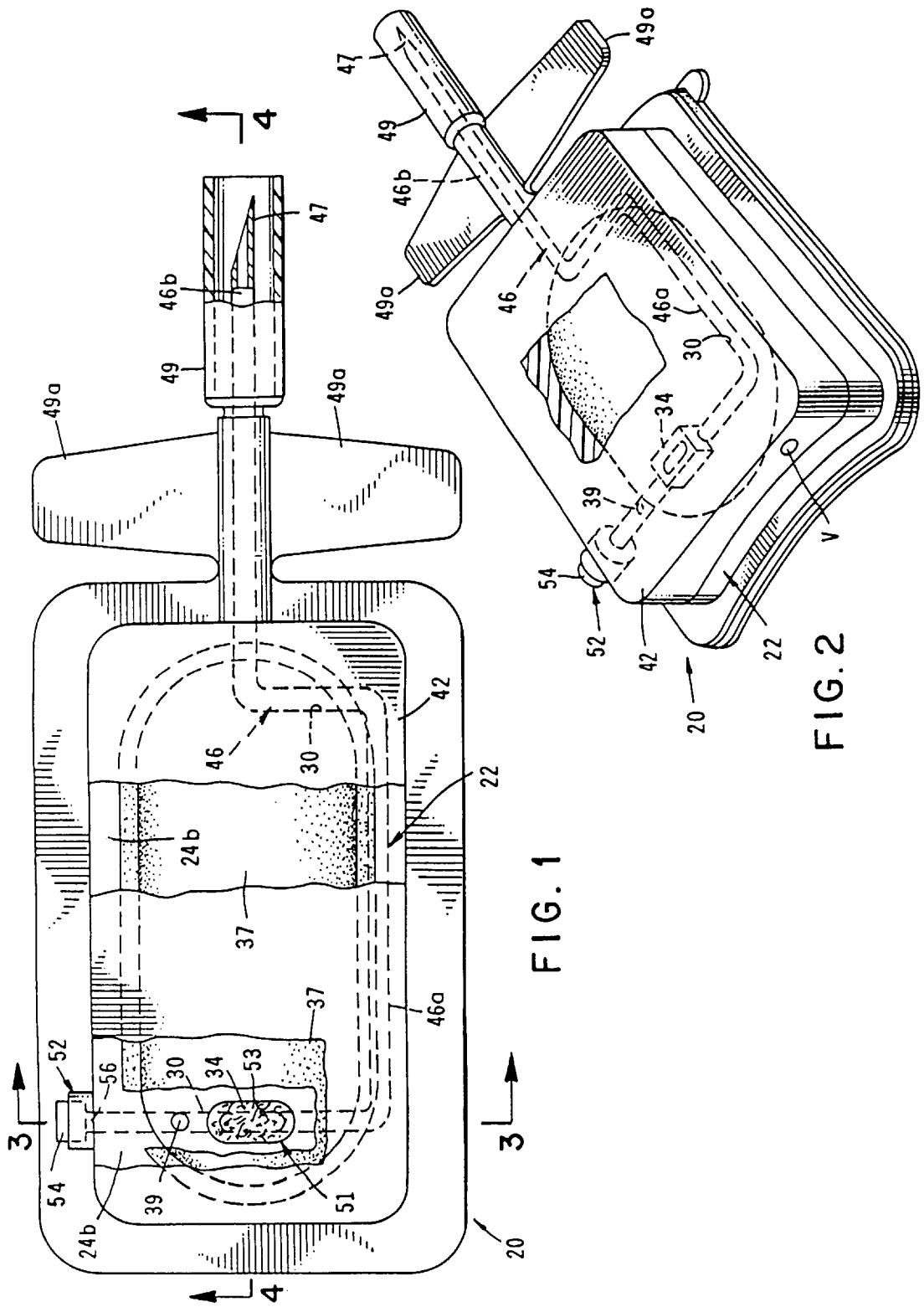

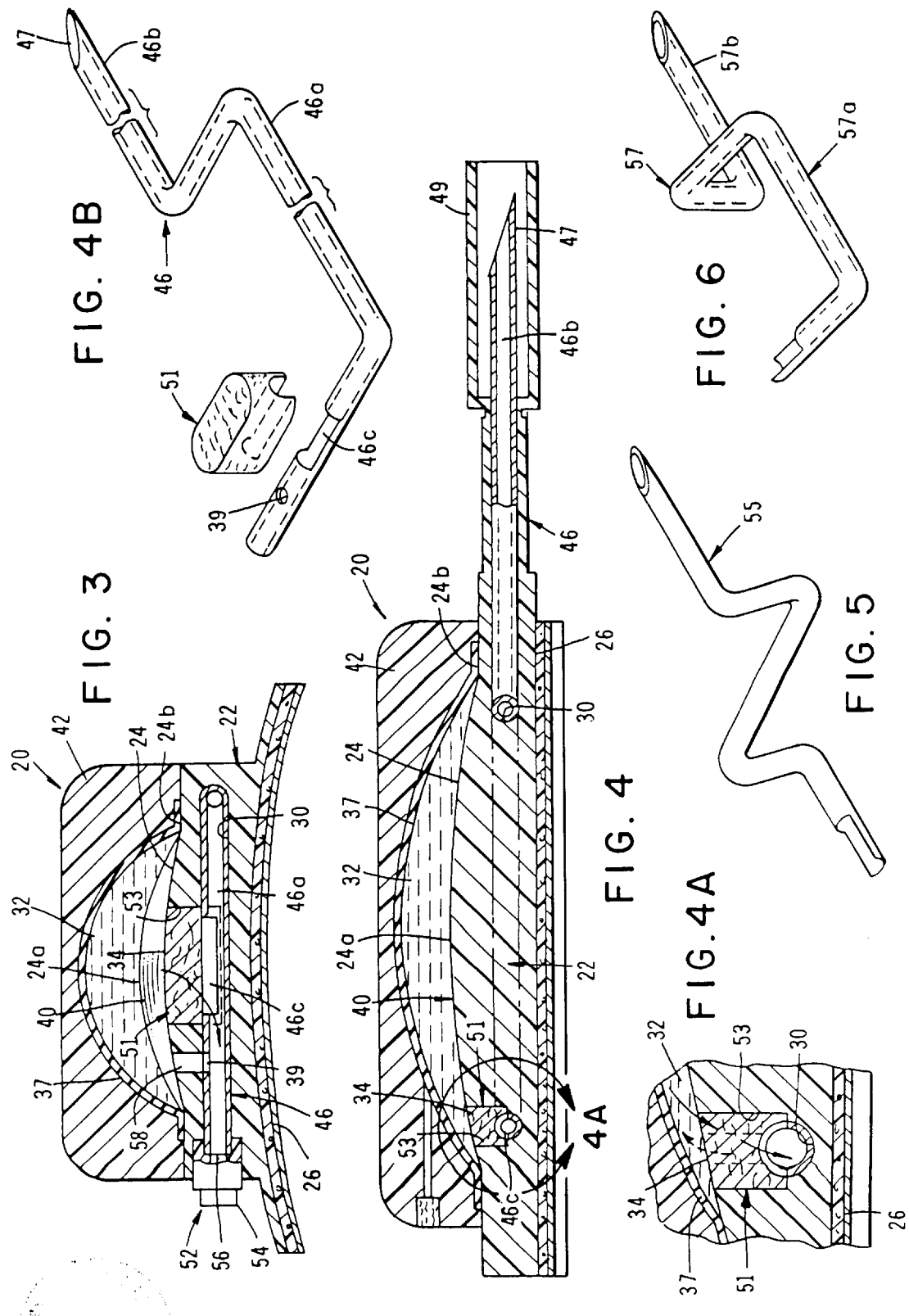

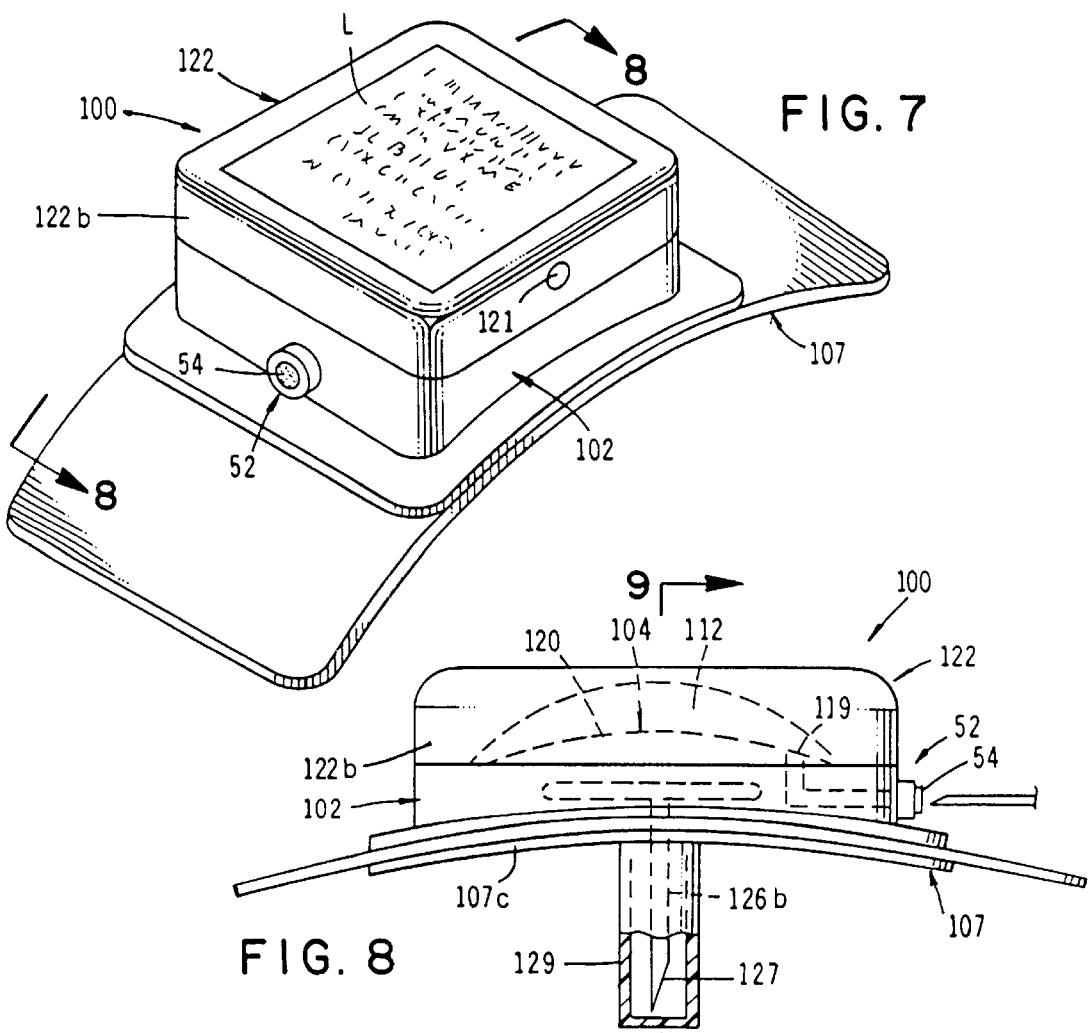
FIG. 7
FIG. 8
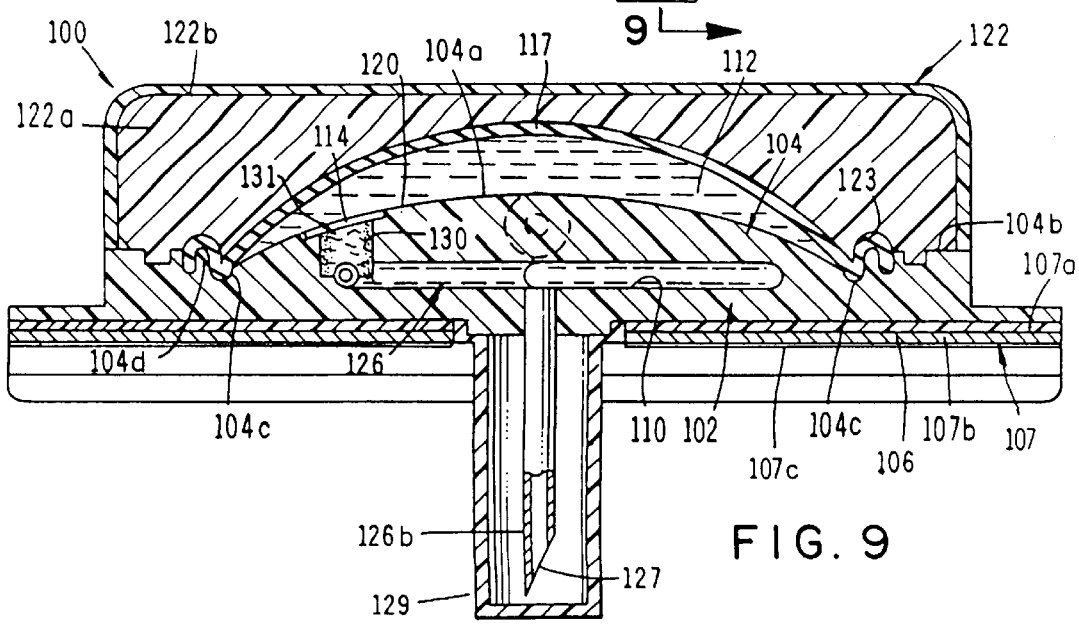
FIG. 9

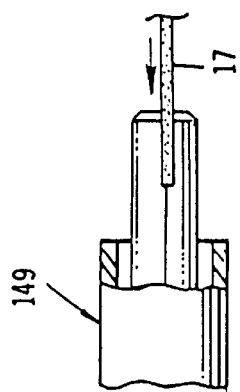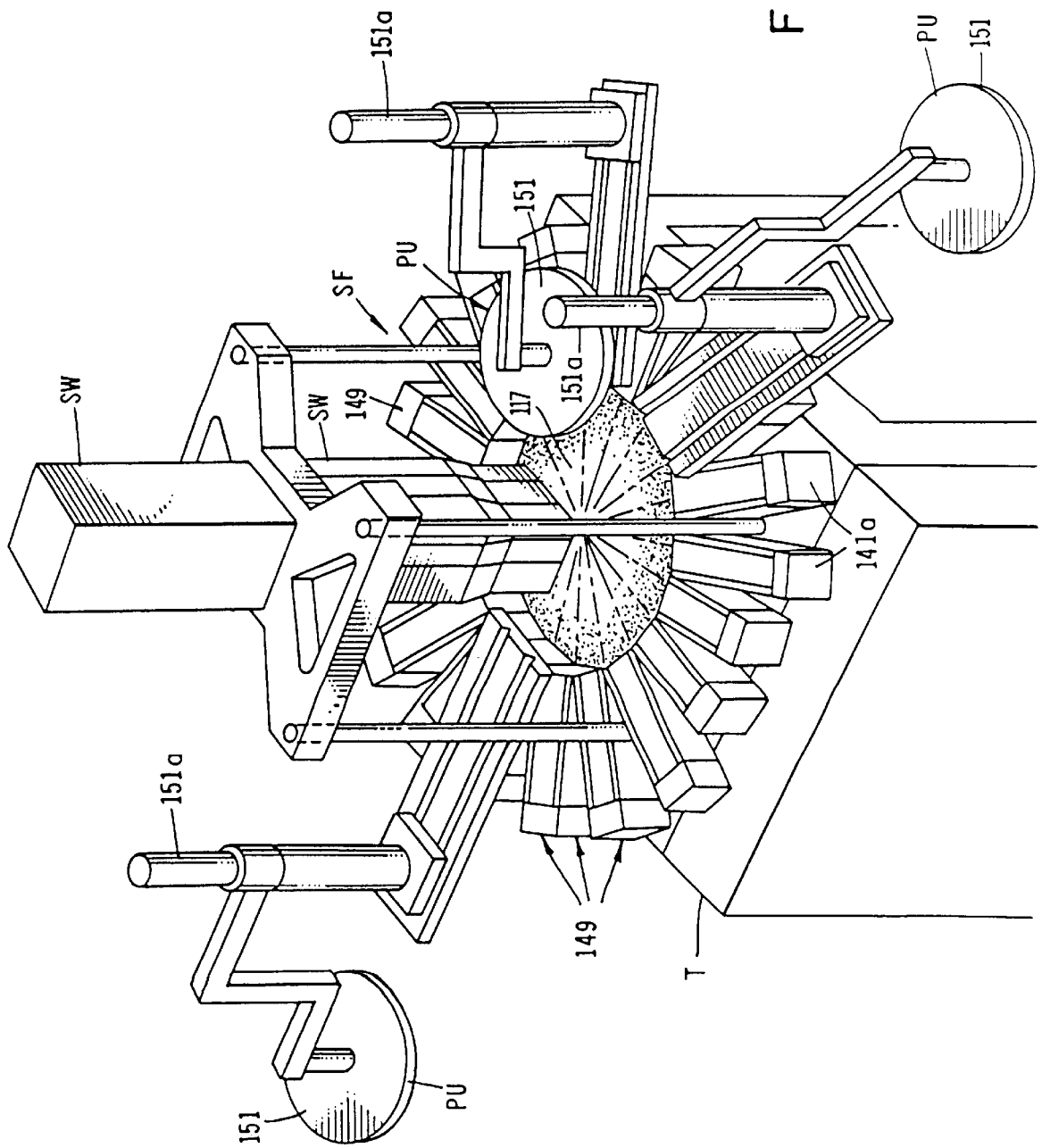

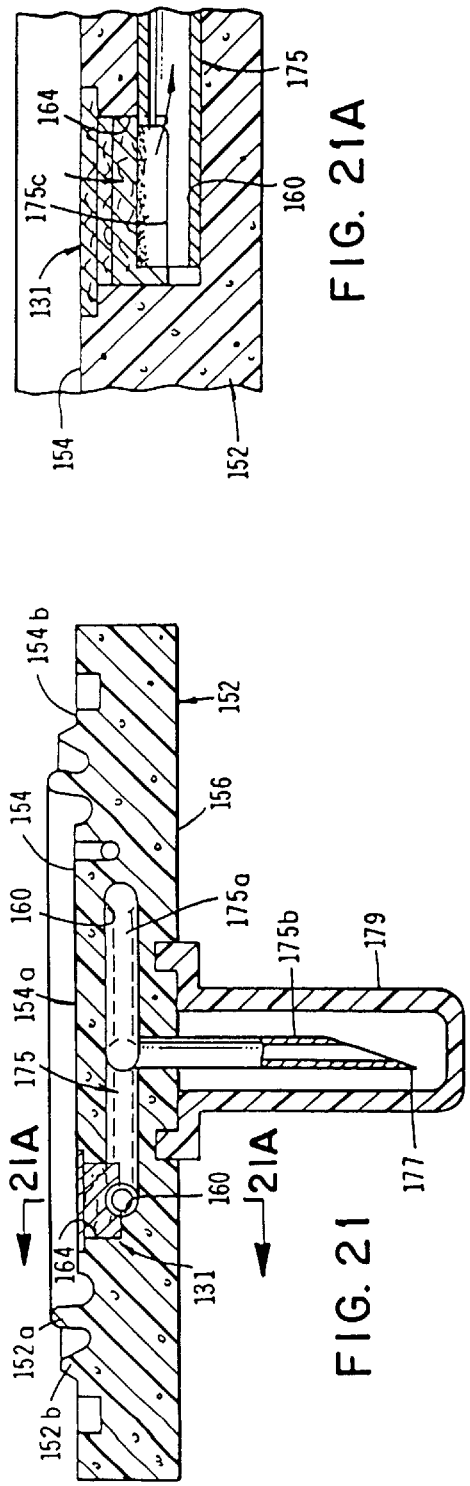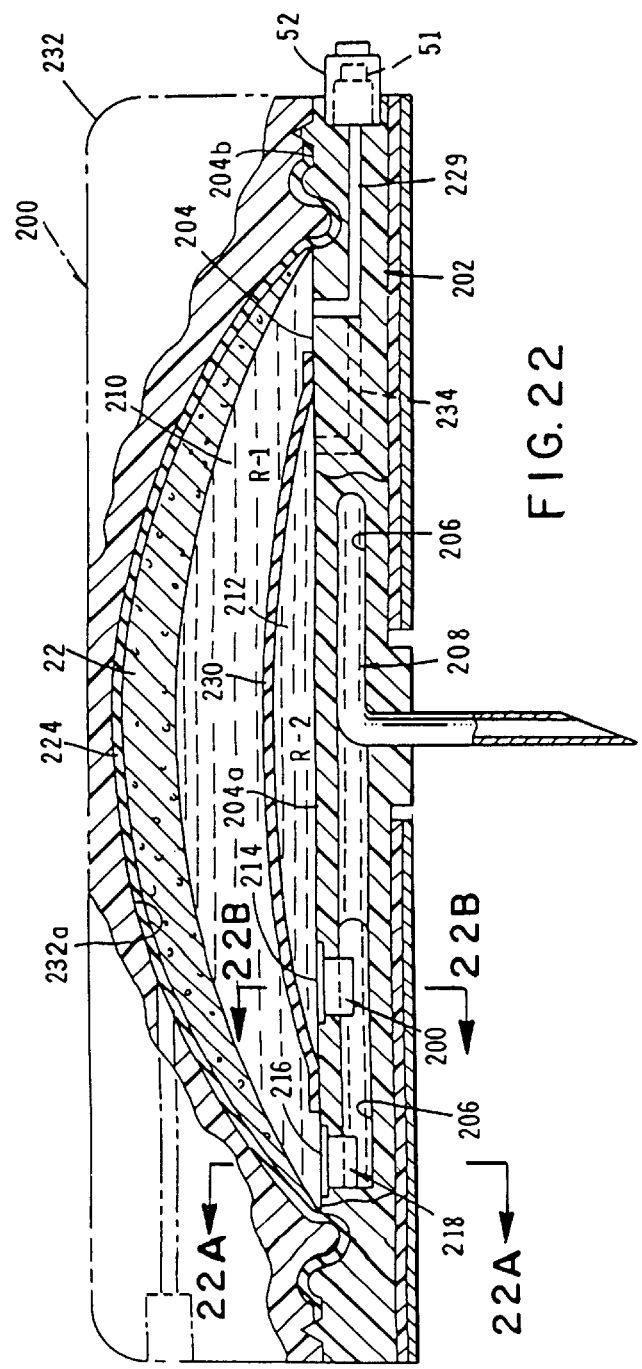

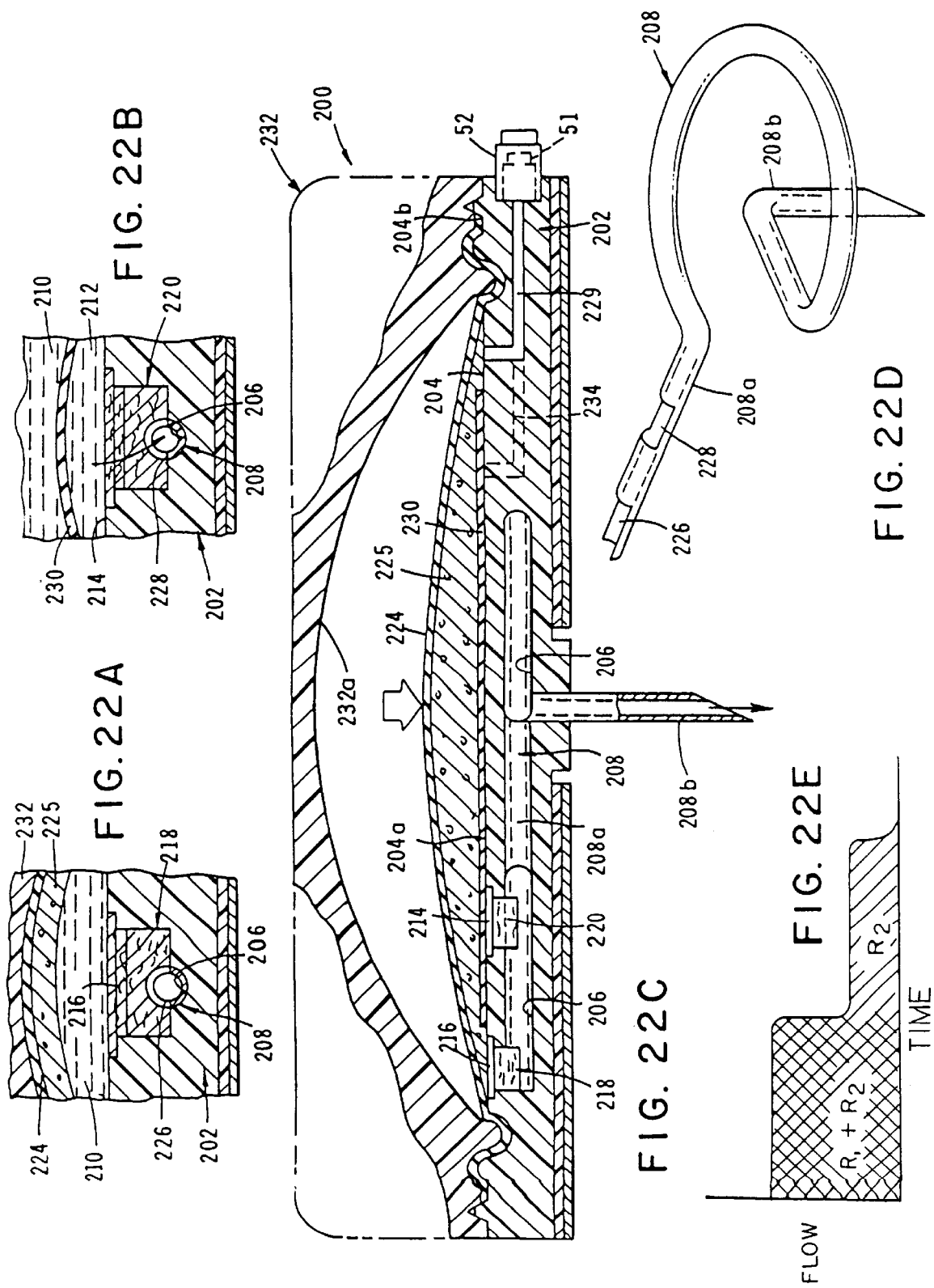

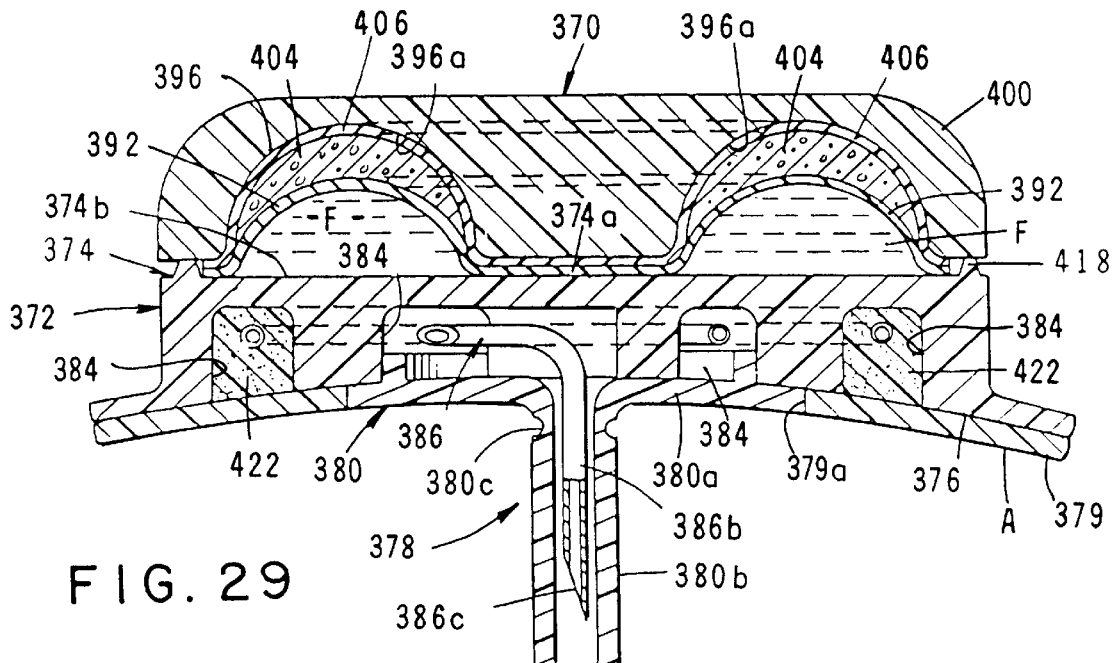
FIG. 29
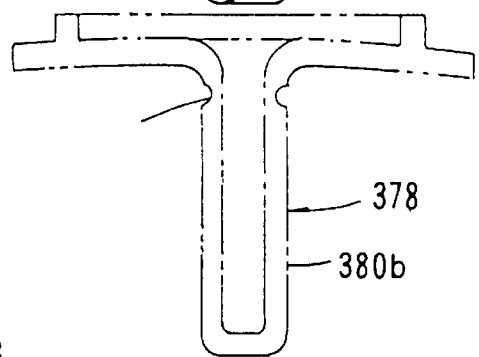
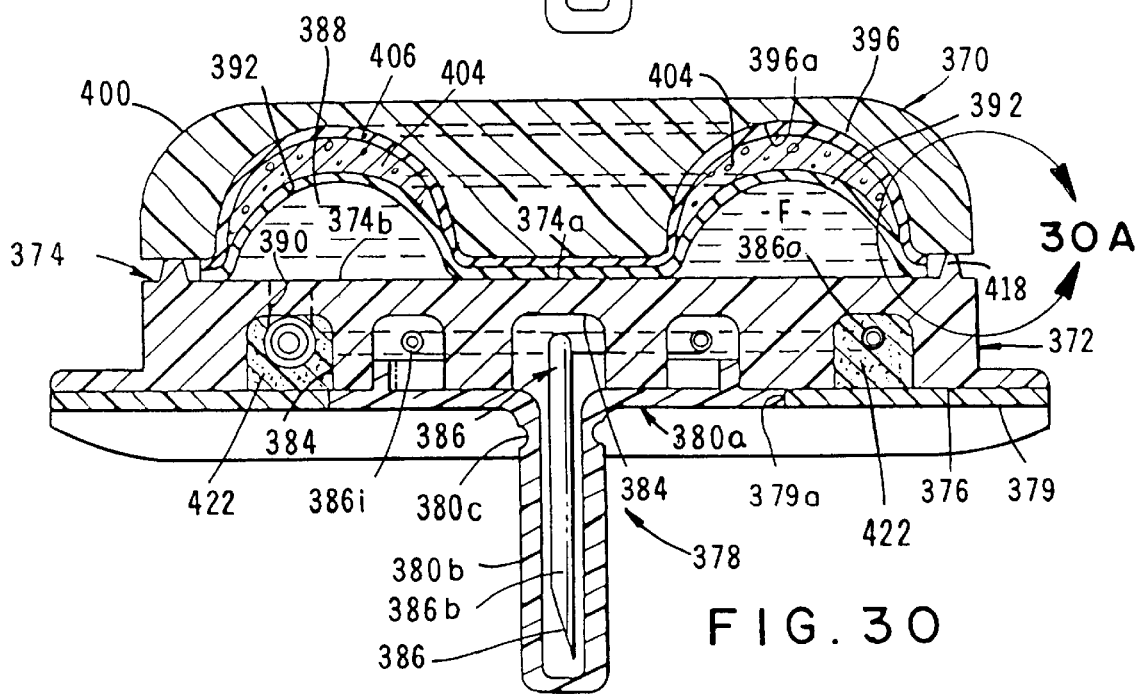
FIG. 30

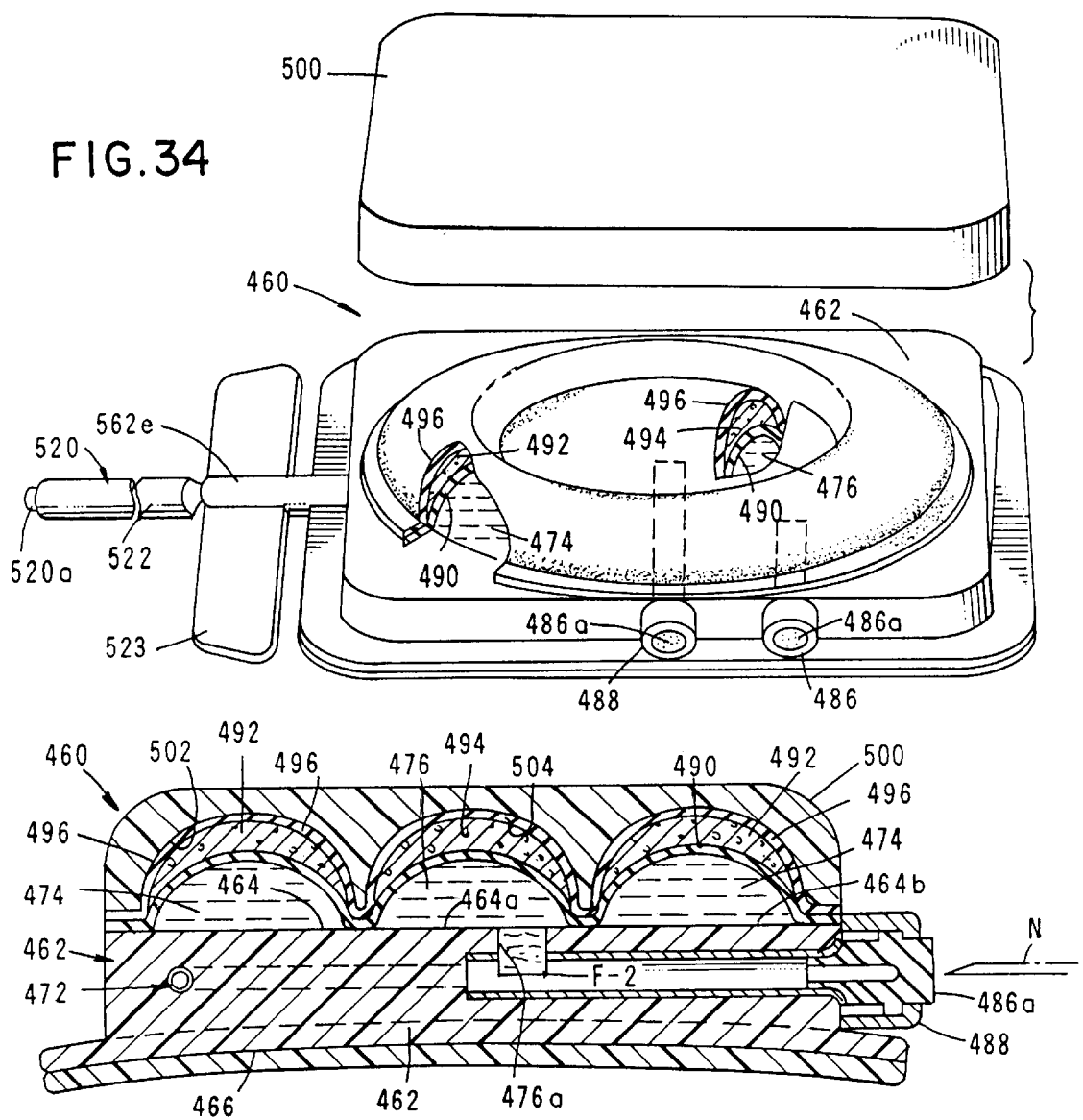
FIG. 34
FIG. 36
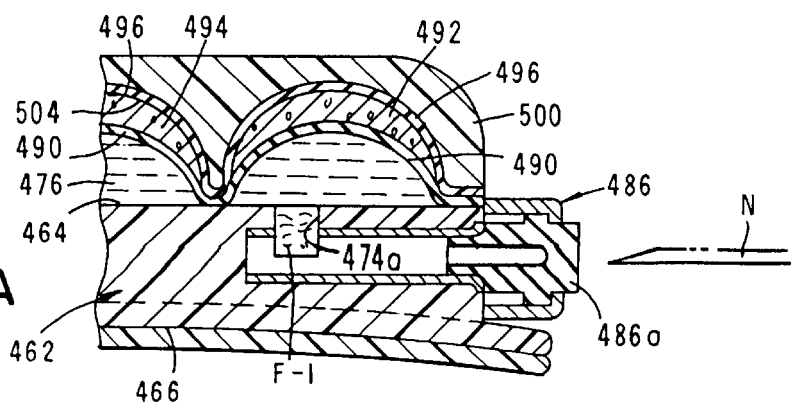
FIG. 36A

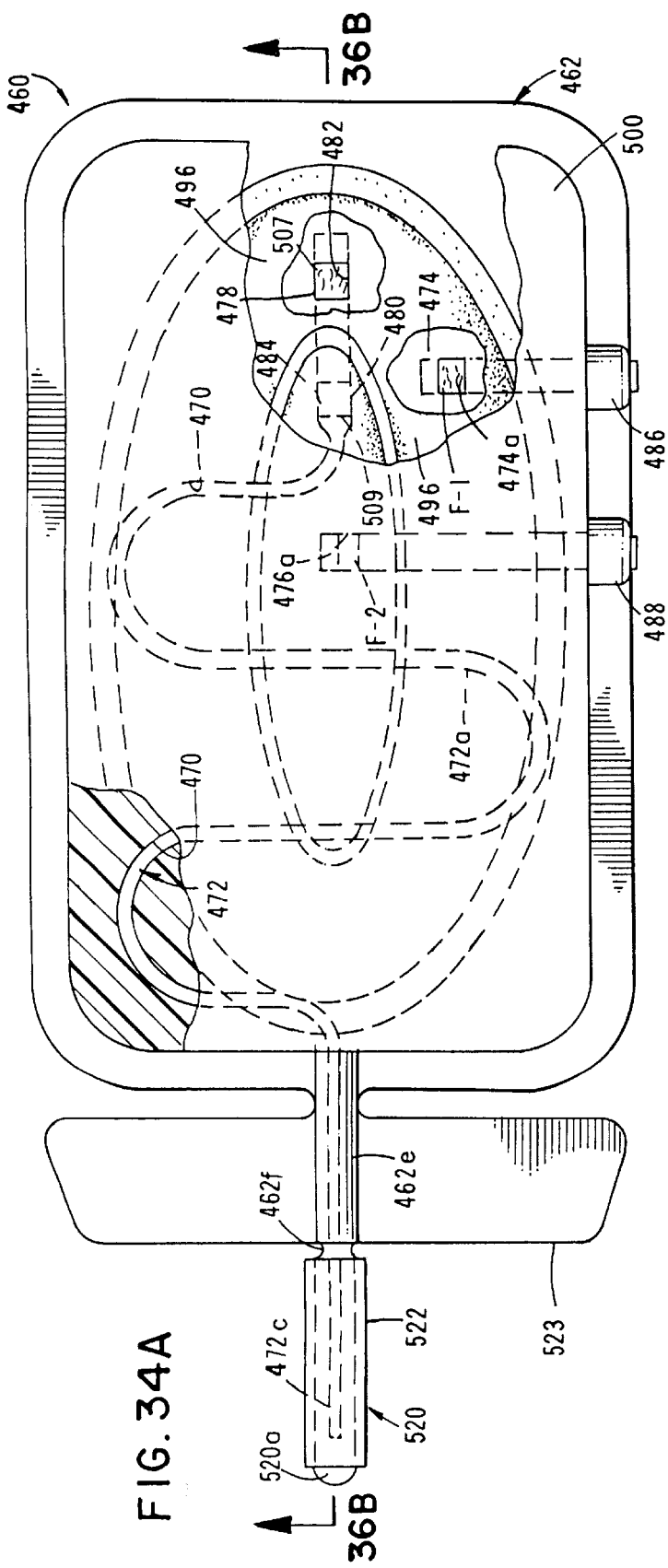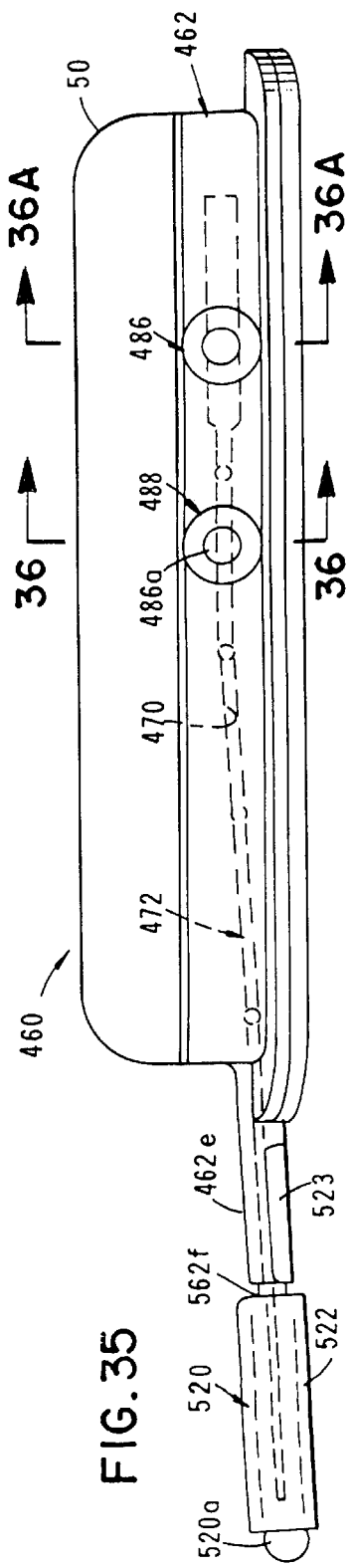

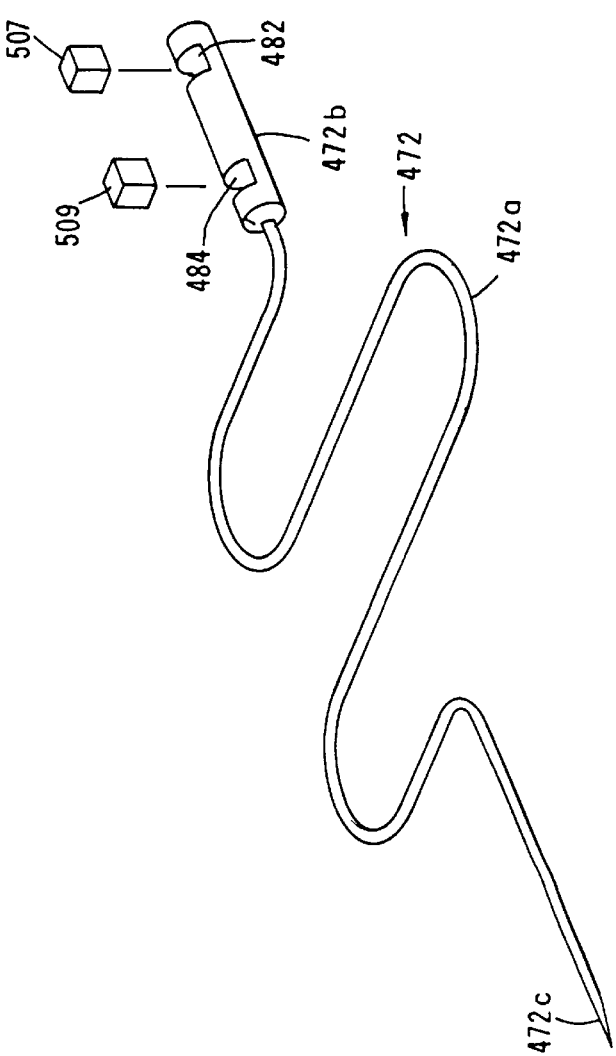
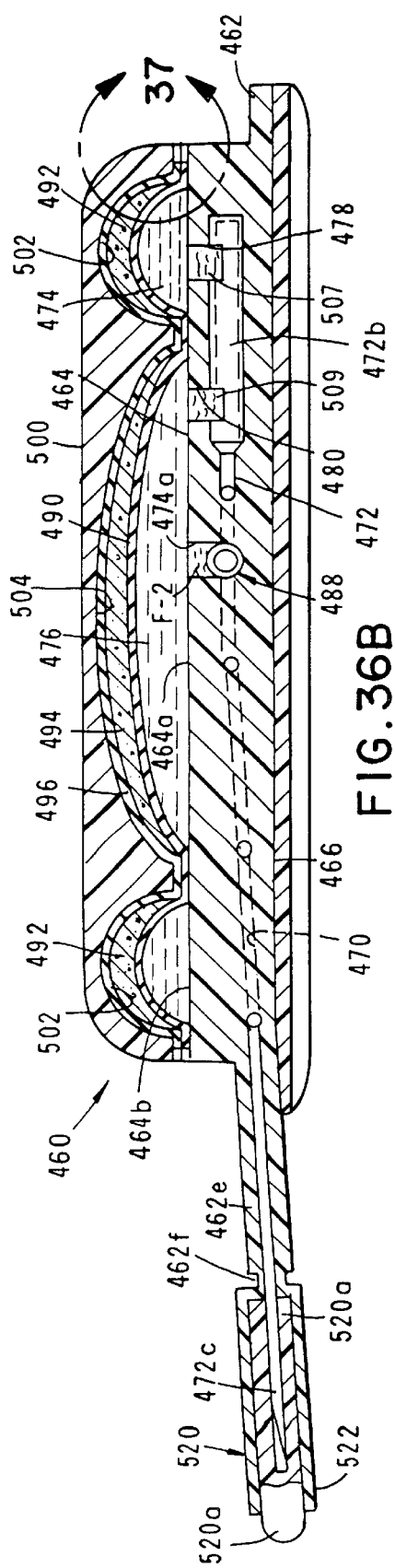
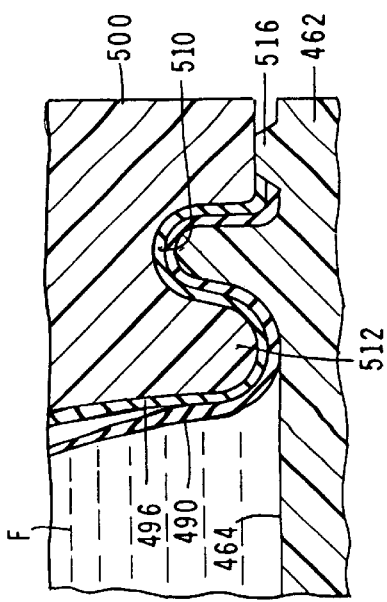
FIG. 36B
FIG. 37A
FIG. 37

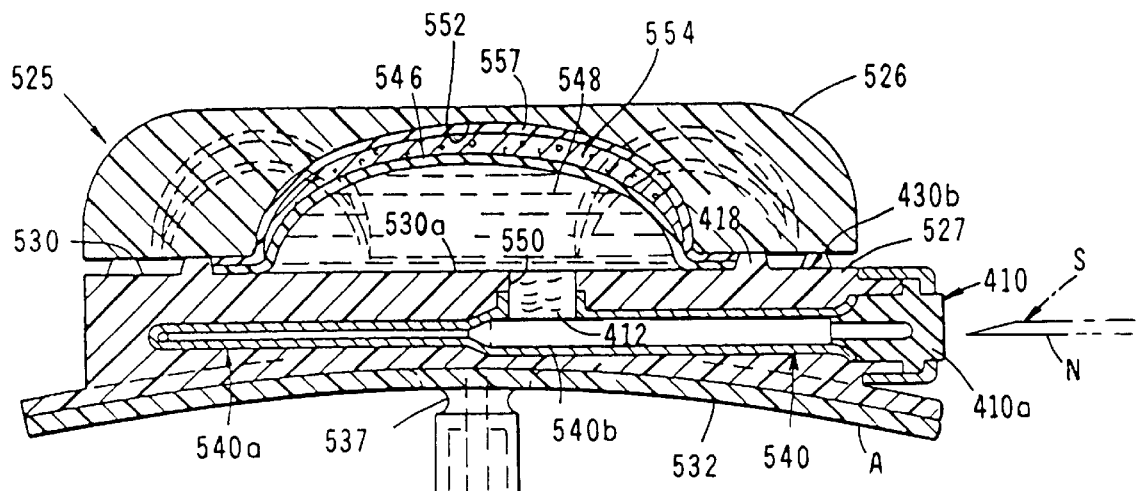
FIG. 40
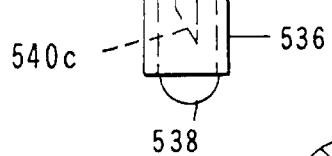
FIG. 40A
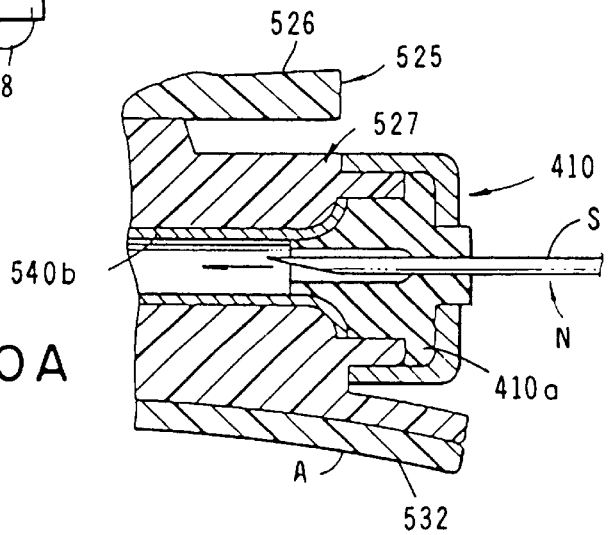
FIG. 41
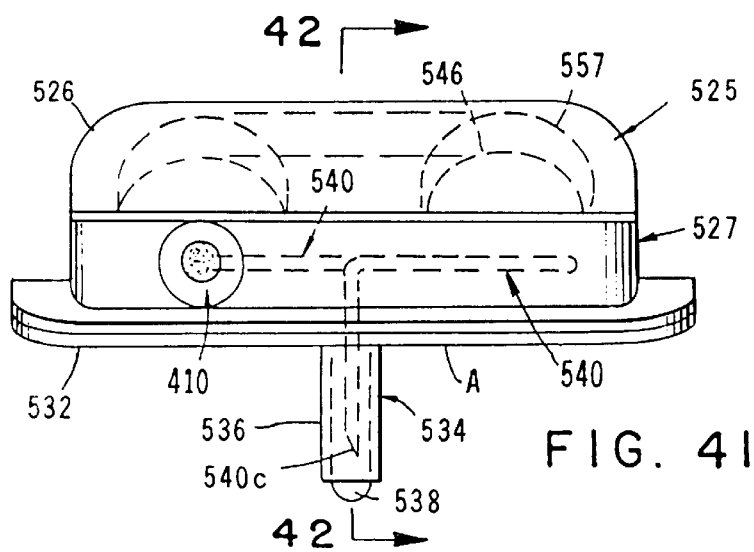

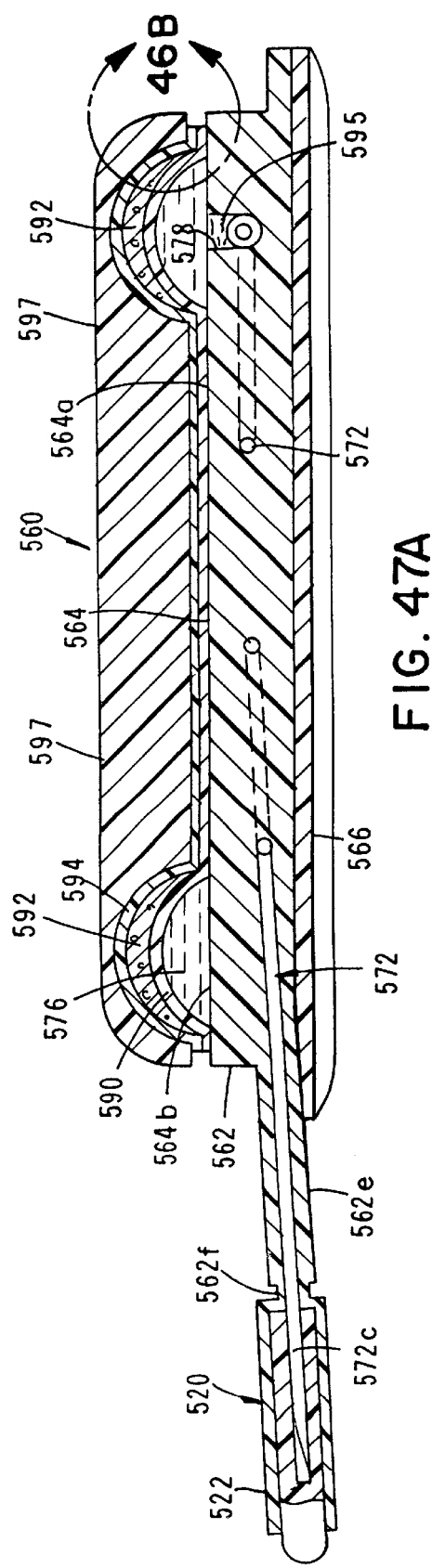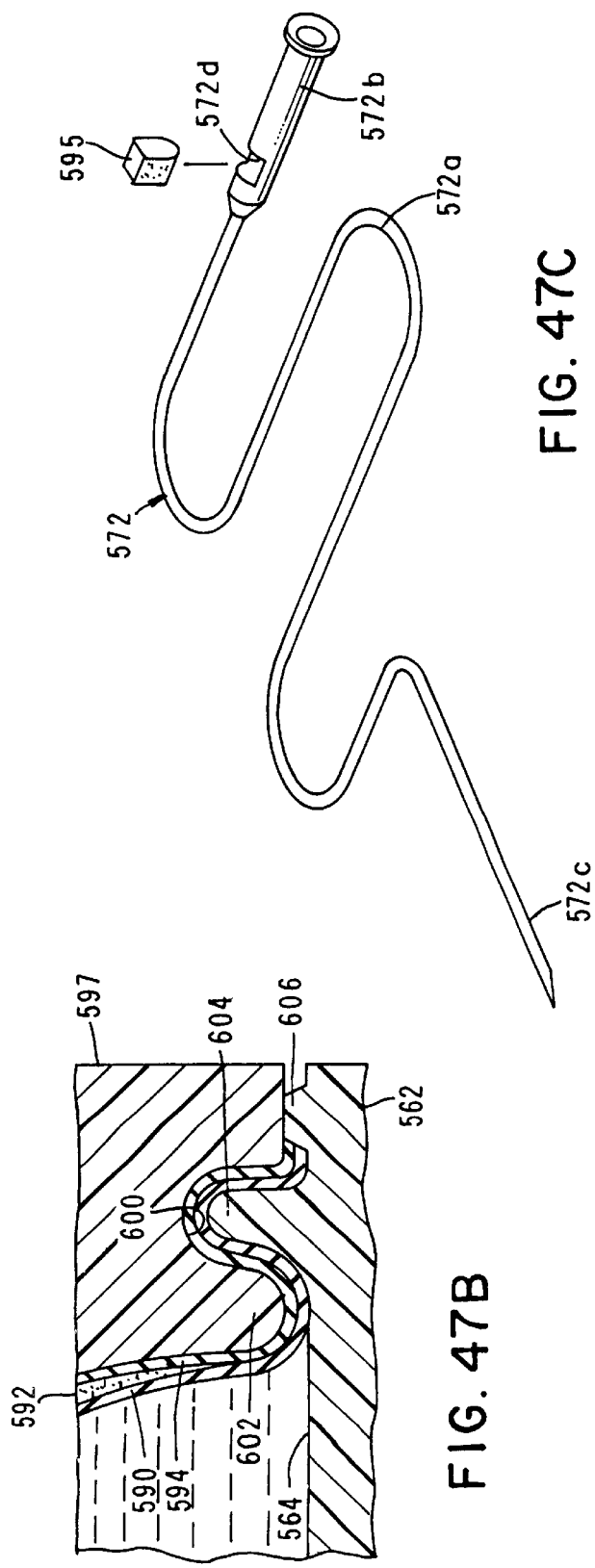
FIG. 47A
FIG. 47B
FIG. 47C

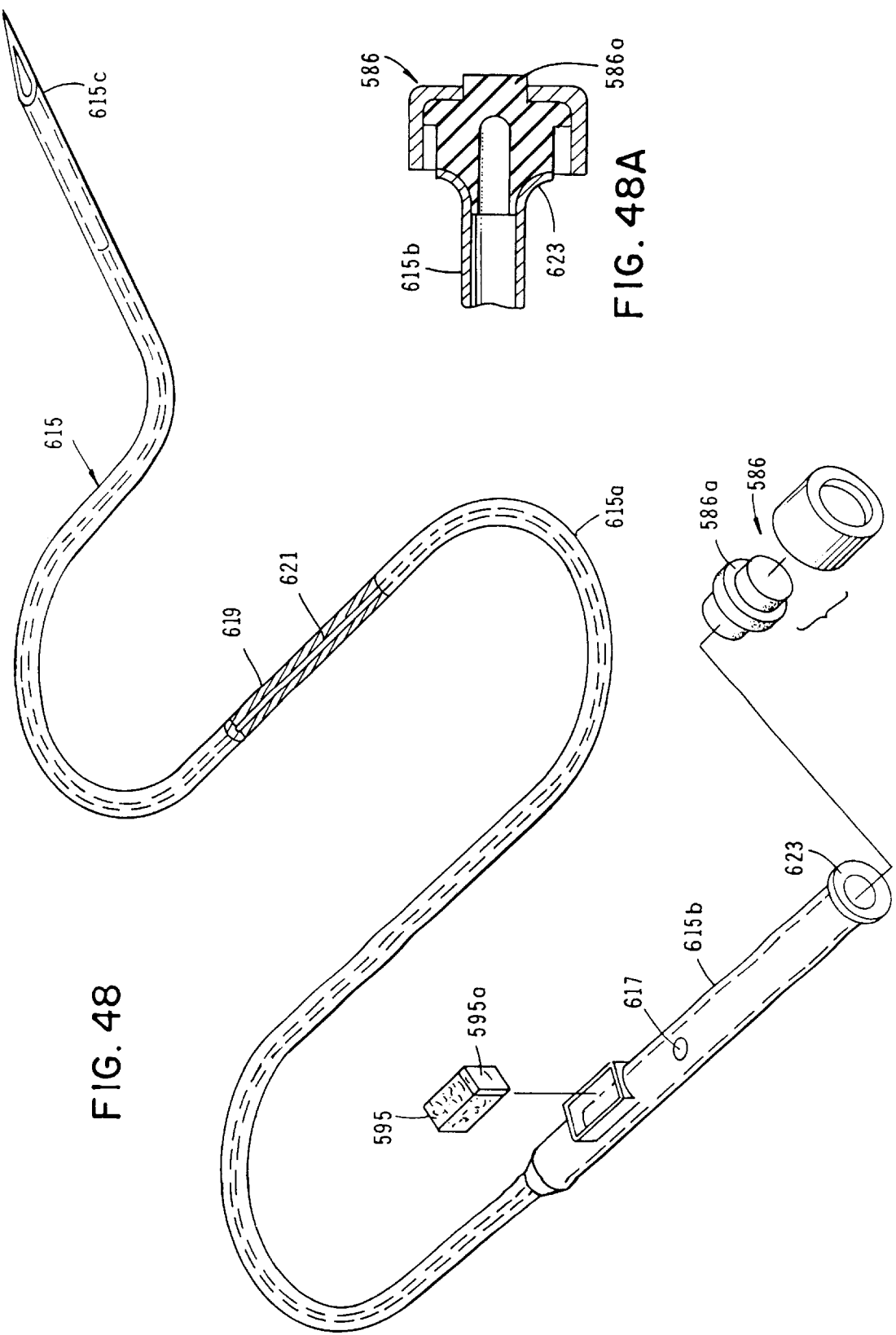

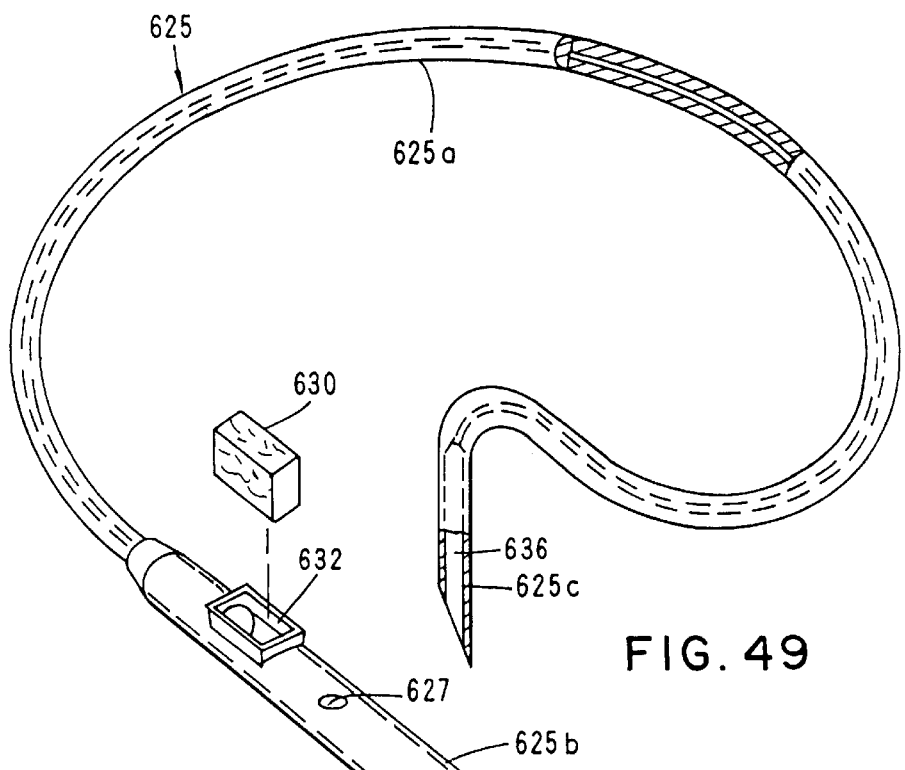
FIG. 49
FIG. 49A
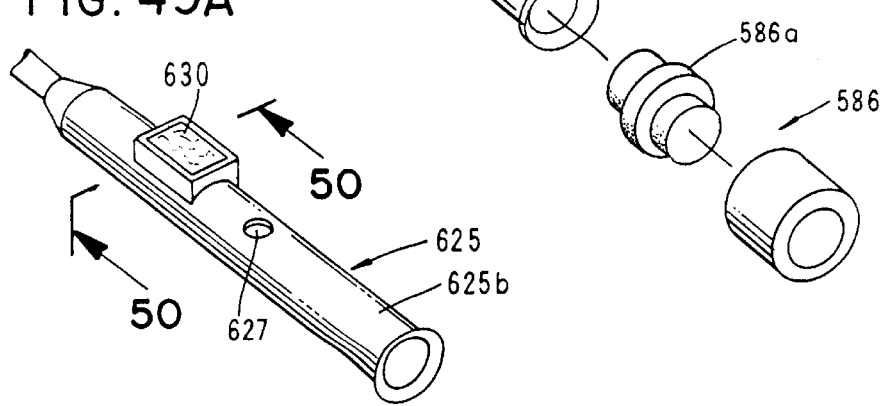
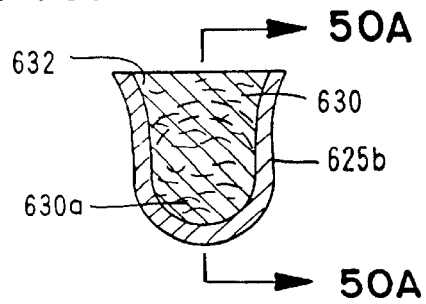
FIG. 50
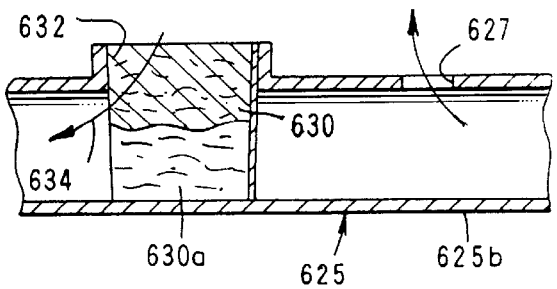
FIG. 50A

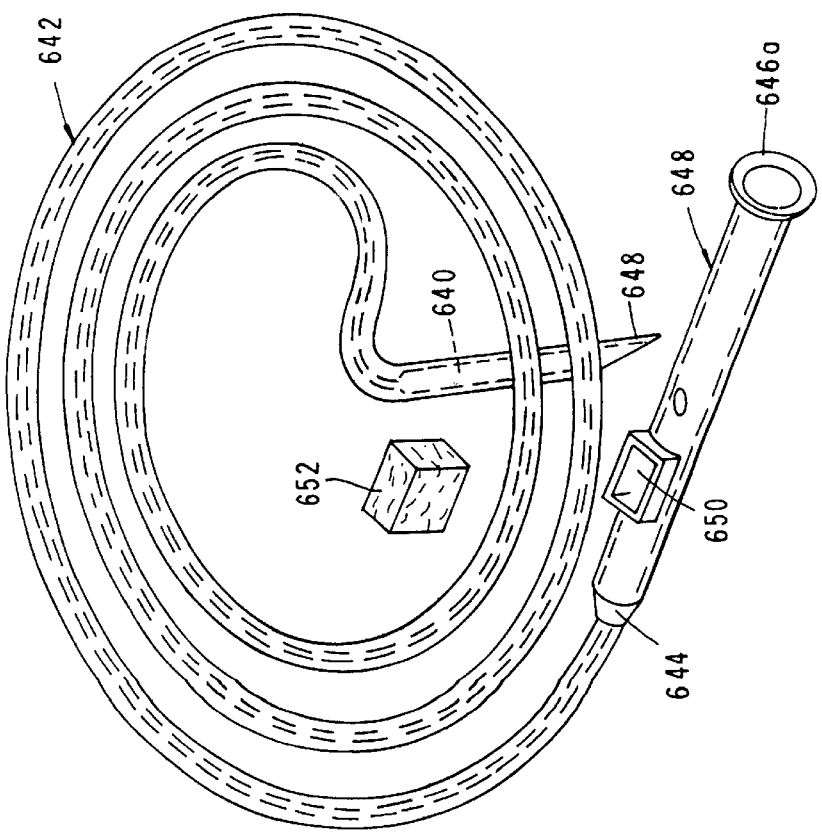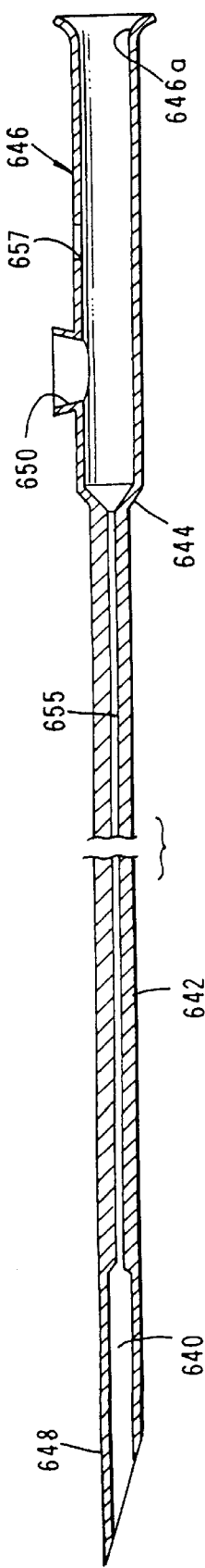

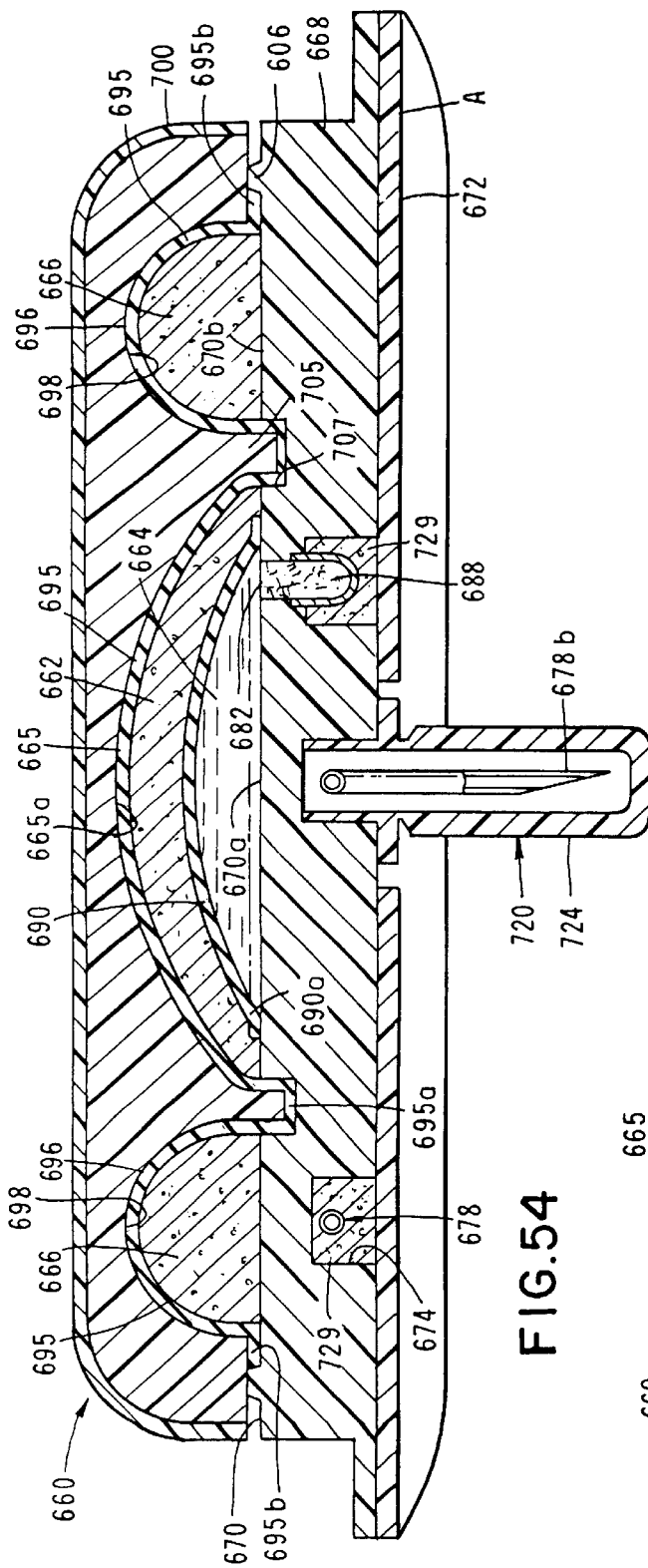
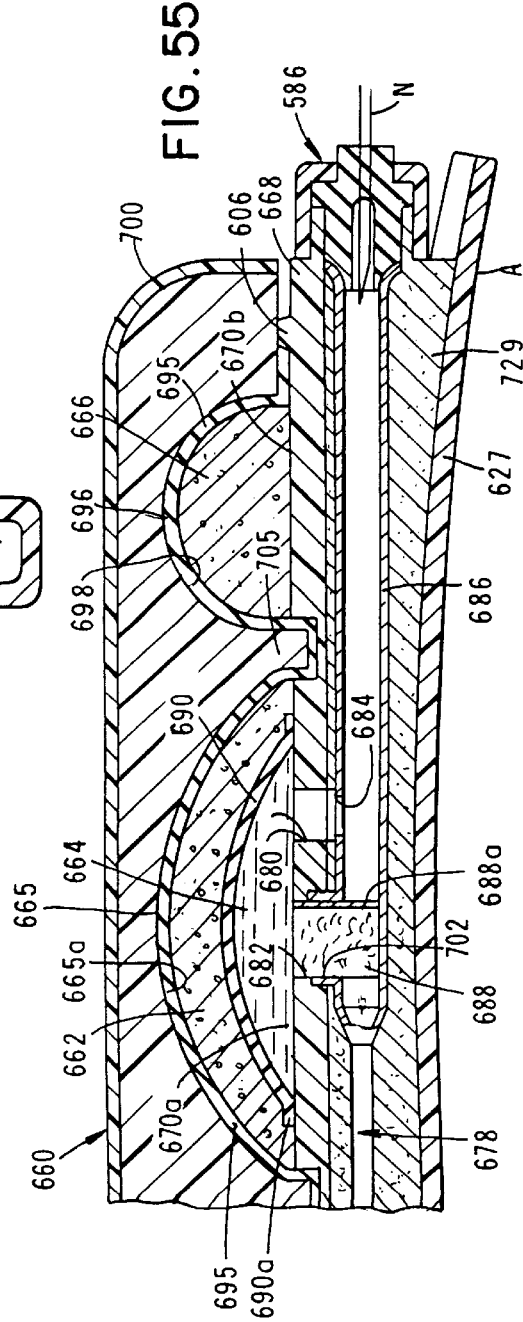
FIG. 54
FIG. 55

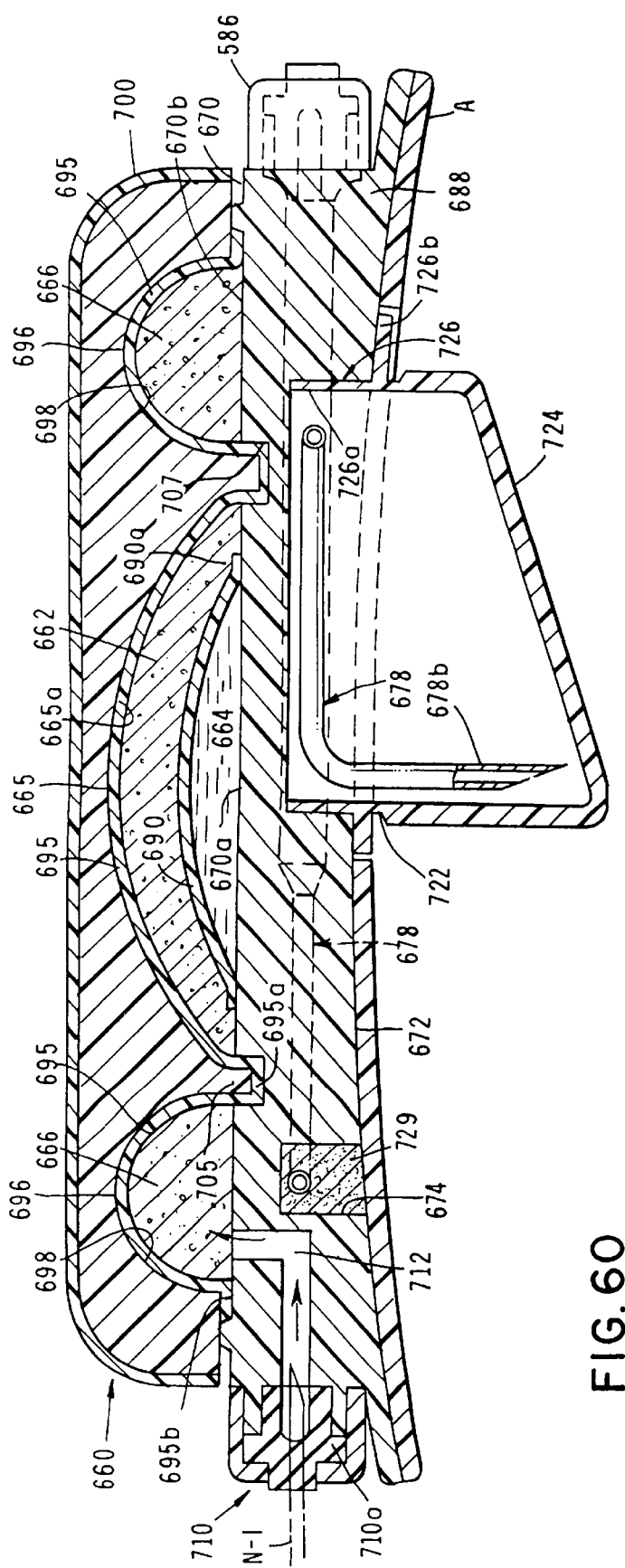
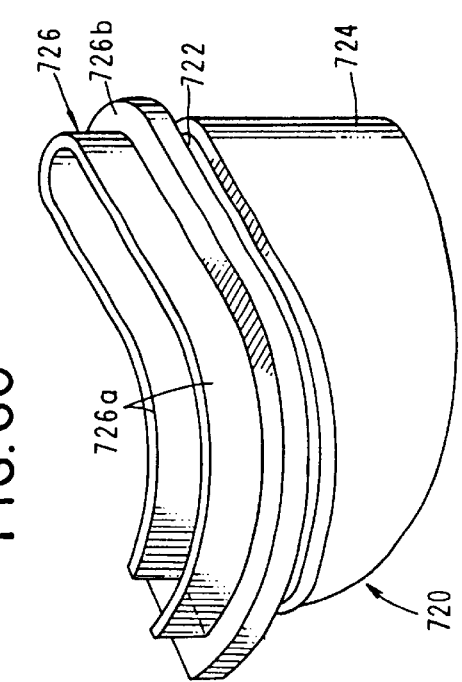
FIG. 57
FIG. 60

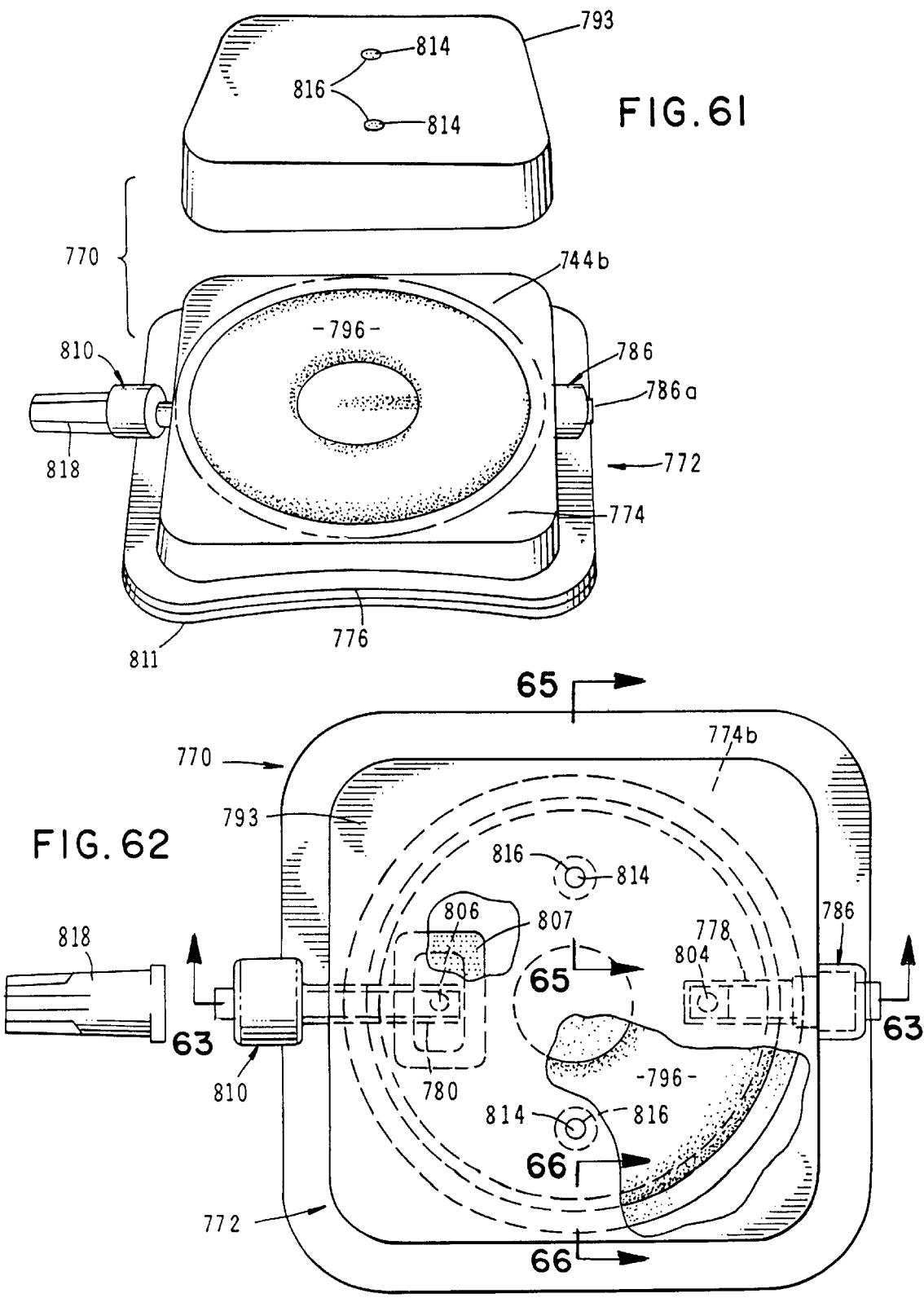

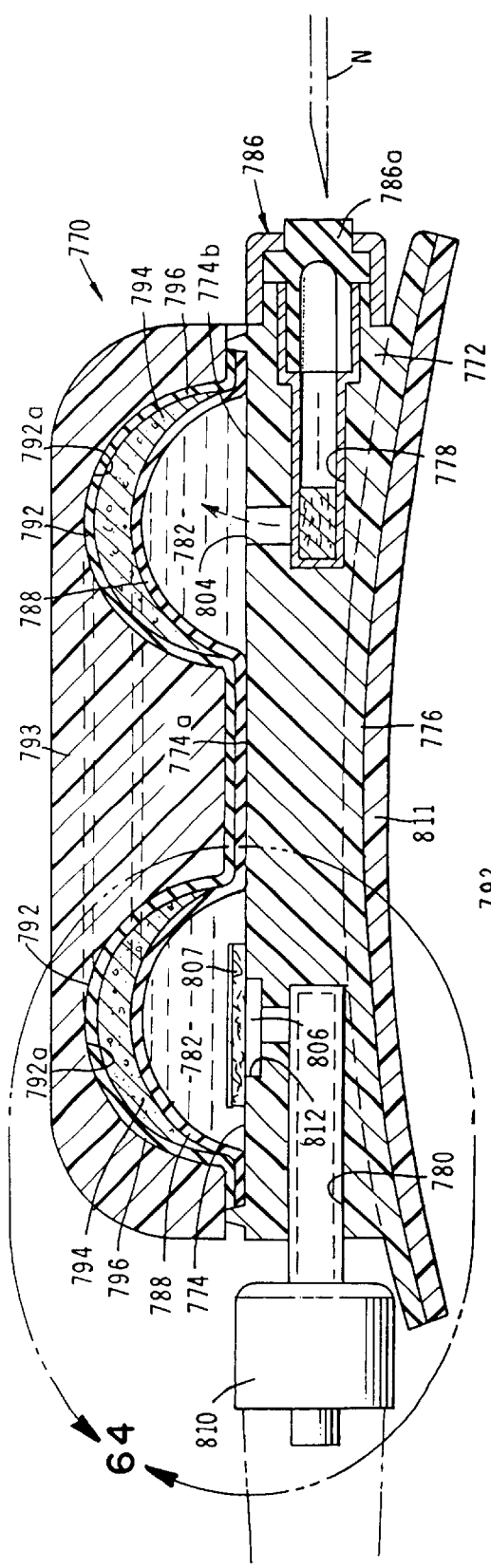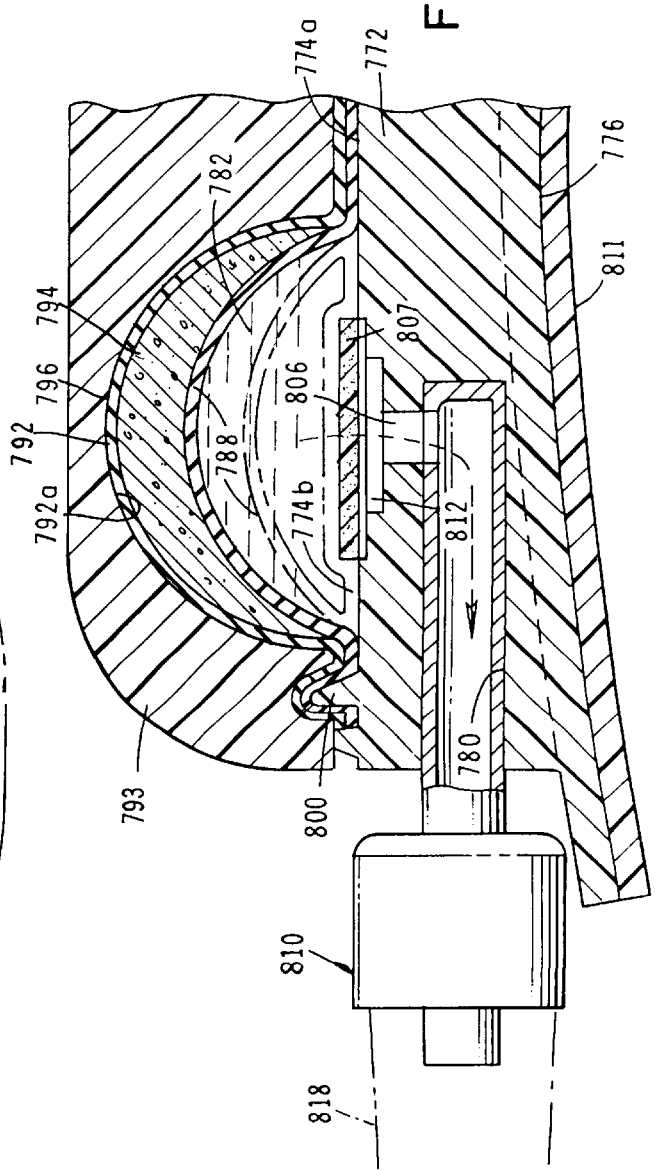

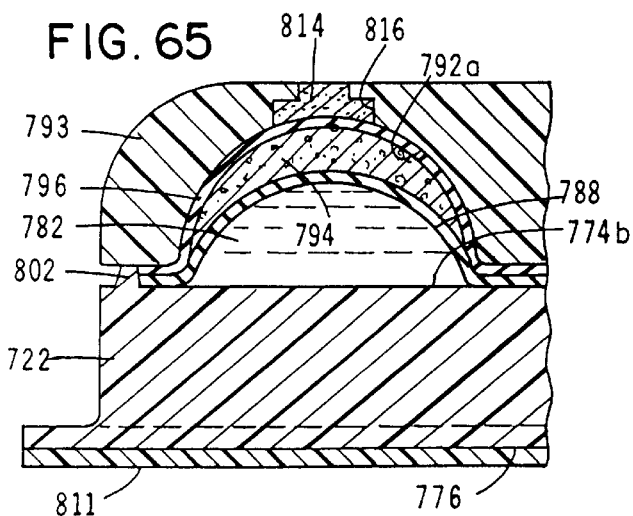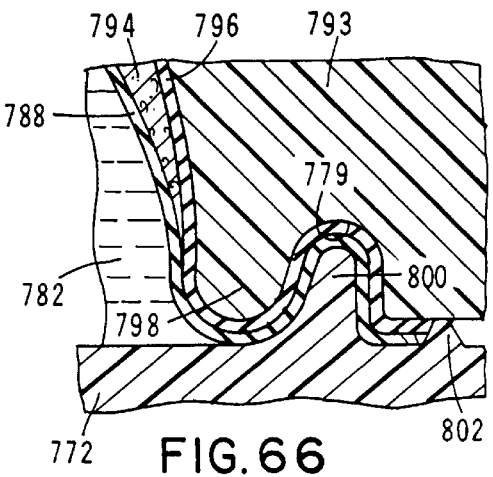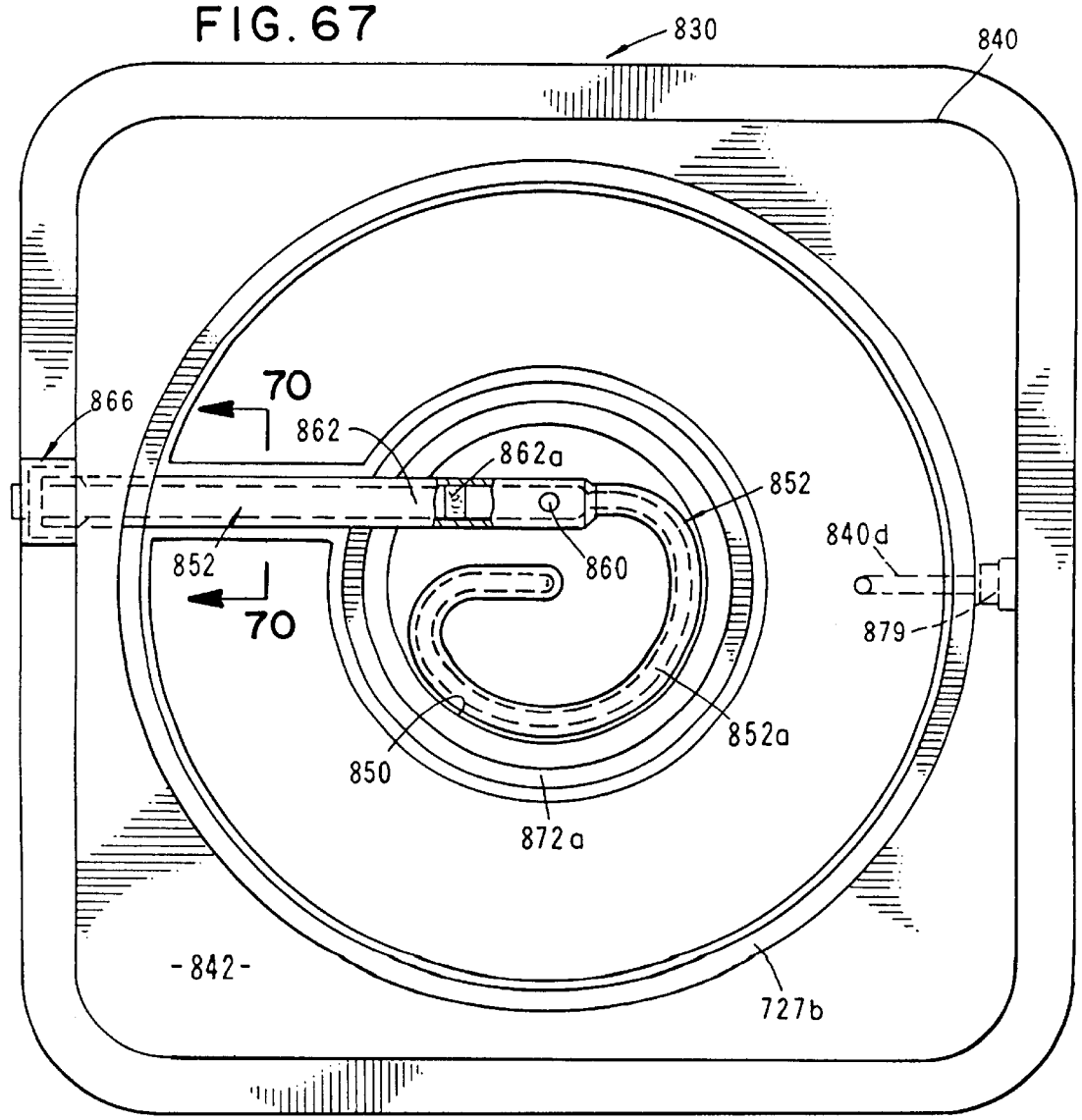

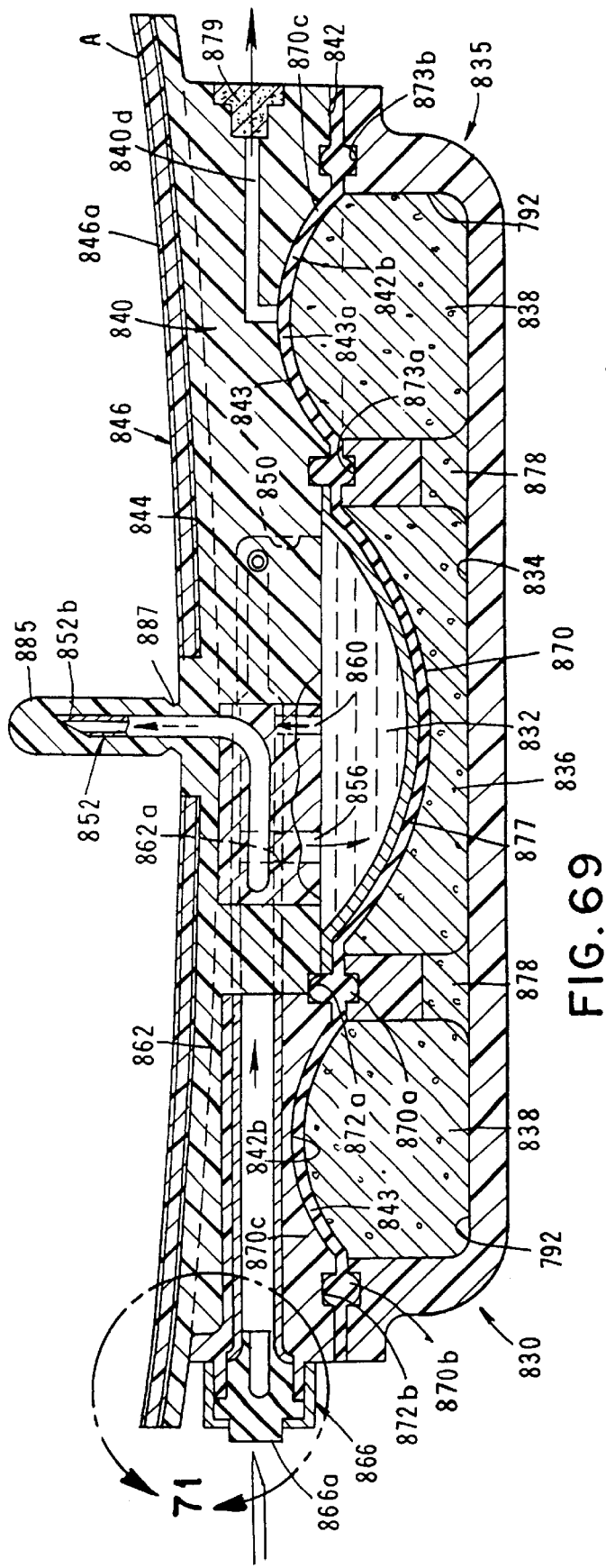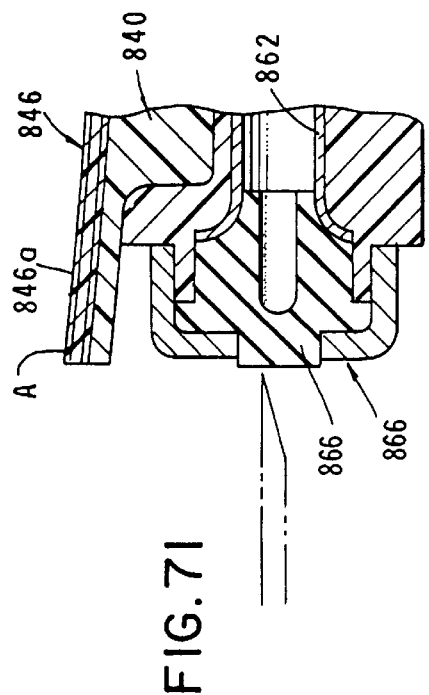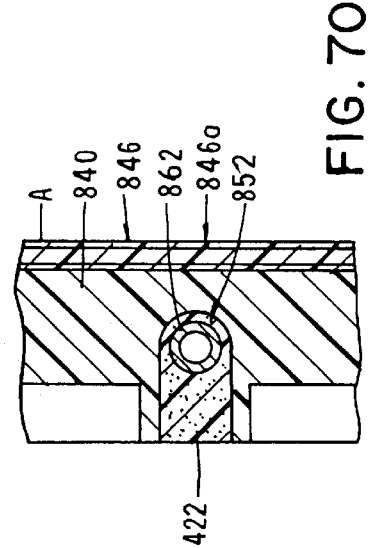
FIG. 69
FIG. 71
FIG. 70

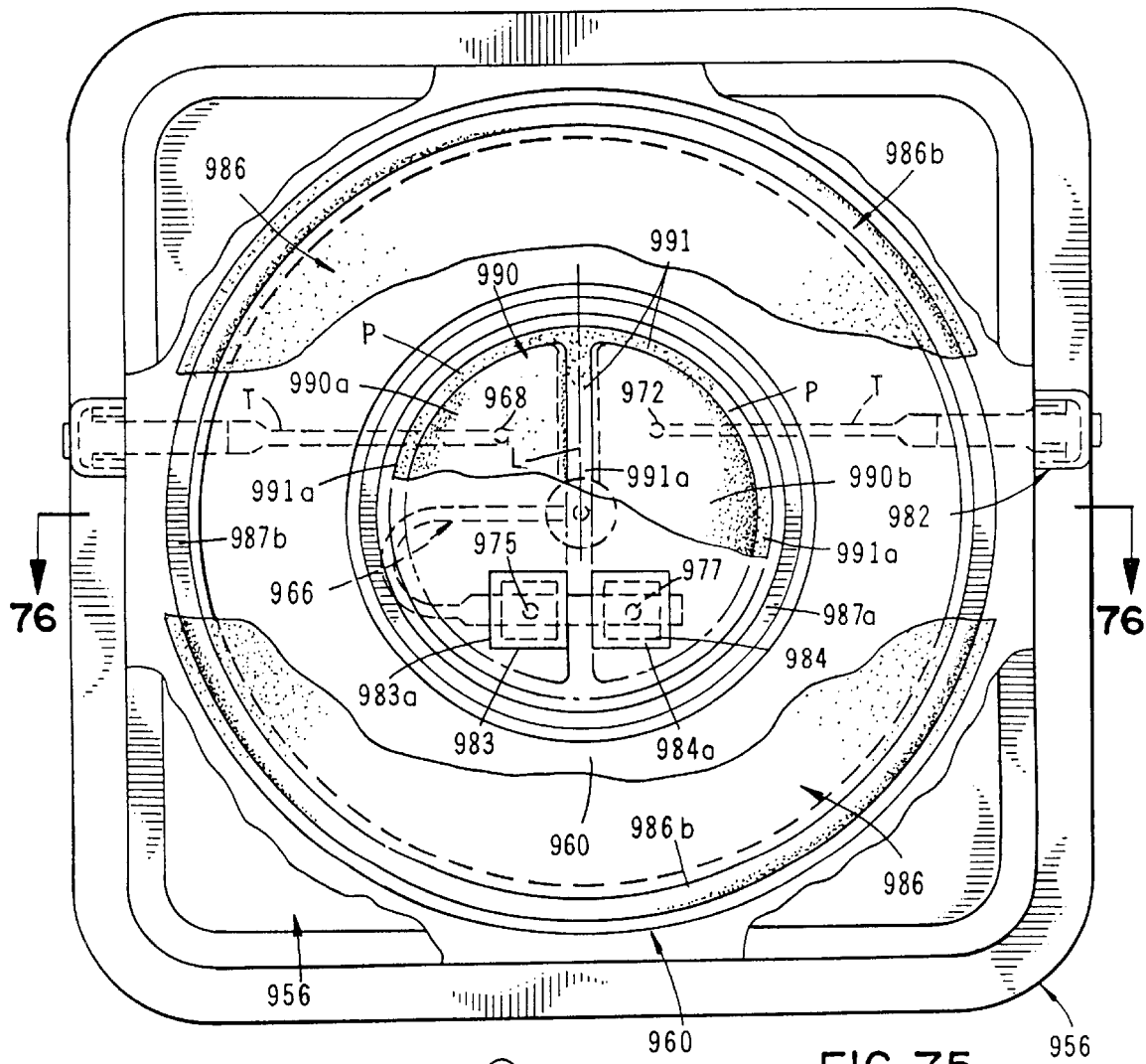
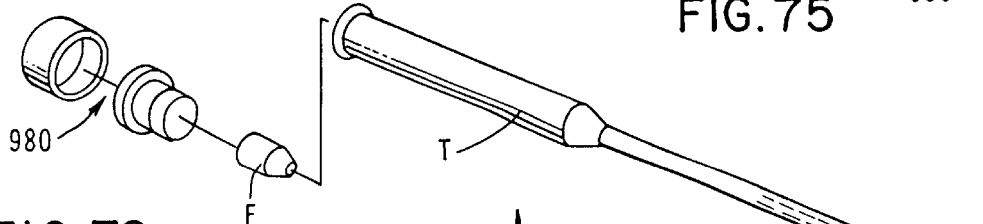
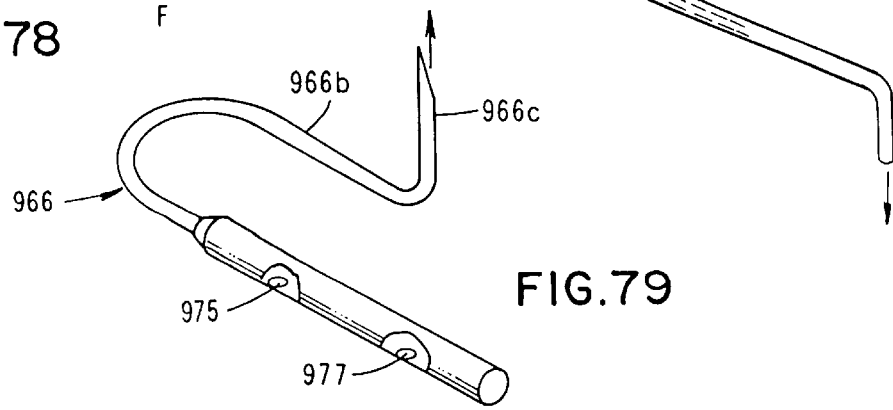
FIG. 75
FIG. 78
FIG. 79

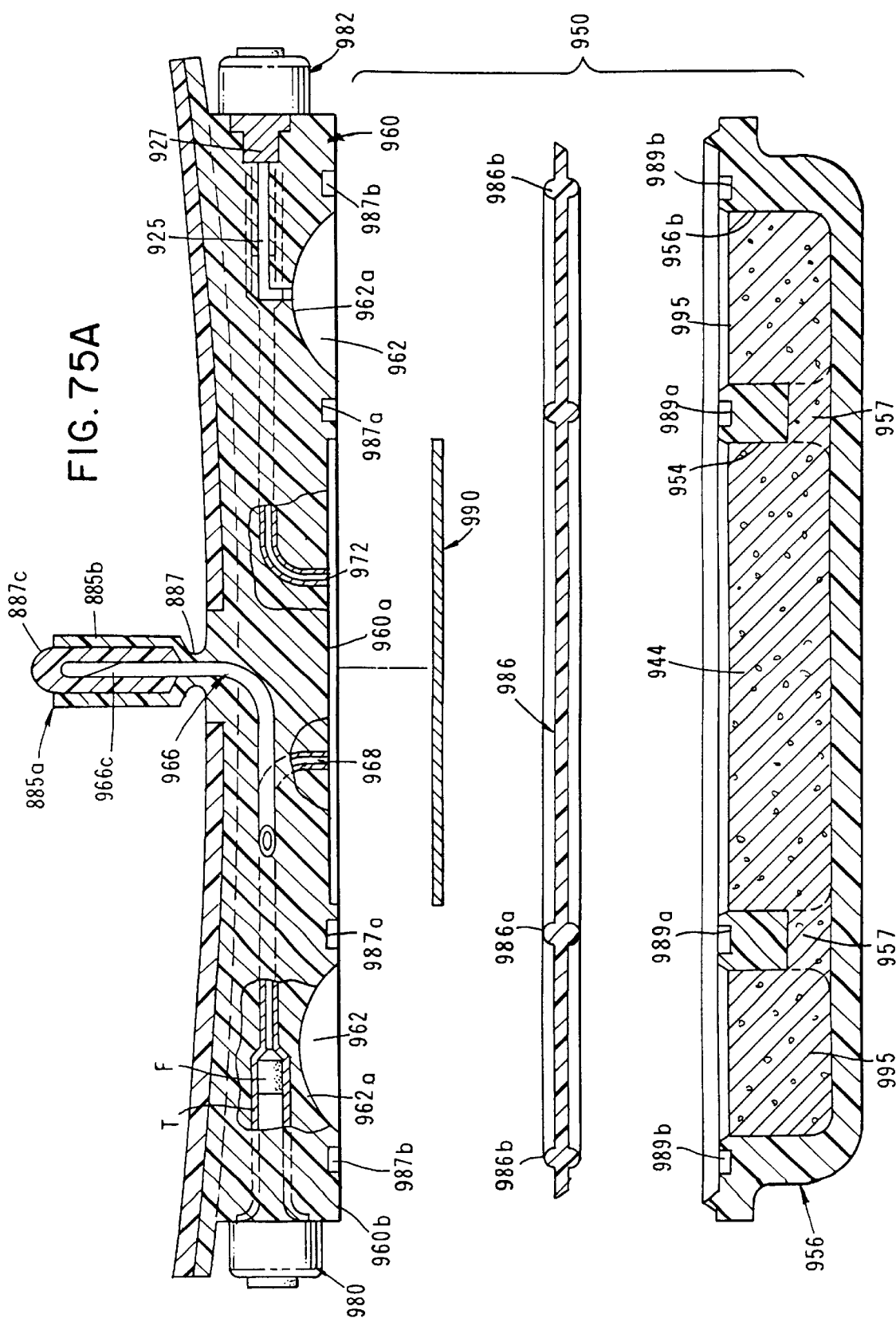

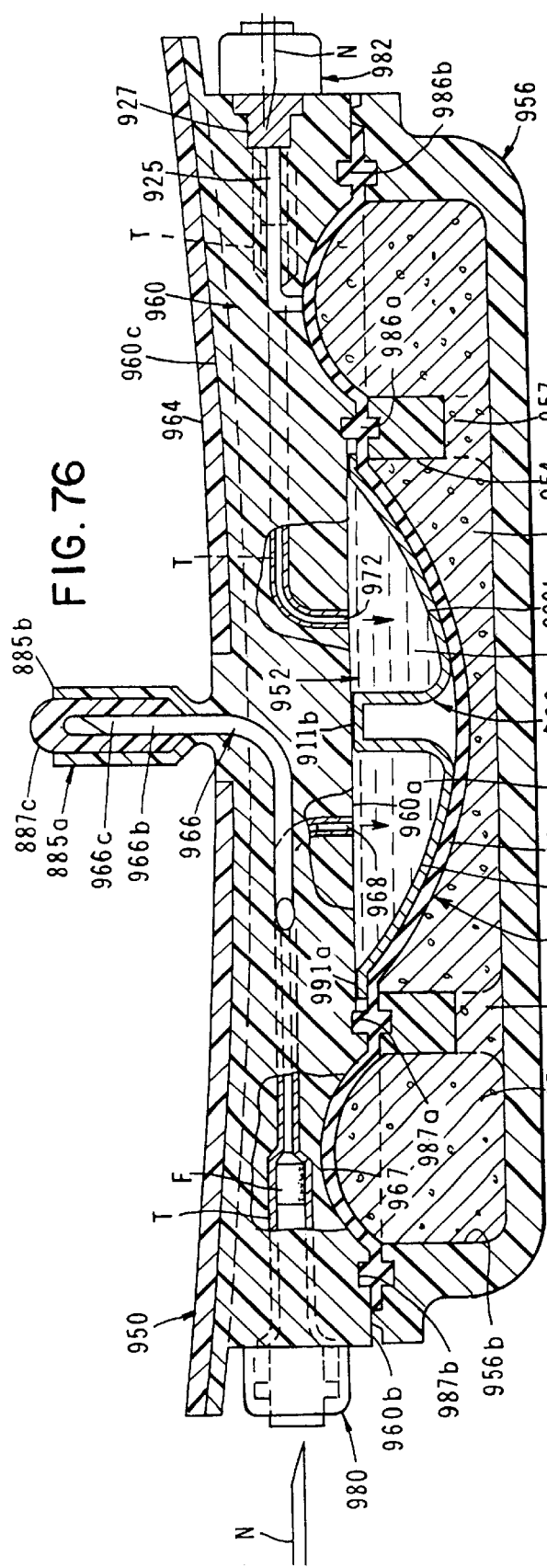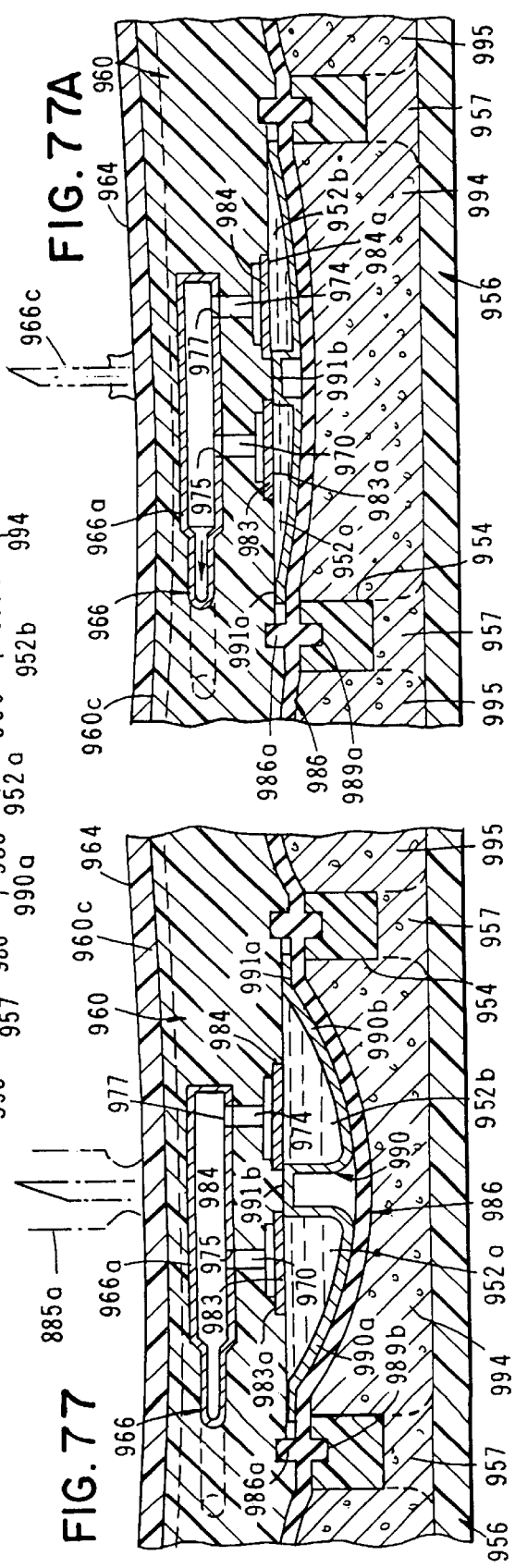

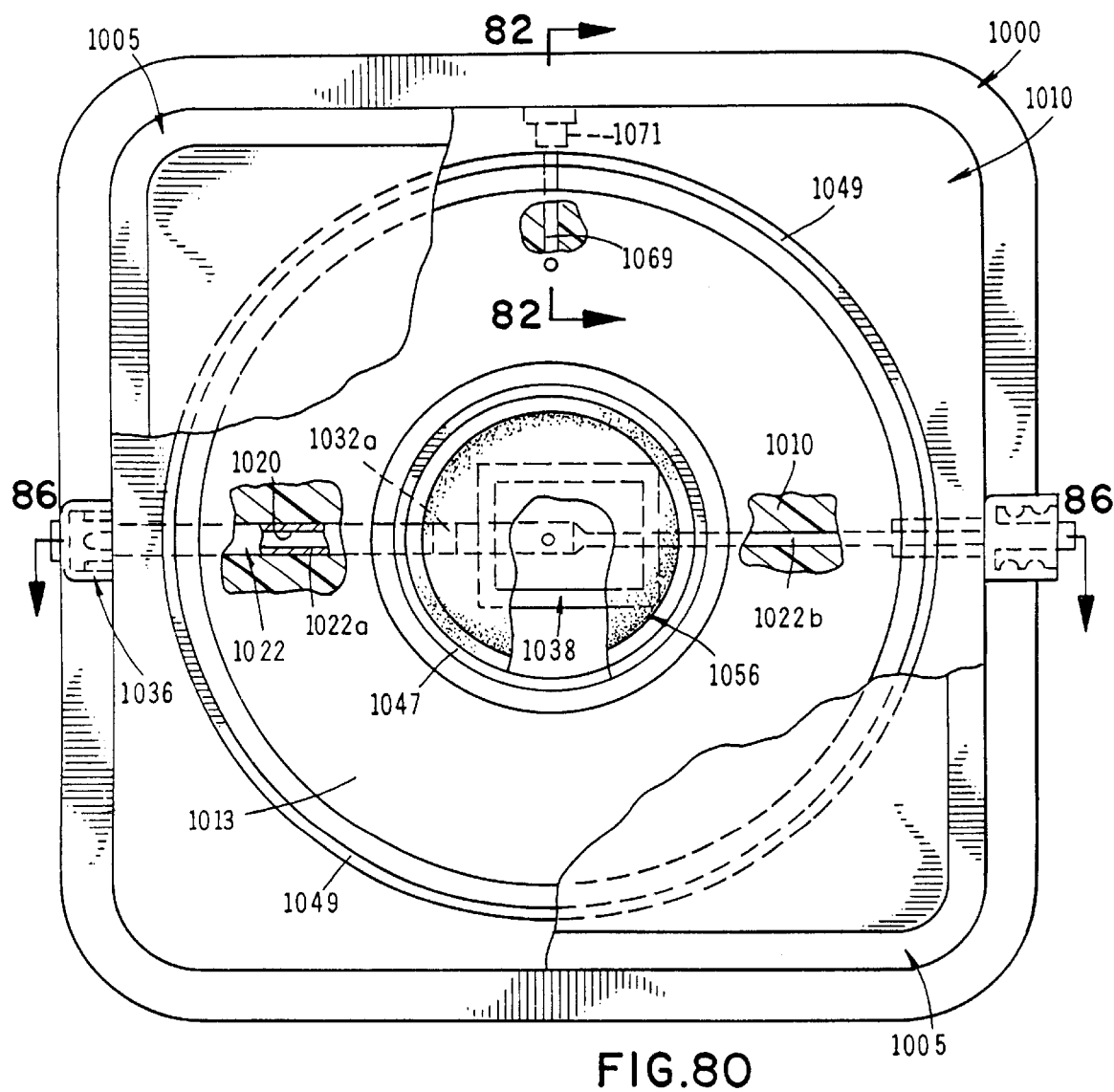
FIG.80
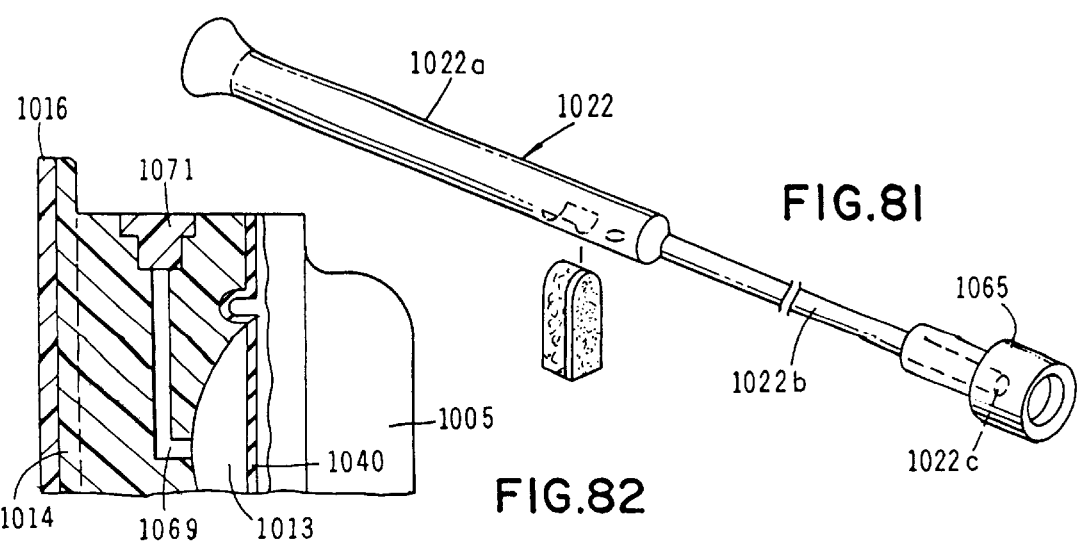
FIG.81
FIG.82

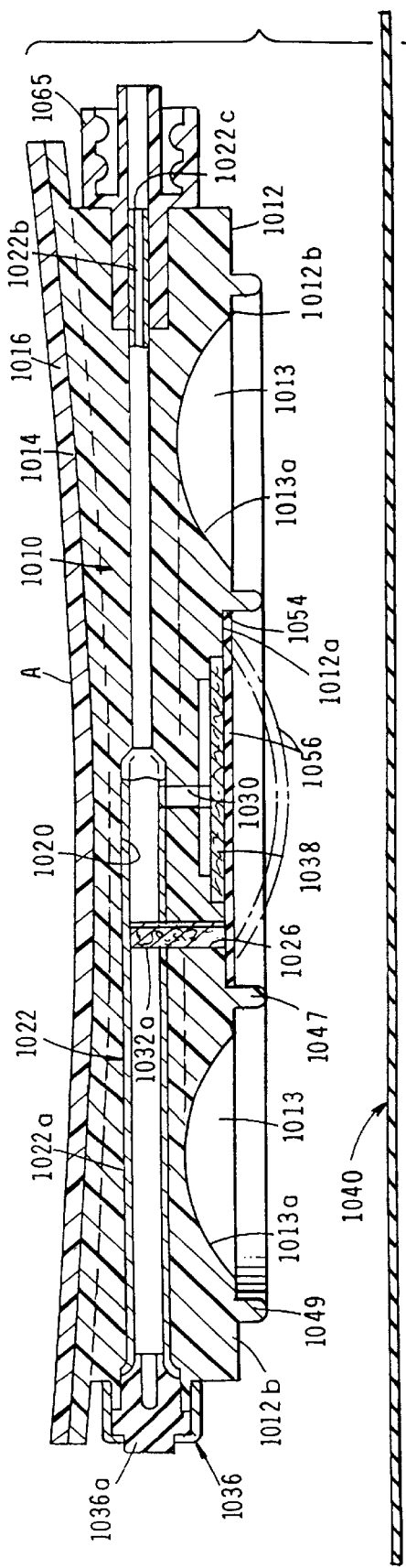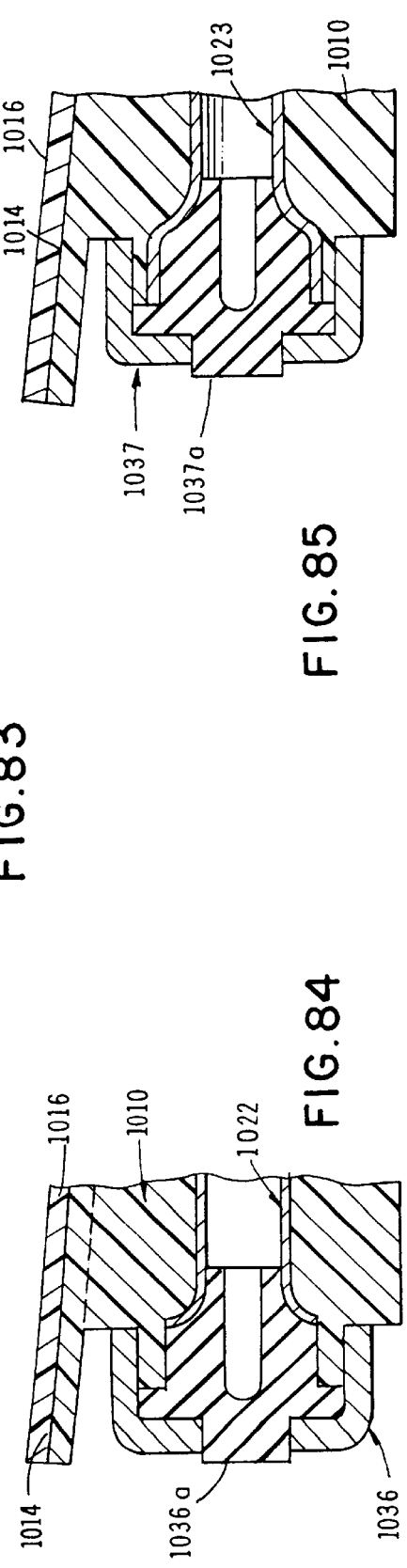
FIG. 83
FIG. 84
FIG. 85

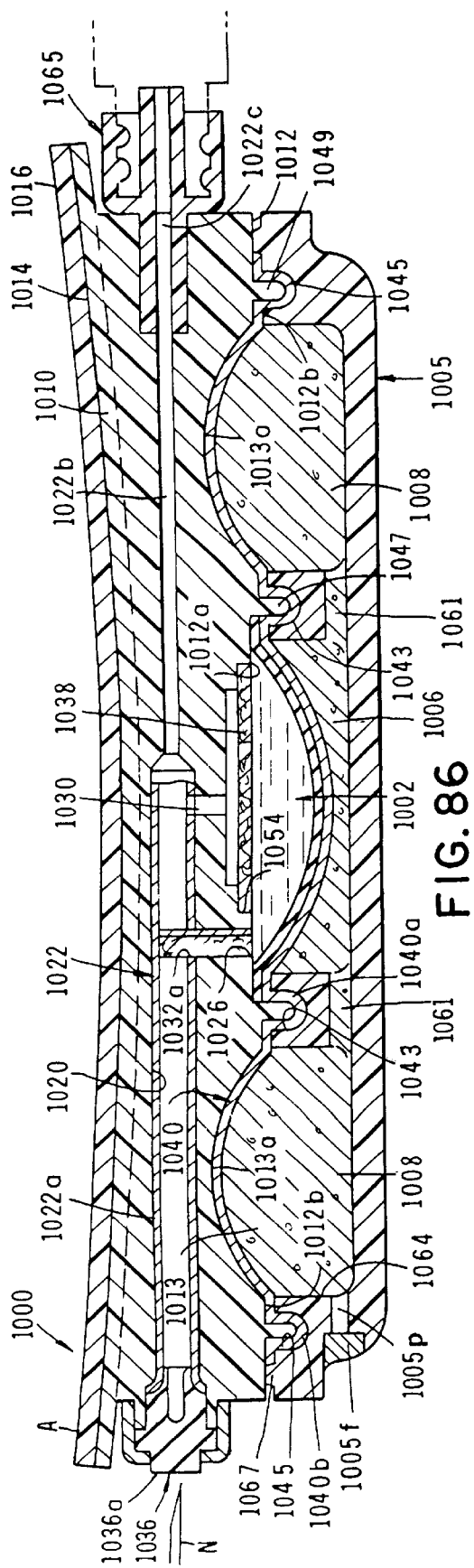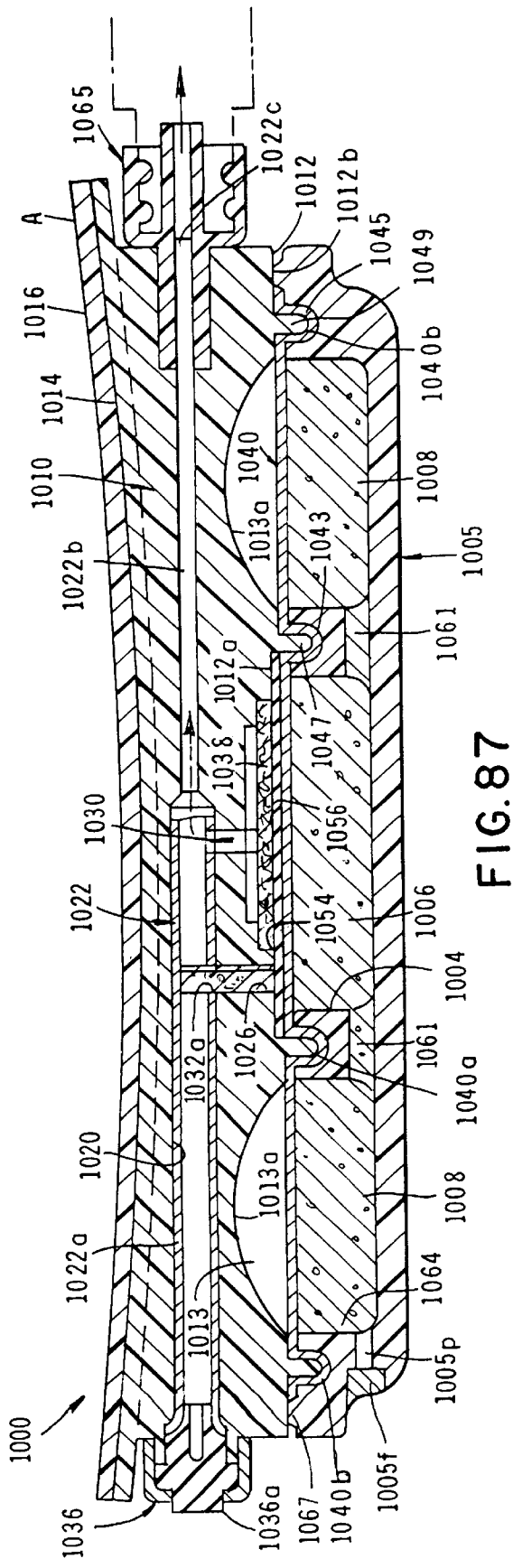

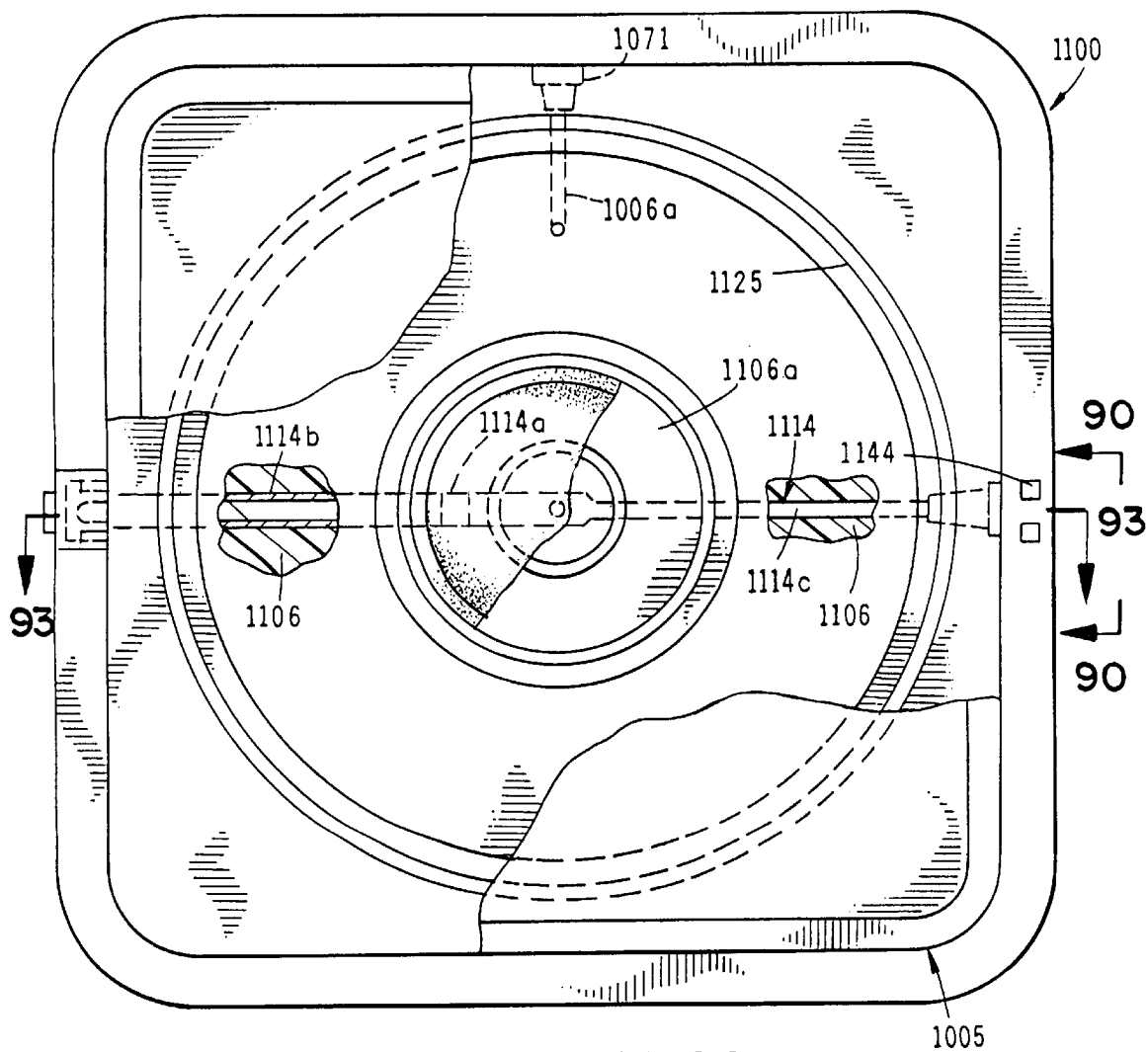
FIG. 88
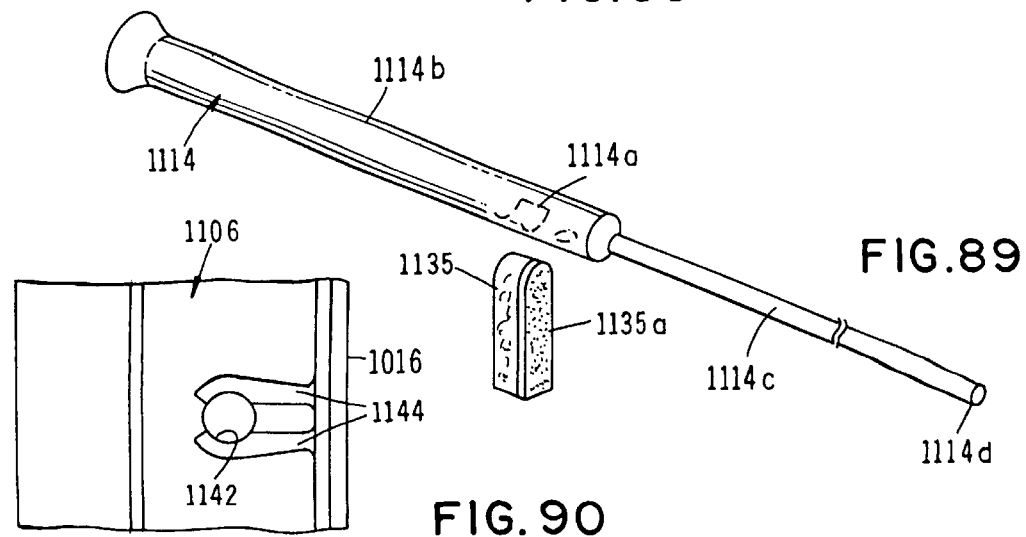
FIG. 89
FIG. 90

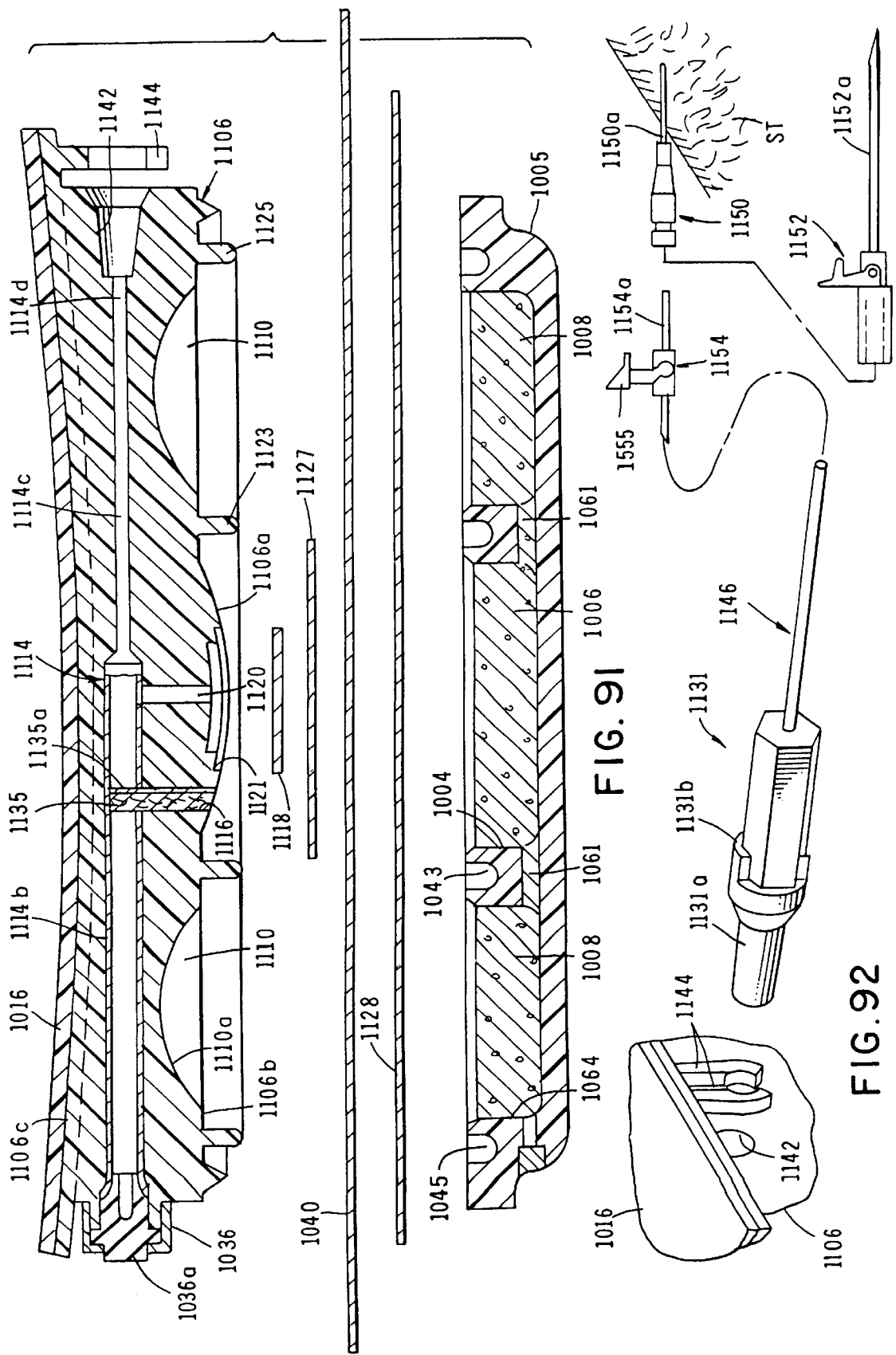

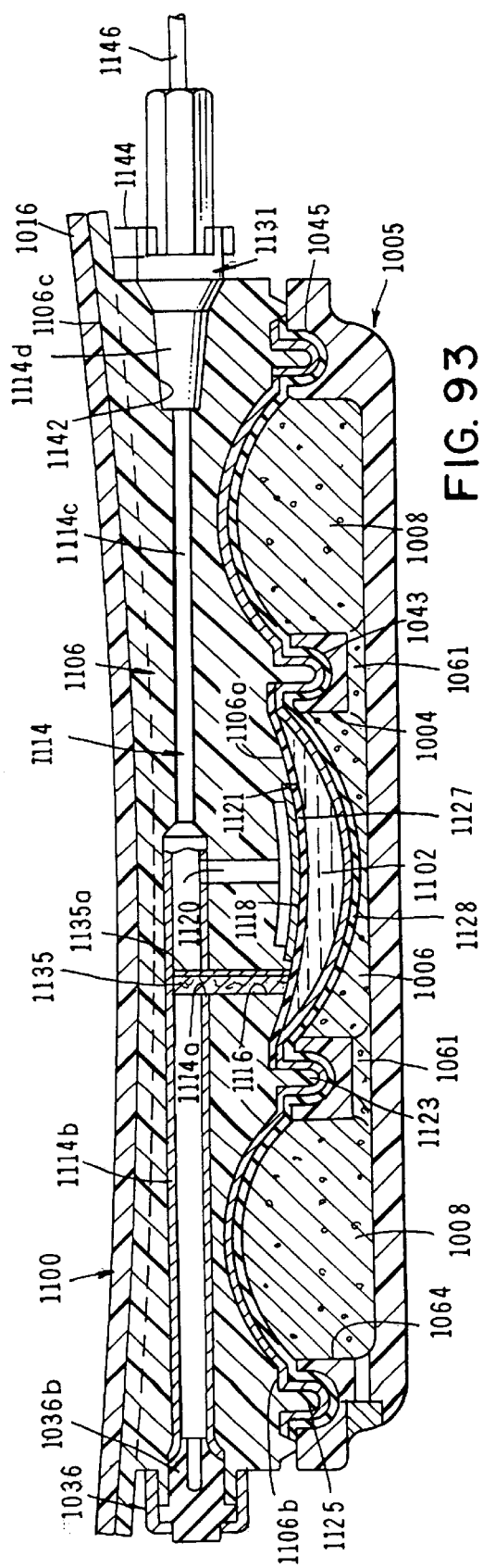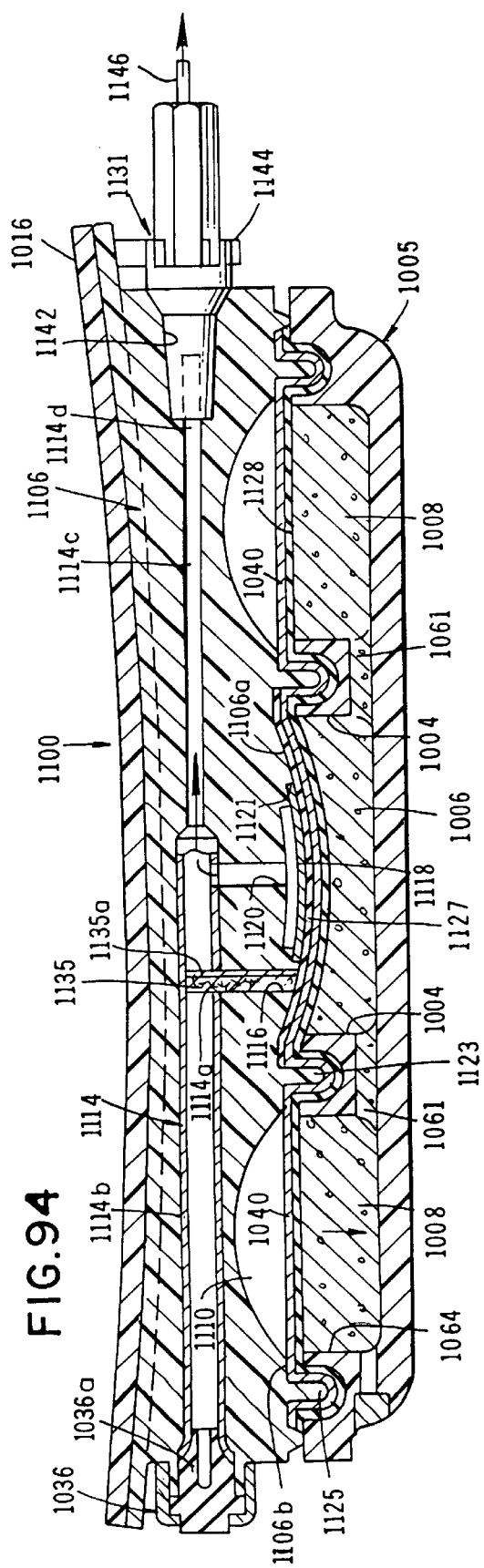

FLUID DELIVERY DEVICE

BACKGROUND OF THE INVENTION

This is a Divisional of application Ser. No. 08/540,914, filed Oct. 11, 1995, now U.S. Pat. No. 5,716,343, which is a Continuation-In-Part application of application Ser. No. 08/451,520, filed May 26, 1995 now U.S. Pat. No. 5,656,032, which is a Continuation-In-Part application of application Ser. No. 08/129,693, filed Sep. 29, 1993 now U.S. Pat. No. 5,419,771; which is a Continuation In Part Application of application Ser. No. 08/069,937, filed May 28, 1993 which has now issued into U.S. Pat. No. 5,336,188; which is a Continuation In Part of application, Ser. No. 08/046,438 filed May 18, 1993 which has now issued into U.S. Pat. No. 5,411,480; which is a Continuation In Part of application Ser. No. 07/987,021 filed Dec. 7, 1992 which has now issued into U.S. Pat. No. 5,279,558; which is a Continuation In Part application of application Ser. No. 07/870,269 filed Apr. 17, 1992 which has now issued into U.S. Pat. No. 5,205,820; which is a Continuation In Part of application Ser. No. 07/642,208 filed Jan. 16, 1991, which has now issued to U.S. Pat. No. 5,169,389 which is a Continuation In Part of application Ser. No. 07/367,304 filed Jun. 16, 1989 which has now issued to U.S. Pat. No. 5,019,047.

FIELD OF THE INVENTION

The present invention relates generally to fluid delivery devices. More particularly, the invention concerns an improved apparatus for infusing medicinal agents into an ambulatory patient at specific rates over extended periods of time.

DISCUSSION OF THE INVENTION

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films, expandable foams and similar materials, which, in cooperation with a base defines a fluid chamber that contains the fluid which is to be dispensed. The elastomeric film membrane or the expandable foam member controllably forces fluid within the chamber into fluid flow channels provided in the base.

The elastomeric film materials used in the apparatus of the present invention, as well as various alternate constructions of the apparatus, are described in detail in U.S. Pat. No. 5,205,820 issued to the present inventor. Therefore, U.S. Pat. No. 5,205,820 is hereby incorporated by reference in its entirety as though fully set forth herein. Co-pending U.S. Ser. No. 08/129,693 filed by the present inventor on Sep. 29, 1993 also describes various types of expandable cellular elastomers and elastomeric foams used in making the expandable member of various physical embodiments of the invention. This co-pending application is also hereby incorporated by reference in its entirety as though fully set forth herein.

The apparatus of the present invention can be used with minimal professional assistance in an alternate health care environment, such as the home. By way of example, devices of the invention can be comfortably and conveniently removably affixed to the patient's body and can be used for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

One of the embodiments of the invention described in Continuation-In-Part application Ser. No. 08/129,693 comprises a generally circular base assembly and a stored energy means provided in the form of a thin, generally circular shaped, prestressed distendable elastomeric membrane which cooperates with the base assembly to form a fluid reservoir. Superimposed over the base assembly is a rigid, distendable membrane engagement means which provides an ullage within the reservoir.

The embodiments of the invention described herein comprise improvements to the devices described in U.S. Pat. No. 5,205,820 and in U.S. Ser. No. 08/129,693. More particularly, the inventions described herein are directed toward providing novel fluid delivery devices which are extremely low profile and are eminently capable of meeting the most stringent of fluid delivery tolerance requirements. In this regard, medical and pharmacological research continues to reveal the importance of the manner in which a medicinal agent is administered. The delivery device, while not an active pharmacological agent, may enhance the activity of the drug by mediating its therapeutic effectiveness. For example, certain classes of pharmacological agents possess a very narrow dosage range of therapeutic effectiveness, in which case too small a dose will have no effect, while too great a dose can result in toxic reaction. In other instances, some forms of medication require an extended delivery time to achieve the utmost effectiveness of a medicinal therapeutic regimen.

By way of example, the therapeutic regimens used by insulin-dependent diabetics provide a good example of the benefits of carefully selected delivery means. The therapeutic object for diabetics is to consistently maintain blood glucose levels within a normal range. Conventional therapy involves injecting insulin by syringe several times a day, often coinciding with meals. The dose must be calculated based on glucose levels present in the blood. If the dosage is off, the bolus administered may lead to acute levels of either glucose or insulin resulting in complications, including unconsciousness or coma. Over time, high concentrations of glucose in the blood can also lead to a variety of chronic health problems, such as vision loss, kidney failure, heart disease, nerve damage, and amputations.

A recently completed study sponsored by the National Institutes of Health (NIH) investigated the effects of different therapeutic regimens on the health outcomes of insulin dependent diabetics. This study revealed some distinct advantages in the adoption of certain therapeutic regimens. Intensive therapy that involved intensive blood glucose monitoring and more frequent administration of insulin by conventional means, i.e., syringes, throughout the day saw dramatic decreases in the incidence of debilitating complications.

The NIH study also raises the question of practicality and patient adherence to an intensive therapy regimen. A bona fide improvement in insulin therapy management must focus on the facilitation of patient comfort and convenience as well as dosage and administration schemes. Basal rate delivery of insulin by means of a convenient and reliable delivery device over an extended period of time represents one means of improving insulin management. Basal rate delivery involves the delivery of very small volumes of fluid (1–3 mL.) over comparatively long periods of time (18–24 hours). As will be appreciated from the discussion which follows, the apparatus of the present invention is uniquely suited to provide precise fluid delivery management at a low cost in those cases where a variety of precise dosage schemes are of utmost importance.

In those embodiments of the invention described in U.S. Pat. No. 5,205,820 issued to the present inventor and incorporated herein by reference, the fluid delivery apparatus components generally included: a base assembly; an elastomeric membrane serving as a stored energy means; fluid flow channels for filling and delivery; flow control means; a cover; and an ullage, which comprised a part of the base assembly. The ullage in these devices typically comprises a semi-rigid structure having flow channels leading from the top of the structure through the base to inlet or outlet ports of the device.

In the rigid ullage configuration, the stored energy means of the device must be superimposed over the ullage to form the fluid-containing reservoir from which fluids are expelled at a controlled rate by the elastomeric membrane of the stored energy means tending to return to a less distended configuration in a direction toward the ullage. With these constructions, the stored energy membrane is typically used at high extensions over a significantly large portion of the pressure-deformation curve (FIG. 1A).

Elastomeric membrane materials suitable for use as the stored energy means must possess certain physical characteristics in order to meet the performance requirements for a fluid delivery apparatus. More particularly, for good performance, the elastomeric membrane material must have good memory characteristics under conditions of high extension; good resistance to chemical and radiological degradation; and appropriate gas permeation characteristics depending upon the end application to be made of the device.

Once an elastomeric membrane material is chosen that will optimally meet the desired performance requirements, there still remain certain limitations to the level of refinement of the delivery tolerances that can be achieved using the rigid ullage configuration. These result primarily from the inability of the rigid ullage to conform to the shape of the elastomeric membrane near the end of the delivery period. This nonconformity can lead to extended delivery rate tail-off and higher residual problems when extremely accurate delivery is required. For example, when larger volumes of fluid are to be delivered, the tail-off volume represents a smaller portion of the fluid amount delivered and therefore exhibits much less effect on the total fluid delivery profile, but in very small dosages, the tail-off volume becomes a larger portion of the total volume. This sometimes places severe physical limits on the range of delivery profiles that may easily be accommodated using the rigid ullage configuration.

An acceptable elastomeric membrane material candidate for the rigid ullage configuration must also be drug compatible as is typically in contact with any drug containing fluid disposed within the reservoir. Many currently available elastomeric membrane materials, due to their chemical composition or means of manufacturing, are not drug compatible. This compatibility restriction, combined with strict physical requirements, results in further limitation of available selections for the candidate elastomeric material for use in devices embodying a rigid ullage structure.

As will be better appreciated from the discussion which follows, the apparatus of the present invention provides a unique and novel improvement for a disposable dispenser of simple but highly reliable construction that may be adapted to many applications of use. A particularly important aspect of the improved apparatus is the incorporation of a conformable ullage made of yieldable materials, the conformable ullage uniquely conforms to the shape of elastomeric membrane as the membrane returns to its less distended configuration. This novel construction will satisfy even the most stringent delivery tolerance requirements and will elegantly overcome the limitations of materials selection encountered in devices embodying the rigid ullage construction. Another significant advantage of the novel ullage construction is that the ullage can be located either between the base and the fluid to be delivered, or alternatively, can be located between the elastomeric membrane and the fluid to be delivered. Further, a plurality of subreservoirs can be associated with a single ullage thereby making it possible to incorporate a wide variety of delivery profiles within a single device.

Although the infusion devices described in U.S. Pat. No. 5,205,820 and in U.S. Ser. No. 08/129,693 are very low profile devices, the devices of the inventions described herein are designed in a manner so that they can be of even a lower profile thereby making them ideally suited for use in dispensing medicinal agents such as insulin and the like.

SUMMARY OF THE INVENTION

It is an object of the present invention to provide an apparatus having a self-contained stored energy membrane for expelling fluids at a precisely controlled rate which is of a compact, extremely low profile, laminate construction. More particularly, it is an object of the invention to provide such an apparatus which is of very low profile so that it can conveniently be used for the precise infusion of pharmaceutical fluids, such as insulin and the like, into an ambulatory patient at controlled rates over extended periods of time.

It is another object of the invention to provide an apparatus of the aforementioned character which is small, compact, highly reliable and easy-to-use by lay persons in a non-hospital environment.

It is another object of the invention to provide an apparatus as described in the preceding paragraphs which, in one form, can be used for intravenous infusion of fluids and, in a second form, can be used for subdermal infusion of fluids. In this regard, the apparatus includes a novel and unique delivery cannula having a body portion disposed within a circuitous channel formed within the base superstructure of the apparatus and a pierceable portion which extends outwardly from the base of the apparatus. By constructing the cannula in a circuitous configuration, substantial structural stability of the cannula relative to the base is achieved as compared with a straight cannula protruding from the base.

Another object of the invention is to provide an apparatus which embodies a soft, pliable, conformable mass which defines an ullage within the reservoir of the device which will closely conform to the shape of the stored energy membrane thereby effectively avoiding extended flow delivery rate tail-off at the end of the fluid delivery period.

A further object of the invention is to provide a low profile, fluid delivery device of laminate construction which can meet even the most stringent fluid delivery tolerance requirements.

Another object of the invention is to provide an apparatus of the class described which includes a conformable ullage construction that can be used with a plurality of fluid reservoirs of the same or different volume.

Another object of the invention is to provide an apparatus of the character which includes a novel combination filter and rate control assemblage disposed intermediate the fluid reservoir outlet and the outlet port of the device.

Another object of the invention is to provide an apparatus of the character described which, due to its unique construction, can be manufactured inexpensively in large volume by automated machinery.

Other objects of the invention are set forth in U.S. Pat. No. 5,205,820 which is incorporated herein and still further objects will become more apparent from the discussion which follows.

BRIEF DESCRIPTION OF THE DRAWINGS

FIG. 1 is a top plan view of one form of an ultra low profile device of the invention partly broken away to show internal construction.

FIG. 2 is a generally perspective view of the ultra low profile infusion device shown in FIG. 1.

FIG. 3 is a cross-sectional view taken along lines 3—3 of FIG. 1.

FIG. 4 is a cross-sectional view taken along lines 4—4 of FIG. 1.

FIG. 4A is an enlarged, fragmentary cross-sectional view of area 4A of FIG. 4.

FIG. 4B is an enlarged, generally perspective view of the cannula and flow control means of the form of the invention shown in FIG. 1.

FIG. 5 is an enlarged, generally perspective view of an alternate form of infusion cannula of the invention.

FIG. 6 is an enlarged, generally perspective view of still another alternate form of infusion cannula.

FIG. 7 is a generally perspective top view an alternate form of the ultra low profile infusion device of the invention.

FIG. 8 is a view taken along lines 8—8 of FIG. 7.

FIG. 9 is an enlarged, cross-sectional view taken along lines 9—9 of FIG. 8.

FIG. 12B is a generally perspective view illustrating an alternate method of radially stretching the distendable membrane.

FIG. 12C is a fragmentary, cross-sectional view illustrating the construction of the hydraulically actuated gripping fingers that grip the membrane.

FIG. 21 is a cross-sectional view of the base portion of the embodiment of the invention shown in FIG. 20.

FIG. 21A is a cross-sectional view taken along lines 21A—21A of FIG. 21.

FIG. 22 is a cross-sectional view of still another embodiment of the invention showing an infusion device embodying a conformable ullage and a plurality of subreservoirs.

FIG. 22A is a cross-sectional view taken along lines 22A—22A of FIG. 22.

FIG. 22B is a cross-sectional view taken along lines 22B—22B of FIG. 22.

FIG. 22C is a cross-sectional view similar to FIG. 22, but showing the configuration of the device after the fluid has been dispensed therefrom.

FIG. 22D is a generally perspective view of the infusion cannula of the device shown in FIG. 22.

FIG. 22E is a generally graphical representation depicting the character of the fluid flow from the dual reservoir apparatus shown in FIG. 22.

FIG. 29 is a cross-sectional view taken along lines 29—29 of FIG. 28.

FIG. 34 is a generally perspective, exploded view of yet another embodiment of the low profile device of the invention partly broken away to show internal construction.

FIG. 34A is a top plan view of the low profile infusion apparatus shown in FIG. 34, partly broken away to show internal construction.

FIG. 35 is a side-elevational view of the apparatus illustrated in FIG. 34.

FIG. 36 is an enlarged, cross-sectional view taken along lines 36—36 of FIG. 35.

FIG. 36A is an enlarged, fragmentary, cross-sectional view taken along lines 36A—36A of FIG. 35.

FIG. 36B is a cross-sectional view taken along lines 36B—36B of FIG. 34A.

FIG. 37 is a greatly enlarged, fragmentary, cross-section view of the area indicated as 37 in FIG. 36B.

FIG. 37A is a generally perspective, exploded view of the serpentine-shaped capillary tube and flow control means of the form of the invention shown in FIGS. 34 through 37.

FIG. 40 is a cross-sectional view taken along lines 40—40 of FIG. 39.

FIG. 40A is a greatly enlarged, fragmentary, cross-sectional view illustrating the construction of the filling subassembly of this embodiment of the invention.

FIG. 41 is a right-side elevational view of the apparatus of FIG. 38.

FIG. 47A is a cross-sectional view taken along lines 47A—47A of FIG. 44.

FIG. 47B is a greatly enlarged, cross-sectional view of the area identified as FIG. 47B in FIG. 47A.

FIG. 47C is a generally perspective, exploded view of the infusion cannula subassembly filter means of this latest form of the invention.

FIG. 48 is a generally perspective, exploded view of the infusion cannula subassembly and filter means of the invention greatly enlarged over the view shown in FIG. 47C and including an exploded view of the filling subassembly of the apparatus.

FIG. 48A is an enlarged, cross-sectional, assembled view of the filling subassembly of the invention.

FIG. 49 is a generally perspective, exploded view of an alternate form of infusion cannula, filter means and filling subassembly of the invention.

FIG. 49A is a fragmentary, generally perspective view of the enlarged diameter end portion of the infusion cannula shown in FIG. 49.

FIG. 50 is a greatly enlarged, cross-sectional view taken along lines 50—50 of FIG. 49A.

FIG. 50A is a cross-sectional view taken along lines 50A—50A of FIG. 50.

FIG. 51 is a generally perspective, exploded view of yet another form of infusion cannula subassembly and filter means of the invention.

FIG. 52 is a cross-sectional view of yet another form of infusion cannula subassembly of the invention.

FIG. 54 is a cross-sectional view taken along lines 54—54 of FIG. 53.

FIG. 55 is a fragmentary, cross-sectional view taken along lines 55—55 of FIG. 54.

FIG. 57 is a cross-sectional view taken along lines 57—57 of FIG. 54.

FIG. 60 is a generally perspective view of the protective sheath portion of the form of the invention shown in FIGS. 53 through 59.

FIG. 61 is a generally perspective, exploded view of still another embodiment of the fluid delivery apparatus of the invention.

FIG. 62 is a top plan view of the embodiment shown in FIG. 61 partially broken away to show internal construction.

FIG. 63 is a cross-sectional view taken along lines 63—63 of FIG. 62.

FIG. 64 is an enlarged cross-sectional view of the area designated by the numeral 64 in FIG. 63.

FIG. 65 is an enlarged, cross-sectional view taken along lines 65—65 of FIG. 62.

FIG. 66 is an enlarged, cross-sectional view taken along lines 66—66 of FIG. 62.

FIG. 67 is a top plan view of the base portion of still another form of the low profile infusion apparatus of the invention partly broken away to show internal construction.

FIG. 69 is a cross-sectional view of the apparatus of FIG. 68 shown in an assembled configuration.

FIG. 70 is an enlarged cross-sectional view taken along lines 70—70 of FIG. 67.

FIG. 71 is a cross-sectional view of the area designated as 71 in FIG. 69.

FIG. 75 is a top plan view of the base portion of still another form of the low profile infusion apparatus of the invention partly broken away to show internal construction.

FIG. 75A is an exploded, cross-sectional view of the form of the invention shown in FIG. 72 illustrating the base portion superimposed over the rate control device, the distendable membrane, and the cover of the apparatus.

FIG. 76 is a cross-sectional view taken along lines 76—76 of FIG. 75.

FIG. 77 is a fragmentary, cross-sectional view of the central portion of the device.

FIG. 77A is a fragmentary, cross-sectional view similar to FIG. 77, but showing fluid being expelled from the fluid reservoir.

FIG. 78 is an enlarged, generally perspective view of one of the filling subassemblies of the form of the invention shown in FIGS. 75 through 76.

FIG. 79 is an enlarged, generally perspective view of cannula assembly of the apparatus of the invention shown in FIGS. 75 and 76.

FIG. 80 is a top plan view of the base portion of still another form of the low profile infusion apparatus of the invention partly broken away to show internal construction.

FIG. 81 is a generally perspective view of the cannula, septum assembly, and fluid outlet assembly of the latest form of the invention.

FIG. 82 is an enlarged, cross-sectional view taken along lines 82—82 of FIG. 80.

FIG. 83 is an exploded, cross-sectional view of the form of the invention shown in FIG. 80 illustrating the base portion superimposed over the rate control device, barrier member, the distendable membrane, and the cover of the apparatus.

FIG. 84 is a generally enlarged, fragmentary, cross-sectional view of the septum assembly of the invention shown in FIG. 83.

FIG. 85 is a greatly enlarged, fragmentary, cross-sectional view of an alternate form of the septum assembly.

FIG. 86 is an enlarged, cross-sectional view of the apparatus of FIG. 83 shown in an assembled configuration.

FIG. 87 is a cross-sectional view similar to FIG. 86, but showing fluid being expelled from the fluid reservoir of the device.

FIG. 88 is a top plan view of the base portion of yet another form of the low profile infusion apparatus of the invention partly broken away to show internal construction.

FIG. 89 is a generally perspective view of the cannula of this latest form of the invention.

FIG. 90 is an enlarged view taken along lines 90—90 of FIG. 88.

FIG. 91 is an exploded, cross-sectional view of the form of the invention shown in FIG. 88 illustrating the base portion superimposed over the rate control device, the first barrier membrane, a second barrier membrane, the distendable membrane, and the cover of the apparatus.

FIG. 92 is an enlarged, generally perspective, exploded view of the fluid outlet subassembly of this latest form of the invention.

FIG. 93 is an enlarged, cross-sectional taken along lines 93—93 of FIG. 88.

FIG. 94 is an enlarged, cross-sectional view similar to FIG. 93, but showing fluid being expelled from the fluid reservoir of the device.

DESCRIPTION OF THE INVENTION

Figure 10:
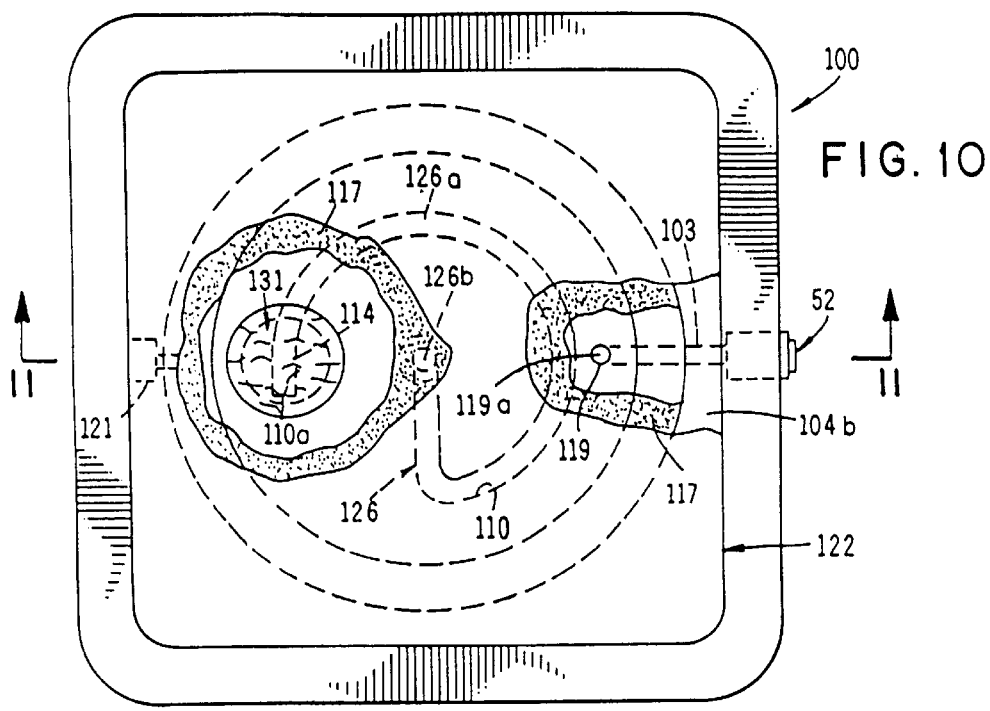
FIG. 10 is a top plan view of the device of FIG. 7 partly broken away to show internal construction.

Referring to the drawings and particularly to FIGS. 1 through 4, one form of the ultra low profile device of the invention for use in intravenous infusion of medicinal fluid into a patient is there shown and generally designated by the numeral 20. As best seen by referring to FIGS. 3 and 4, the embodiment of the invention there shown comprises a thin base 22 having an upper surface 24 including a central portion 24a and peripheral portion 24b circumscribing central portion 24a. Base 22 is provided with a lower surface 26 which is engageable with the patient when the device is taped or otherwise removably affixed to the patient. Formed within base 22 is a circuitous channel 30 (FIGS. 1 and 2), the purpose of which will presently be described.

Forming an important aspect of the apparatus of the present invention is stored energy means for forming in conjunction with base 22 a reservoir 32 having an outlet 34

(FIG. 1) which is superimposed over channel 30 in the manner shown in FIGS. 1 and 2. The stored energy means is here provided in the form of at least one distendable membrane 37 which is superimposed over base 22 and is distendable as a result of pressure imparted by fluids introduced into reservoir 32 through a fluid inlet 39 (FIG. 3). As member 37 is distended, internal stresses will be established within the membrane, which stresses tend to move the membrane toward a less distended configuration and in a direction toward base 22.

Provided within reservoir 32 is ullage defining means for engagement with membrane 37 as the membrane tends to return to its less distended configuration. The ullage defining means in the embodiment of the invention shown in FIGS. 1 through 4 comprises an upstanding, substantially rigid protuberance 40 formed on central portion 24a of base 22. Protuberance 40 is preferably integrally formed with base 22. As membrane 37 returns to toward its original configuration, it will move toward engagement with the upper surfaces of ullage protuberance 40 and in so doing will efficiently force fluid contained within reservoir 32 uniformly outwardly of the device through fluid outlet 34.

Superimposed over the base assembly, which here comprises base 22, protuberance 40 and distendable membrane 37, is a plastic cover, or enclosure 42. For certain applications, cover 42 may be constructed of a porous material and may include venting means shown here as vent "V" (FIG. 2) for venting gases, if any, contained interiorly of the cover. Additionally, medicament and instructions labels can be affixed to cover 42 to identify the medicinal fluid contained within reservoir 32 of the device.

Reference should be made to U.S. Pat. No. 5,169,389 for a discussion of the device labeling and venting and of the various materials that can be used to construct base 22, distendable membrane 37, and cover 42.

A unique aspect of the infusion device of the present invention comprises an infusion means for infusing medicinal fluid from fluid reservoir 32 into the patient. The infusion means here comprises a circuitously shaped hollow cannula 46 having a body portion 46a which is disposed within circuitous channel 30 formed in base 22 and an outlet end 46b here provided in the form of a pierceable portion which extends outwardly from base 22 for insertion into the vein of a patient. For this purpose, pierceable portion 46b includes a sharp, needle-like extremity 47 which is configured in generally the same fashion as a conventional intravenous infusion needle.

In the form of the invention shown in FIGS. 1 through 4, pierceable portion 46b of the cannula extends outwardly from base 22 in a direction generally parallel to lower surface 26 of base 22. With this unique construction, the device can be affixed to the patient's body as, for example, the arms or legs in any convenient manner, with the pierceable needle portion of the device penetrating the patient's vein. Medicinal fluid contained within reservoir 32 can then be dispensed through the cannula by means of the stored energy provided by membrane 37 which is released as the membrane tends to return toward a less distended configuration and into engagement with the ullage defining means or protuberance 40.

Forming a part of the proximal portion of the device is a protective sheath 49 for encapsulating and protecting pierceable portion 46b of the cannula. This assembly also includes web means for further assisting in securing and maintaining the penetrable portion in an appropriate invasive position to preclude intravascular trauma. Web means is here provided as a soft, flexible butterfly assemblage 49a (FIGS. 1 and 2), which is connected to base 22 and provides an appropriate surface area for taping the device to the patient.

As best seen by referring to FIGS. 3 and 4B, body portion 46a of cannula 46 is provided with a fluid inlet 46c which communicates with the outlet 34 of reservoir 32 so that fluid can flow from the reservoir into inlet 46c through cannula 46 and outwardly thereof through pierceable portion 46b.

Filling of reservoir 32 with a selected beneficial agent, or medicinal fluid, is accomplished by filling means which here comprises a septum assembly 52 which is connected to base 22 in the manner shown in FIGS. 1 and 2. Septum assembly 52 includes a pierceable septum 54 and a fill conduit 56 which communicates with cannula 46 and fluid inlet 39. As shown in FIG. 3, inlet 39, in turn, communicates with a fill orifice 58 provided in top surface 24 of base 22. With this construction, medicinal fluid can be introduced into reservoir 32 using a conventional syringe. Alternatively, the fill means can comprise a luer fitting or any other suitable fluid interconnection of a character well known to those skilled in the art by which fluid can be controllably introduced into reservoir 32 to cause distendable membrane 37 to move into its distended configuration as shown in FIGS. 3 and 4. Once again, reference should be made to U.S. Pat. No. 5,169,389 for a more complete discussion of the construction and operation of the reservoir filling means.

Forming another very important aspect of the apparatus of the present invention is fluid flow control means which is supported by base 22 at a location proximate the first end of circuitous channel 30. The fluid flow control means functions to control fluid flowing from reservoir 32 into cannula 46 and outwardly through pierceable portion 46b of the cannula. This fluid flow control means here comprises a porous member 51 which is received within a cavity 53 formed in base 22. Member 51 can be constructed of various materials such as a porous polycarbonate material available from Corning Costar Corporation and like suppliers.

Turning now to FIGS. 5 and 6, it is to be observed that the circuitously shaped cannula can be constructed in a number of different configurations including those shown in FIGS. 5 and 6. The cannula shown in FIG. 5 and generally designated as 55 has a generally Z-shaped body portion, while the cannula shown in FIG. 6 and generally designated by the numeral 57 comprises a body portion 57a which is vertically offset from the penetrable portion 57b. Depending upon the end use of the device and the configuration of base 22, cannulas having configurations such as those shown in FIGS. 5 and 6 can be appropriately positioned within corresponding circuitously shaped channels formed in base 22.

Referring next to FIGS. 7 through 14, an alternate form of the ultra low profile device of the invention is there shown and generally designated by the numeral 100. As best seen by referring to FIGS. 7, 9, and 11, the embodiment of the invention is similar in some respects to that shown in FIGS. 1 through 7. Accordingly, like numbers are used to identify like components. The apparatus here comprises a thin base 102 (FIG. 9) having an upper surface 104 including a central portion 104a and peripheral portion 104b circumscribing central portion 104a. Base 102 is provided with a lower surface 106 to which a padded assembly 107 is connected. Assembly 107 comprises a foam pad 107a to which an adhesive layer 107b is annexed. When the device is used, a very thin peal strip 107c can be stripped away so that the device can be releasably affixed to the patient. Formed within base 104 is a circuitous channel 110 (FIGS. 11 and 12), the purpose of which will presently be described.

Figure 11:
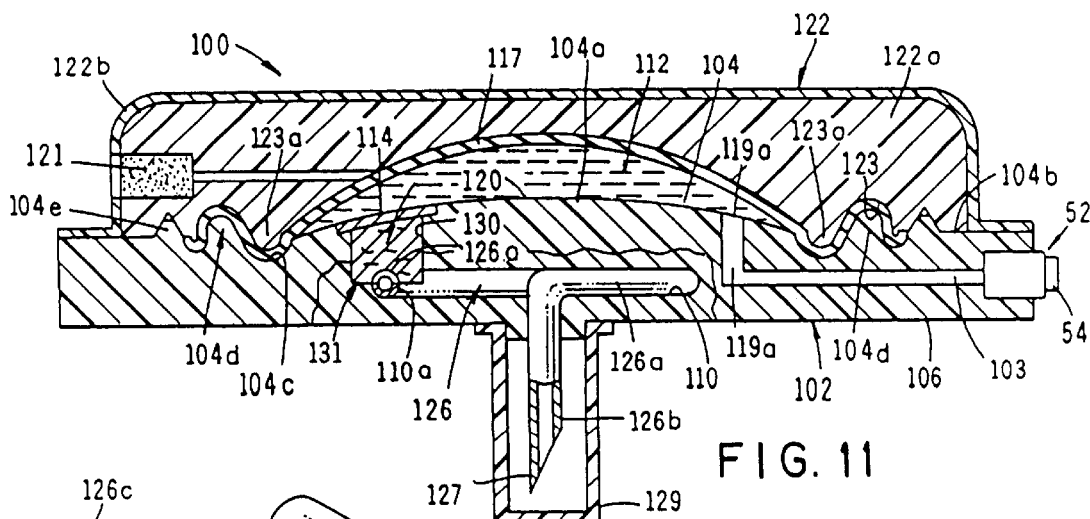
FIG. 11 is a cross-sectional view taken along lines 11—11 of FIG. 10.
Figure 12:
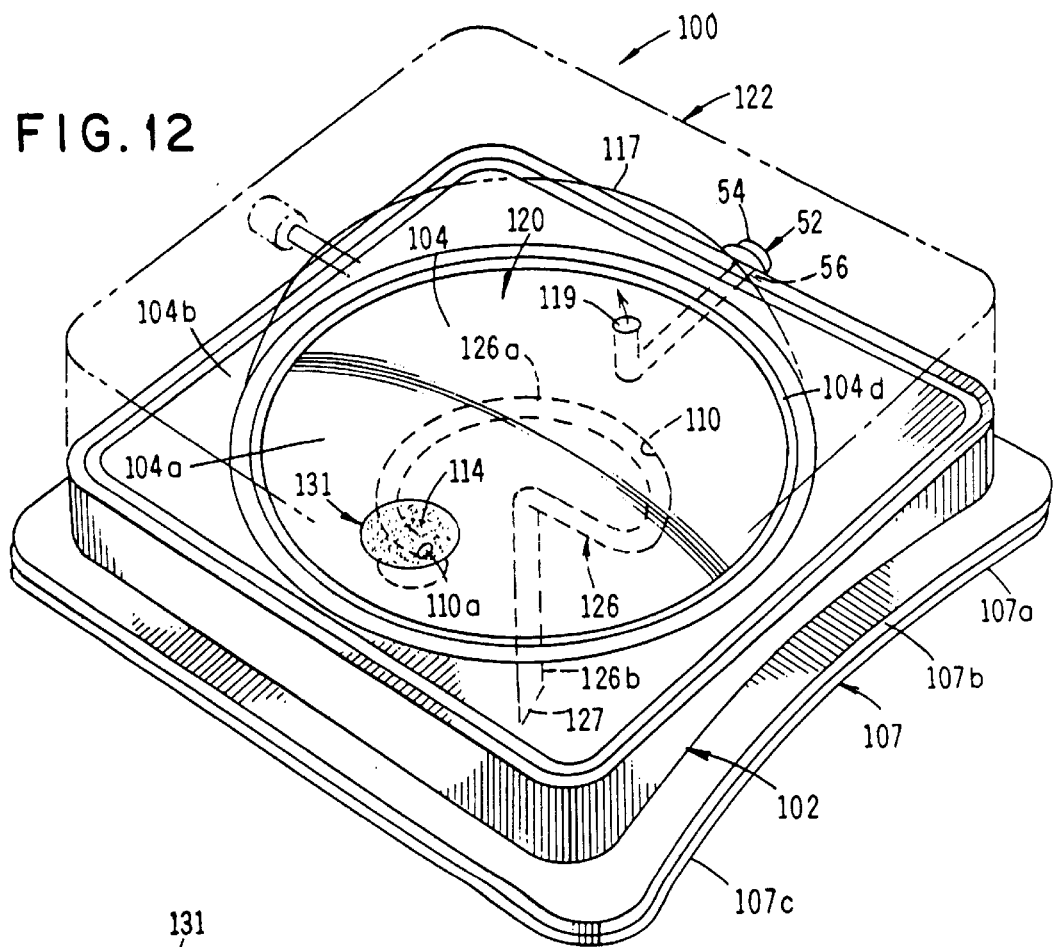
FIG. 12 is an enlarged, generally perspective view of a portion of the device shown in FIG. 7.

In the previously described embodiment, the apparatus shown in FIGS. 7 through 14 also includes stored energy means for forming in conjunction with base 102 a reservoir 112 having an outlet 114 (FIG. 12) which is superimposed over channel 110 in the manner shown in FIGS. 11 and 12. The stored energy means is here provided in the form of at least one distendable membrane 117 which is superimposed over base 102. Membrane 117 is distendable as a result of pressure imparted on the membrane by fluids introduced into reservoir 112 through a fluid inlet 119 (FIG. 11). As member 117 is distended internal stresses will be established, which stresses tend to move the membrane toward a less distended configuration and in a direction toward base 102.

Provided within reservoir 112 is ullage defining means for engagement with membrane 117 as the membrane tends to return to its less distended configuration. The ullage defining means in the embodiment of the invention shown in FIGS. 7 through 12 comprises an upstanding protuberance 120 formed on central portion 104a of base 102. As membrane 117 returns to toward its original configuration, it will move toward engagement with the upper surfaces of ullage protuberance 120 and in so doing will efficiently force fluid contained within reservoir 112 uniformly outwardly of the device through fluid outlet 114.

Superimposed over the base assembly is a plastic cover, or enclosure 122. Cover 122 includes a body portion 122a and an outer covering 122b, venting means for venting gases, if any, contained interiorly of the cover. This venting means here comprises a porous vent member 121 provided in cover 122 (FIG. 11). As before, medicament and instructions labels "L" can be affixed to cover 122 to identify the medicinal fluid contained within reservoir 112 of the device.

Once again, reference should be made to U.S. Pat. No. 5,169,389 for a discussion of the various materials that can be used to construct base 102, distendable membrane 117, and cover 122.

A unique aspect of the infusion device shown in FIGS. 7 through 14 comprises an infusion means for infusing medicinal fluid from fluid reservoir 112 into the patient. The infusion means here comprises a circuitously shaped hollow cannula 126 having a body portion 126a which is disposed within circuitous channel 110 formed in base 102 and an outlet end 126b here provided in the form of a pierceable portion extending generally perpendicularly downward from base 102 for subdermal infusion of medicinal fluids into the patient. For this purpose, pierceable portion 126a includes a sharp needle-like portion 127 which is configured in generally the same fashion as a conventional infusion needle. Unlike the earlier described embodiment of the invention, pierceable portion 126b of the cannula of the present embodiment extends outwardly from base 102 in a direction generally perpendicularly to lower surface 106 of base 102. With this unique construction, the device can be affixed to the patient's body, such as the arms or legs, in any convenient manner with the pierceable needle portion of the device penetrating the skin. Medicinal fluid contained within reservoir 112 can then be subdermally injected into the patient as membrane 117 tends to return toward a less distended configuration and into engagement with the ullage means or protuberance 120. Forming a part of the proximal portion of the device is a protective sheath 129 for encapsulating and protecting pierceable portion 126b of the cannula.

Figure 13:
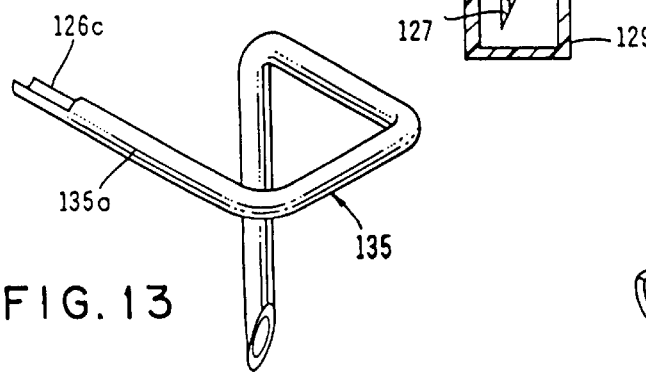
FIG. 13 is a generally perspective view of an alternate form of infusion cannula of the invention.
Figure 14:
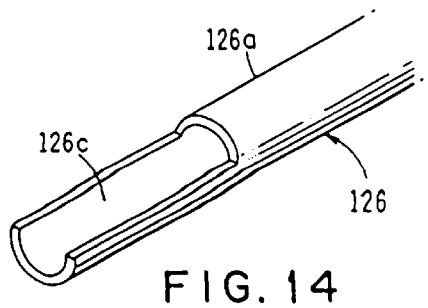
FIG. 14 is an enlarged, generally perspective view of the fluid inlet end of the infusion cannula.

As best seen in FIGS. 13 and 14, body portion 126a of cannula 126 is provided with a fluid inlet 126c which communicates with outlet 114 of reservoir 112 so that fluid can flow from the reservoir into inlet 126c and then in cannula body 126a via a fluid flow control means mounted within a cavity 130 formed in base 102.

Figure 15:
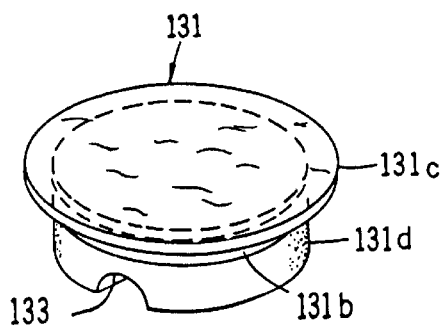
FIG. 15 is a greatly enlarged, generally perspective top view of one form of the fluid flow control assembly of the invention.
Figure 16:
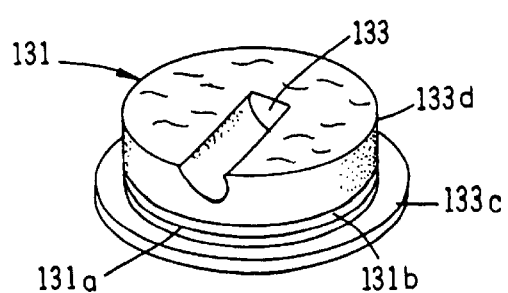
FIG. 16 is a greatly enlarged generally perspective, bottom view of the flow control assembly.
Figure 17:
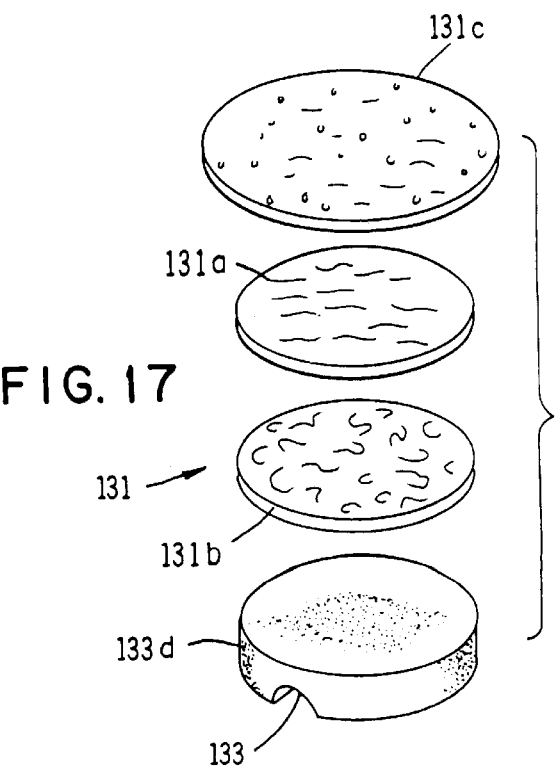
FIG. 17 is a generally perspective, exploded view of the flow control assembly of the invention of FIGS. 15 and 16.

The fluid flow control means of this latest form of the invention functions to control fluid flowing from reservoir 112 into cannula 126 and then outwardly through pierceable portion 126b of the cannula. Turning to FIGS. 15, 16, and 17, the flow control means of this latest form of the invention can be seen to comprise an assemblage of the general configuration shown in FIGS. 15 and 16 which assemblage is receivable within a cavity 130 formed in base 102 (FIG. 11). This fluid flow control assemblage, which is generally designated by the numeral 131, is of a laminate construction comprising filtering means for filtering the fluid flowing outwardly of reservoir 112 and rate control means for controlling the rate of fluid flow from reservoir 112 into cannula 126. Referring to FIG. 17, it can be seen that the filter means here comprises a filter element 131a while the rate control element comprises a disk-like rate control element 131b. Superimposed over filter element 131a is a porous disk-like seal member 131c. The assemblage comprising filter element 131a, rate control element 131b, and porous seal 131c is supported by a porous base substrate 131d having a semi-circular shaped cavity 133 which is adapted to closely receive the first end portion of cannula 126. Filter element 131a can be constructed from a wide variety materials. However, a material comprising polysulfone sold by Gelman Sciences under the name and style of SUPOR has proven satisfactory. Rate control element 131b is preferably constructed from a polycarbonate material having extremely small flow apertures ablatively drilled by an excimer laser ablation process. Both the orifice size and unit distribution can be closely controlled by this process. However, a number of other materials can be used to construct this element. Porous substrate 131d can similarly be constructed from various materials such as a porous polypropylene available from Gelman Sciences.

Turning to FIGS. 12, 13, and 14, it is to be observed that the circuitously shaped cannula can be constructed in a number of different configurations. For example, the cannula shown in FIG. 12 has a generally semi-circular shaped body portion 126a while the cannula 135 shown in FIG. 13 has a generally U-shaped body portion 135a. Both cannula construction as shown in FIGS. 12 and 13 include an inlet portion of the character shown in FIG. 14. The generally trough-shaped inlet portion 126c is disposed proximate first end 110a of channel 110 and, as shown in FIG. 11, is located directly below flow control assembly 131 so that fluid flowing through the flow control assembly will feed directly into cannula 126.

Filling of reservoir 112 with a selected beneficial agent, or medicinal fluid, is accomplished by filling means which here comprises a septum assembly 52 of the character previously described. Septum assembly 52 is connected to base 102 in the manner shown in FIGS. 10 and 11. Septum assembly 52 includes a pierceably septum 54 and a fill conduit 103 which communicates with cannula 46 and fluid inlet 119, which, in turn, communicates with fill orifice 119a provided in base 102 (FIG. 11). With this construction, medicinal fluid can be introduced into reservoir 112 using a conventional syringe.

Figure 12A:
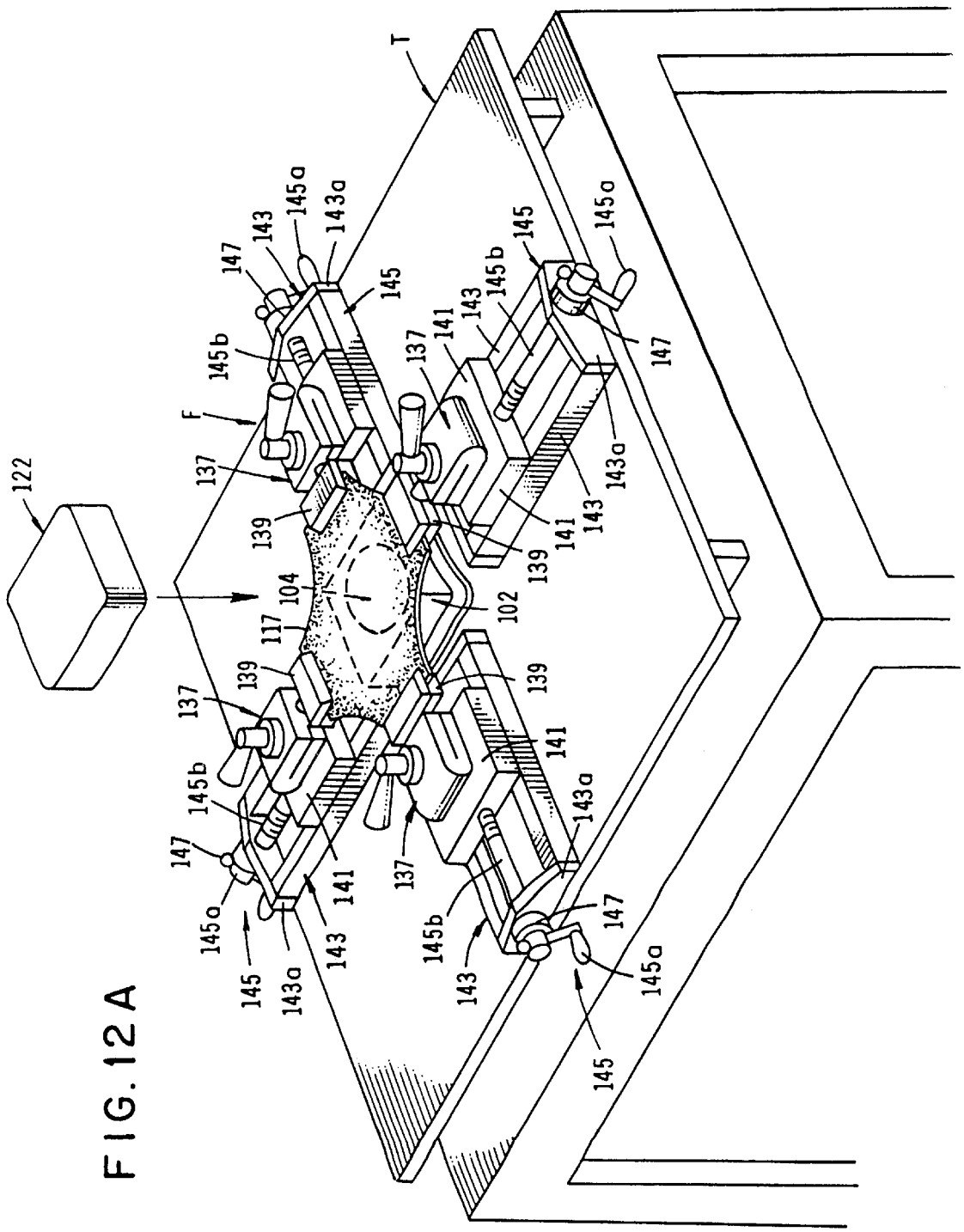
FIG. 12A is a generally perspective view illustrating the membrane biaxial stretching step of the method of the invention.

Referring next to FIG. 12A, an apparatus for use in accomplishing the method of the invention is there illustrated. In accordance with the method of the invention for constructing the fluid delivery device, base 102 is positioned on a table "T" upon which membrane stretching means is affixed. The membrane stretching means here provided as a stretching, or elongation fixture "F", functions to bilaterally stretch the membrane in the manner shown in FIG. 12A to controllably prestress the membrane. Stretching fixture "F" comprises four circumferentially spaced membrane holding clamps 137 each having gripping elements 139 for gripping the edges of the isotropic membrane 117. Each of the clamps 137 is affixed to slide block 141 which is slidably movable along a pair of table mounted tracks 143 by means of a screw assembly 145 which is carried by an end plate 143a provided on each track 143. Each screw assembly comprises a threaded rod 145b one end of which is connected to a slide block 141. As the screw assembly is rotated by means of a handle 145a, the slide block, along with its associated clamp 137 will move outwardly relative to stationary base 102. A manual vernier 147 provided on each screw assembly provides an indication of the extent of movement of the slide block. By controlled outward movement of the slide blocks in the manner shown in FIG. 12A, the isotopic membrane will be controllably stretched and prestressed to the desired extent.

Turning to FIG. 12B, another type of apparatus usable in carrying out the method of the invention is there illustrated. This apparatus also includes a membrane stretching fixture "SF" which functions to controllably bilaterally stretch the elastomeric membrane 117 in the manner illustrated in FIG. 12B. Stretching fixture "SF" includes a plurality of circumferentially spaced hydraulically actuated membrane gripping assemblies 149, each having gripping elements for gripping the edges of the isotropic membrane. Each of the gripping assemblies 149 is mounted on a support table "T", which also supports the hydraulic equipment for operating assemblies 149. This type of equipment is of a character well known to those skilled in the art. As the gripping assemblies are actuated following a predetermined extension protocol, the gripping elements will move radially outwardly relative to the center of membrane 117 causing it to stretch either uniformly or non-uniformly depending on the end use of the device. It is to be understood that for certain end use applications of the apparatus, the stored energy membrane need not be prestressed.

Also forming a part of the apparatus of FIG. 12A is a centrally disposed sonic welding apparatus "SW", which can be used in a manner well known by those skilled in the art to interconnect cover assembly 122 to base 102. Surrounding the sonic welder are vacuum operated article pick-up devices "PU", which can be used to position the cover assembly of the fluid delivery device relative to the membrane during the assembly operation. Each of these pick-up devices includes a generally circular shaped gripping member 151 which is rotatable about a support shaft 151a.

After the membrane has been appropriately prestressed, the next step in the method of the invention comprises affixing the prestressed membrane to the peripheral portion 104b of the upper surface of base 102. This is accomplished by moving cover assembly 122 downwardly relative to base 102 in a manner such that prestressed membrane 117 will be securely clamped between the peripheral portions of cover 122 and the peripheral portion of the base (see FIGS. 9 and 11). As the cover is moved toward base 102, the central portion of membrane 117 will engage and conform to the ullage defining means or protuberance 104.

Cover 122 as well as membrane 117 can be interconnected with the base as by sealably bonding them to the base 102 in various ways well known to those skilled in the art, such as, for example, adhesive or sonic bonding. In the embodiment of the invention shown in FIGS. 9 and 11, peripheral portion 104b of base 102 is provided with a capture groove 104c and an adjacent tongue 104d. Body portion 122a of assembly cover 122, on the other hand, is provided with a groove 123 and a tongue 123a (FIG. 11) which mate with groove 104c and tongue 104d respectively as the cover moves into engagement with base 102. Base 102 is further provided with an upstanding membrane cutting means or protuberance 104e (FIG. 11) which functions to cleanly cut membrane 117 upon cover 122 being brought into pressural engagement with base 102. With this construction, following cutting of the membrane the cover can be sonically welded to the base in the proximity of the upstanding tongue of the base and the mating groove in the cover by techniques well understood by those skilled in the art. After the sonic welding step, the cover and membrane are securely interconnected with the base in a manner to provide a sealed enclosure for the distendable membrane.

Figure 20:
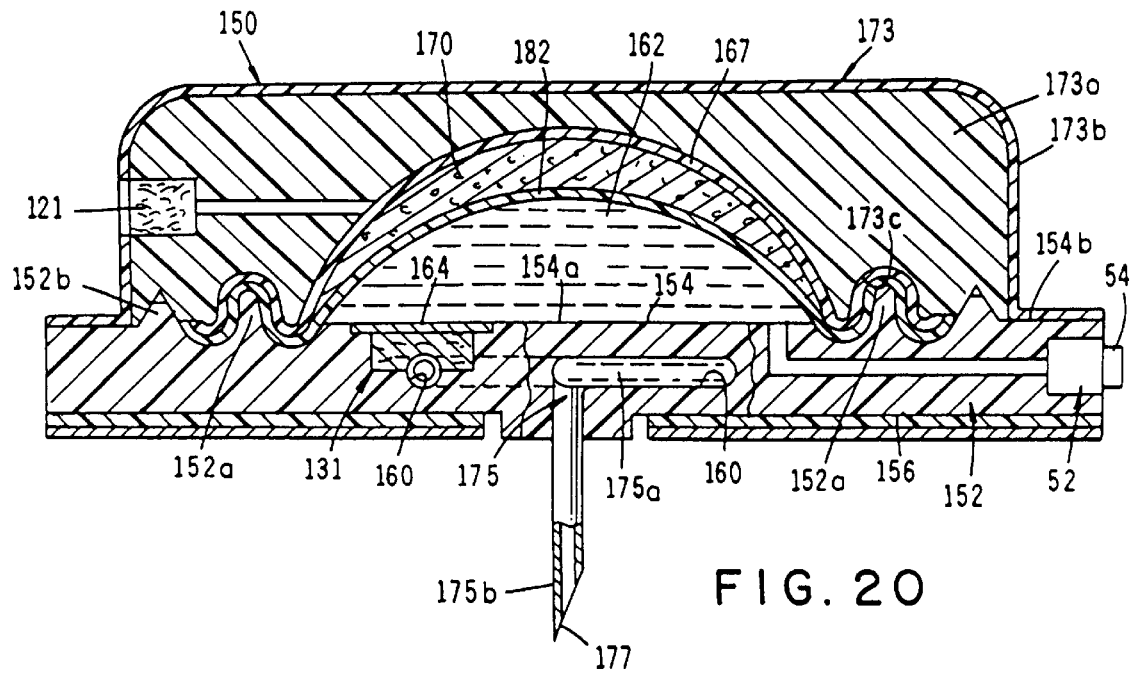
FIG. 20 is a cross-sectional view of yet another embodiment of the invention showing an infusion device embodying a novel conformable ullage rather than rigid ullage.

Referring to FIGS. 20 and 21, still another form of the ultra low profile device of the invention is there shown and generally designated by the numeral 150. As best seen by referring to FIG. 20, this latest embodiment of the invention is similar in some respects to that shown in FIGS. 7 through 12. Accordingly, like numbers are used to identify like components. The apparatus here comprises a base 152 having an upper surface 154, including a central portion 154a and peripheral portion 154b circumscribing central portion 154a. Base 152 is also provided with a lower surface 156. Formed within base 152 is a circuitous channel 160, which receives the infusion means of the invention.

As in the previously described embodiments, the apparatus shown in FIGS. 20 and 21 also includes stored energy means for forming in conjunction with base 152 a reservoir 162 having an outlet 164. Outlet 164 is superimposed over channel 160 in the manner shown in FIG. 20. Filling of reservoir 162 is accomplished in the same manner as previously described herein in connection with the embodiment shown in FIGS. 7 through 12 using septum assembly 52.

The stored energy means is here provided in the form of at least one distendable membrane 167 which is superimposed over base 152. As before, an ullage defining means is disposed within reservoir for engagement with membrane 167 which, after being distended, will tend to return to its less distended configuration. The ullage defining means of this latest embodiment of the invention is of a totally different and highly novel character from that previously described. More particularly, the ullage defining means here comprises a conformable ullage which uniquely conforms to the shape of the distendable membrane, as the membrane tends to return to its less distended configuration in the manner shown in FIG. 20A. The conformable ullage, which is identified in FIGS. 20 and 20A by the numeral 170, can be constructed as a deformable mass from a number of materials such as various types of gels, foams, fluids and soft elastomers. In some instances the conformable ullage may comprise an integral conforming mass. In other instances, such as when a gel or fluid is used as the ullage medium, an encapsulation barrier membrane is used to encapsulate the ullage medium.

A highly novel aspect of the conformable ullage of the invention resides in the fact that it can be located either between the base and the fluid to be delivered or, alternatively, as shown in FIG. 20, can be located between the distendable membrane and the fluid to be delivered. Additionally, as will be discussed in the paragraphs which follow, a plurality of subreservoirs can be associated with a single ullage thereby making it possible to provide a wide variety of different medicament delivery regimens.

Because the ullage defining means can be located in various locations within the reservoir, the central portion of the base is, as shown in FIG. 21, substantially flat. This type of base can, of course, be used with an ullage configuration of the character shown in FIG. 20 and can also be used with a variety of different ullage configurations, the details of which will presently be described.

Figure 18:
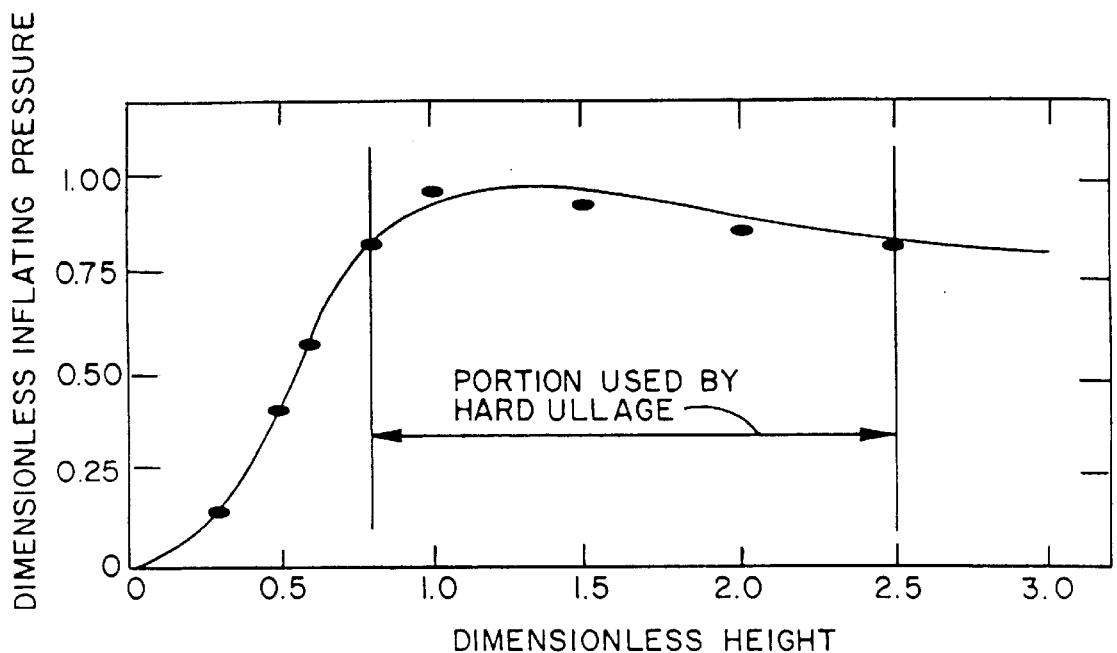
FIG. 18 is a graphical representation of the range of extension of the distendable membrane in a rigid ullage type of construction.

Before discussing the number of conformable ullage configurations that are possible in constructing the fluid delivery devices of the invention, a brief discussion will be undertaken of the several operational advantages that are inherent in the conformable ullage construction. For example, the rigid ullage construction, such as is shown in FIGS. 1 through 14, requires that the stored energy elastomeric membrane be used at high extensions over a significantly large pressure curve. This condition is illustrated in FIG. 18 wherein inflating pressure is plotted against height. Further, the elastomeric membrane materials that are suitable for use as the stored energy means must possess certain specific physical characteristics in order to meet the performance requirements for the fluid delivery apparatus. For example, depending on the end use of the device, the elastomeric membrane material must have good memory characteristics under conditions of high extension, good resistance to chemical and radiological degradation and appropriate gas permeation characteristics.

Once an elastomeric membrane material is chosen that will optimally meet the desired performance requirements of the fluid delivery device, there are still limitations to the level of refinement of the delivery tolerances that can be achieved using the rigid ullage configuration. These refinements are due primarily to the inability of the rigid ullage to satisfactorily conform to the shape of the elastomeric membrane near the end of the fluid delivery cycle. This nonconformity can lead to extended delivery rate tail off and higher residual problems that are undesirable when extremely accurate delivery is required. For example, when larger volumes of fluid are to be delivered, the tail-off volume represents a smaller portion of the fluid amount delivered and, therefore, exhibits much less effect on the total fluid delivery profile. However, in very small dosages, the tail-off volume becomes a larger portion of the total volume. This places physical limits on the range of delivery profiles that can acceptably be accommodated by the rigid ullage configuration.

The elastomeric membrane material candidates for use in the rigid ullage construction must also be drug compatible since the membrane will typically be in contact with the drug containing fluid that is introduced into the reservoir. Many currently available elastomeric membrane materials, due to their chemical composition or means of manufacturing, are not suitably drug compatible. This compatibility restriction, combined with strict physical requirements and material properties characteristics, results in further limitation of available selections for the candidate elastomeric material for use in the rigid ullage design.

The apparatus of the invention illustrated in FIG. 20 provides a unique and novel improvement over the rigid ullage type devices and, as will become apparent from the discussion which follows, can be adapted to many end use applications. More particularly, this novel embodiment of the invention includes the previously identified conformable ullage 170 that can be constructed of various materials that will elegantly satisfy the tighter delivery tolerance requirements of the device, while at the same time effectively overcome the limitations of materials selection encountered in devices embodying the rigid ullage configuration.

Figure 19:
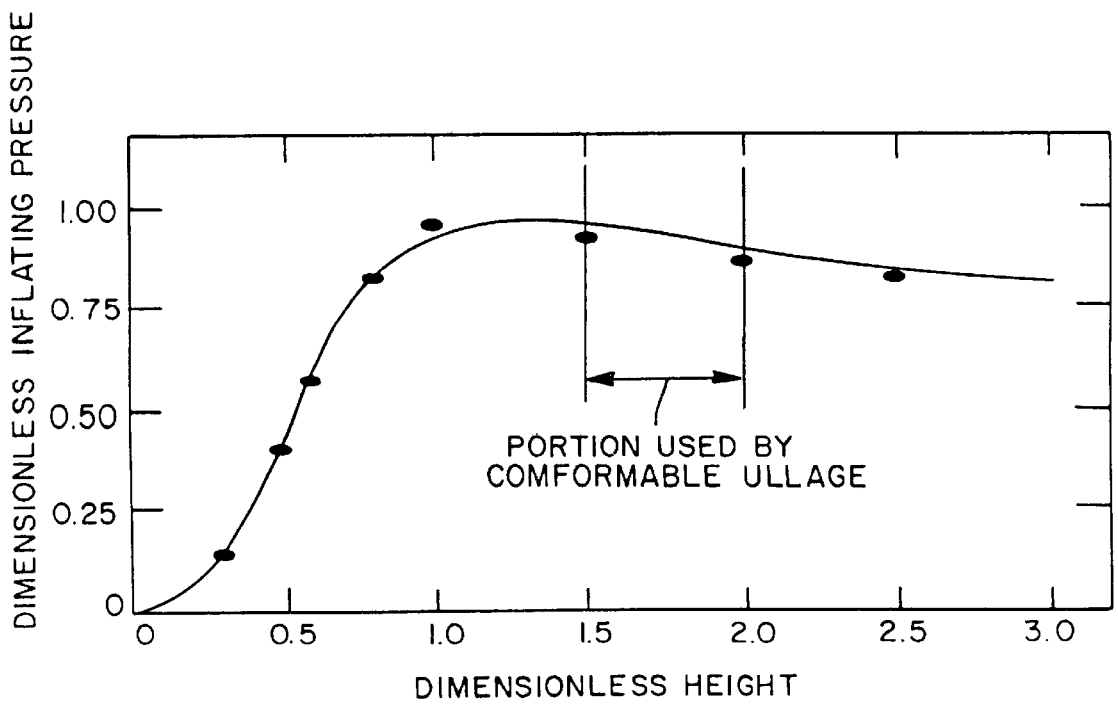
FIG. 19 is a graphical representation of the range of extension of the distendable membrane in a conformable ullage type of construction.

As previously mentioned, the unique characteristics of the conformable ullage of this latest form of the invention permits the ullage to be placed either above or below the fluid reservoir in relation to the base. For example, when, as indicated in FIG. 19, the conformable ullage is positioned above the medicament reservoir, a much smaller portion of the pressure-deformation curve can be used, thus enabling the stored energy membrane to undergo less deformation during the fluid delivery process. Less deformation of the stored energy membrane, in turn, minimizes the changes in the linearity of the resulting fluid delivery profile. Further, because the small portion of the pressure-deformation curve that is used can be taken from a lower elongation level (FIG. 19), the viscoelastic effect is reduced. The viscoelastic effect reduces the level of stored energy in the membrane over time, which translates into lower rates of energy membrane stress relaxation over time. This is a most important performance design factor for devices requiring prolonged shelf life having extended delivery profiles.

Referring once again to FIG. 20, in the construction of the device there shown, a cover assembly 173 is superimposed over base 152. Cover assembly 173 includes a body portion 173a, an outer covering 173b, and venting means comprising a porous vent member 121 of the character previously described. This latest form of the invention also includes an infusion means for infusing medicinal fluids from fluid reservoir 162 in the patient. The infusion means comprises a circuitously shaped hollow cannula 175 of the character previously described having a body portion 175a which is disposed within circuitous channel 160 formed in base 152 and an outlet end 175b here provided in the form of a pierceable portion extending generally perpendicularly downward from base 152 for subdermal infusion of medicinal fluids into the patient. For this purpose, pierceable portion 175b includes a sharp, needle-like portion 177. Forming a part of the proximal portion of the device is a protective sheath 179 for encapsulating and protecting pierceable portion 175b of the cannula (FIG. 21).

During the step of filling reservoir 162, which is accomplished in the manner previously described, the fluid being introduced into the reservoir under pressure via septum assembly 52 will cause a pusher member 182, which is affixed proximate its periphery to base 152, to engage conformable ullage 170 urging it outwardly against distendable membrane 167. As the membrane is thus distended, internal stresses will be formed in the membrane tending to return it to the less distended configuration shown in FIG. 20A. As this occurs membrane 167 will exert forces on conformable ullage 170 which will controllably move it toward base 152. However, when ullage 170 engages base 152, in the manner shown in FIG. 20A, it will uniquely conform to the upper surface of the base as well as the three dimensional shape of distendable membrane 167. In this way, the conformable ullage will permit the distendable membrane to provide a constant fluid expelling pressure on the fluid contained within the reservoir throughout the fluid delivery cycle, thereby avoiding undesirable delivery rate tail off at the end of the delivery period. This novel linear performance permits the device to meet even the most stringent medicinal fluid delivery requirements.

During the fluid delivery step described in the preceding paragraph, fluid will flow from reservoir 162, through outlet 164, through a flow control means and into the inlet through 175c of cannula 175 (FIG. 21a). The flow control means here comprises a flow control assembly 131 of the character shown in FIGS. 15, 16, and 17 and as previously described herein.

Figure 20A:
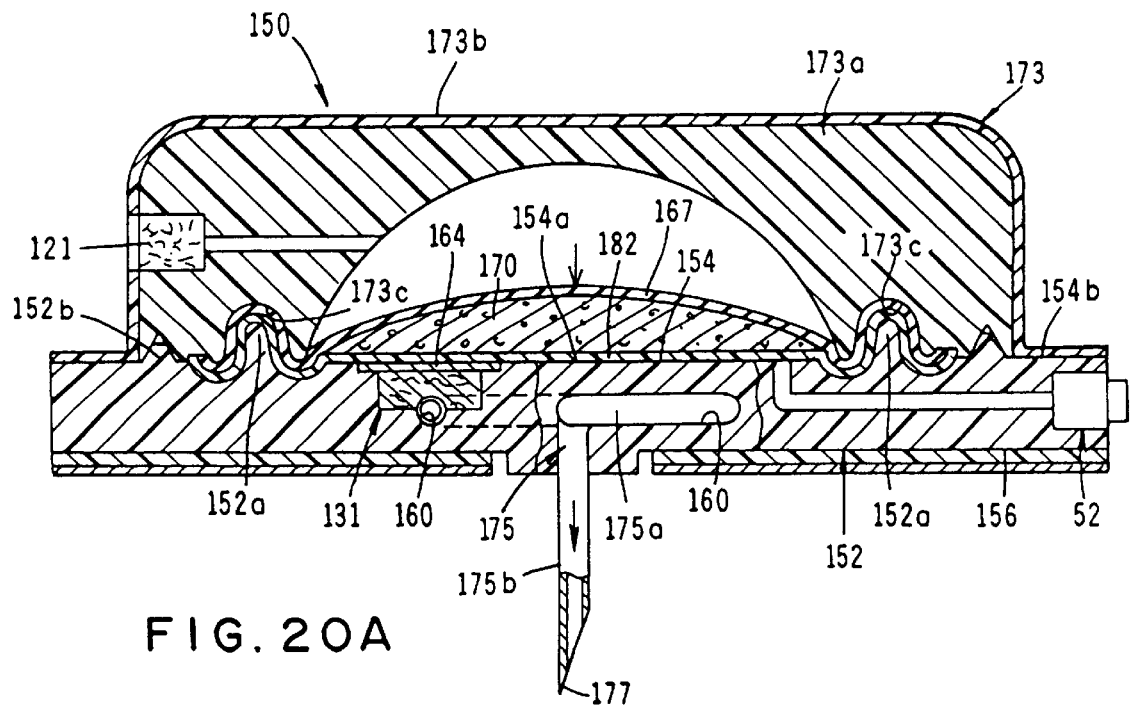
FIG. 20A is a cross-sectional view similar to FIG. 20, but showing the configuration of the device after the fluid has been dispensed therefrom.

Distendable membrane along with pusher member 182 are secured to base 152 in the manner shown in FIG. 20A.

More particularly, the peripheral portion 154b of base 152 is provided with a tongue 152a which mates with a groove 173c provided in cover assembly 173 as the cover assembly moves into engagement with base 152. Base 152 is also provided with an upstanding, circumferentially extending membrane cutting means or protuberance 152b (FIG. 11) which functions to cleanly cut membrane 167 and pusher 182 upon cover assembly 173 being brought into pressural engagement with base 152. Protuberance 152b also functions as a sonic energy director for the sonic weldment of base 152 and cover 173. With this construction, following cutting of the membrane and the pusher member, the cover can be sonically welded to the base in the proximity of the upstanding tongue of the base and the mating groove in the cover by techniques well understood by those skilled in the art. After the sonic welding step, the cover, membrane, and pusher member are all securely interconnected with the base in a manner to provide a sealed enclosure.

Turning to FIG. 22, still a further form of the ultra low profile device of the invention is there illustrated and generally designated by the numeral 200. This embodiment of the invention is similar in some respects to that shown in FIGS. 20 and 21 and, therefore, like numbers are used in FIG. 22 to identify like components. This apparatus is unique in that it includes two separate fluid containing reservoirs and a conformable ullage disposed between the reservoirs and the stored energy means. As before, the apparatus comprises a thin base 202 having an upper surface 204 including a generally planar central portion 204a and a peripheral portion 204b circumscribing the central portion. Formed within base 202 is a circuitous channel 206 that receives a circuitously shaped cannula 208.

The apparatus shown in FIG. 22 also includes stored energy means for forming in conjunction with base 202 first and second reservoirs 210 and 212. Reservoir 212 has an outlet 214 while reservoir 210 has an outlet 216 both of which are superimposed over a circuitous channel 206. Both reservoirs communicate with cannula 208 via flow control means here shown as first and second flow control assemblies 218 and 220. The stored energy means is here provided in the form of at least one distendable membrane 224 which is superimposed over base 202 and is affixed therewith in the manner shown in FIG. 22 and as described in connection with the earlier discussed embodiments.

As was the case with the embodiment of the invention shown in FIGS. 20 and 21, pierceable portion 208b of the cannula extends outwardly from base 202 in a direction generally perpendicularly to lower surface of the base. With this construction, medicinal fluids contained within reservoirs 210 and 212 can then be subdermally injected into the patient as membrane 224 tends to return toward the less distended configuration shown in FIG. 22C and into engagement with the ullage means or a conformable ullage 225 which is of similar construction to conformable ullage 170. As shown in FIG. 22E, this arrangement of reservoirs results in a two phase flow rate delivery profile. Initially, the injection flow rate results from the medicinal fluid flowing from both reservoirs 210 (R1) and 212 (R2). In the latter portion of the flow delivery profile, and after the fluid in reservoir 212 is expanded, only the remaining medicinal fluid in reservoir 210 contributes to the flow. The greater flow rate in the first phase is intended to accommodate periods where a higher dosage rate is required, such as the basal delivery rate for insulin during the daytime. The second phase with its lower flow rate is then suitable for the basal rate delivery of insulin during the night when less is required. In this manner, one delivery apparatus may be used for an entire 24 hour period.

As indicated in FIG. 22D, body portion 208a of cannula 208 is provided with a first fluid inlet 226 which communicates with outlet 216 of reservoir 210 so that fluid can flow from this reservoir into the flow control assembly 218 and then in cannula 208. In similar fashion, reservoir 212 communicates with a second fluid inlet 228 provided in cannula 208 via outlet 214 and flow control assembly 220. Flow control assemblies 218 and 220 are of identical construction to the assemblage shown in FIGS. 15, 16, and 17 and operate in the same manner to control fluid flow from the two reservoirs outwardly into cannula 208 shown in FIG. 22. A cover assembly 225 covers base 202 in the manner shown in FIG. 22.

During the filling step, reservoir 212 is first filled by fluid introduced into a passageway 228 (FIG. 22) via a first septum assembly 51 which is provided in base 202 in a spaced apart relationship with a second septum assembly 52. Fluid under pressure flowing through passageway 228 will engage a pusher membrane 230 which is affixed at its peripheral upper surface 204 of base 202. Following filling of reservoir 212, reservoir 210 is next filled using the second septum assembly 52 which is in fluid communication with a passageway 229 formed in base 202. As fluid under pressure enters reservoir 210 via passageway 229, conformable ullage 225 will be urged outwardly against distendable membrane 224 causing the membrane to move outwardly against the inner surface 225a of cover assembly 225. As the membrane is thus distended, internal stresses will be formed within the membrane.

Upon opening the outlet or delivery port of the device, the distended membrane 224 will exert forces on conformable ullage 225 which will controllably move it toward base 202 in the manner shown in FIG. 22C. As before, during the infusion step, the ullage will uniquely conform to the three dimensional shape of the distendable membrane and fluid contained within reservoir 210 and 212 will be controllably expelled from the device. During the infusion step the, distendable membrane functions to provide a constant, uniform pressure on the fluid within the two reservoirs thereby avoiding any undesirable delivery rate tail off near the end of the delivery period.

Figure 23:
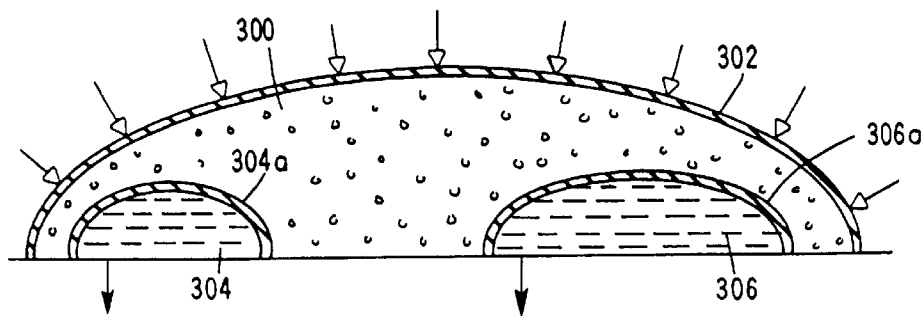
FIG. 23 is a generally diagrammatic view of yet another form of conformable ullage construction of the invention showing two fluid filled subreservoirs.
Figure 24:
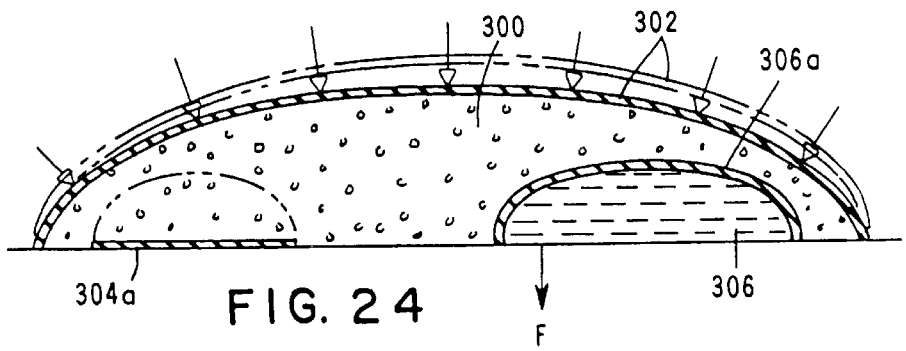
FIG. 24 is a generally diagrammatic view similar to FIG. 23, but showing one of the subreservoirs having been emptied of fluid.
Figure 25:
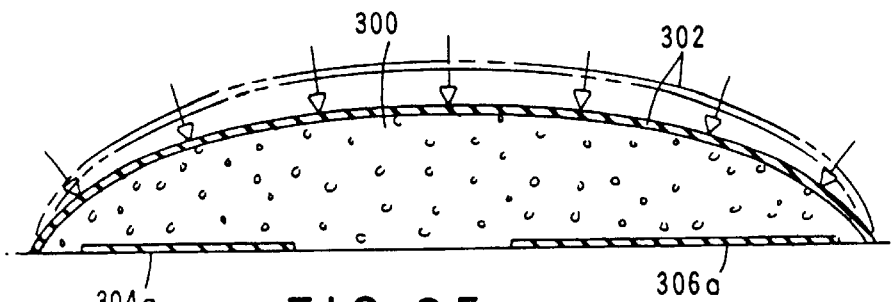
FIG. 25 is a generally diagrammatic view similar to FIG. 24 but, showing both of the subreservoirs having been emptied.

Turning next to FIGS. 23, 24, and 25, yet another conformable ullage, distendable membrane and reservoir only construction is there diagrammatically illustrated. In this instance the conformable ullage 300 is disposed between distendable membrane 302 and first and second spaced apart fluid reservoirs 304 and 306 each having separate fluid inlets and fluid outlets. With this construction the contents of the reservoirs can be delivered sequentially by first opening the outlet of reservoir 304 and then by opening the outlet of reservoir 306. Once again, the stored energy source, or elastomeric membrane 302 will act upon the conformable ullage which, in turn, will act upon the reservoirs to cause the fluid contained therein to be controllably expelled through the delivery port of the device. For example, as shown in FIG. 24, when the outlet of reservoir 304 is opened, ullage 300 will be urged downwardly against a yieldable pusher member 304a which defines the extent of reservoir 304, causing fluid to be expelled from the reservoir. Similarly, when the outlet of reservoir 306 is opened, ullage 300 will be urged downwardly against a deformable pusher member 306a which, along with the base define the extent of reservoir 306, causing the fluid contained within the reservoir to be controllably expelled (FIG. 25, the arrows "F" indicating outward fluid flow via flow control means).

Figure 26:
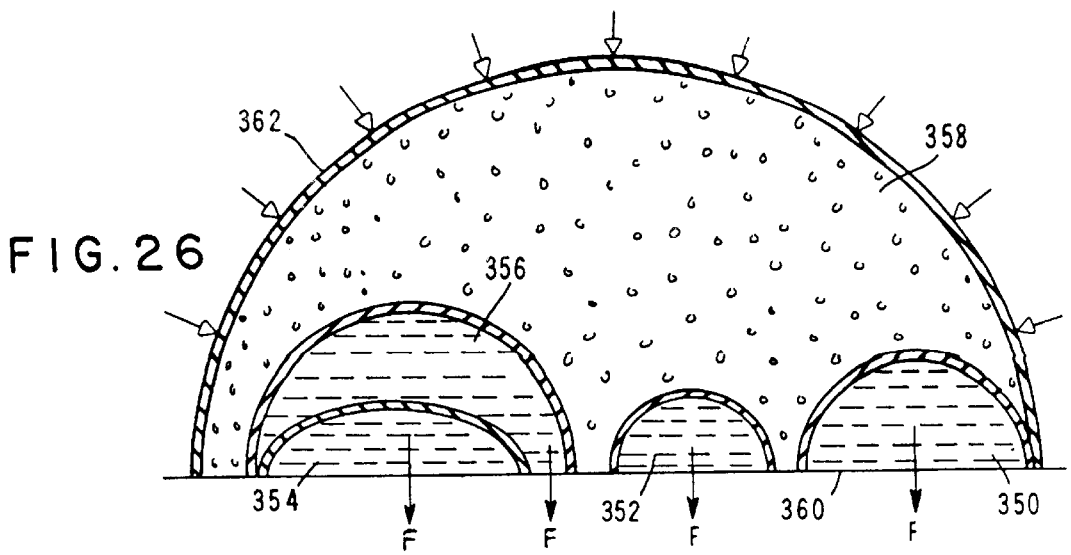
FIG. 26 is a generally diagrammatic view of still another form of conformable ullage construction of the invention showing four subreservoirs.

Further exemplifying the remarkable versatility of the conformable ullage construction of the present invention is the arrangement diagrammatically illustrated in FIG. 26, wherein four separate reservoirs 350, 352, 354, and 356 are acted upon by the conformable ullage 358 as it is urged toward base 360 by the stored energy means or distendable membrane 362. As indicated in FIG. 26, reservoirs 350, 352, and 354 are transversely spaced along the upper surface of the base of the device, while reservoir 356 is superimposed over reservoir 354. Each of these reservoirs is provided with a separate inlet so that different fluids can be introduced into each reservoir. In like manner, each reservoir is provided with its own outlet so that the fluids contained within the reservoir can be sequentially dispensed as the distendable membrane acts upon the conformable ullage 358 in the manner previously described.

It is to be understood that in the case of the constructions diagrammatically illustrated in FIGS. 22 through 26, the pressure exerted on the fluid reservoirs of the device can be varied depending upon the distendable membrane material properties, material thickness, footprints and the extension of the membrane. Altering the conformable ullage configuration along with the variations in the number and placement of fluid reservoirs which are to be acted upon by the ullage makes it possible to readily match a very large number of drug delivery protocols.

Figure 30A:
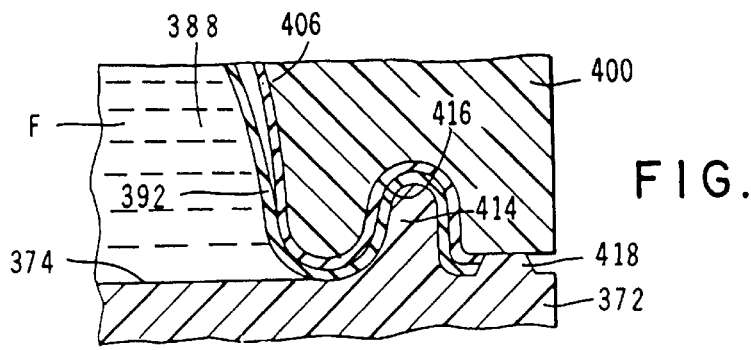
FIG. 30A is a greatly enlarged, cross-sectional view of the area indicated as 30A in FIG. 30.
Figure 30B:
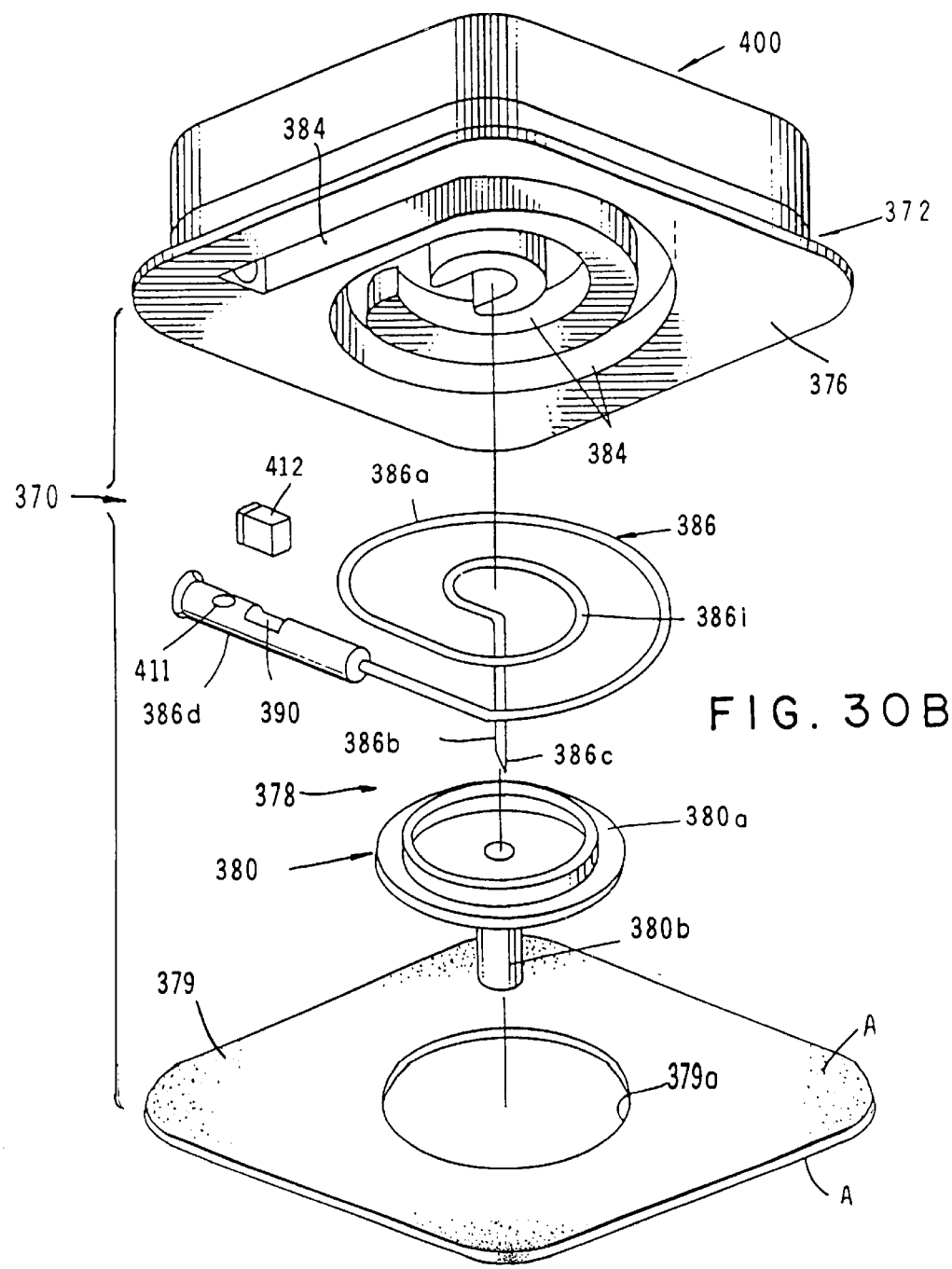
FIG. 30B is a generally perspective exploded view of the embodiment of the invention shown in FIGS. 27 through 30.
Figure 31:
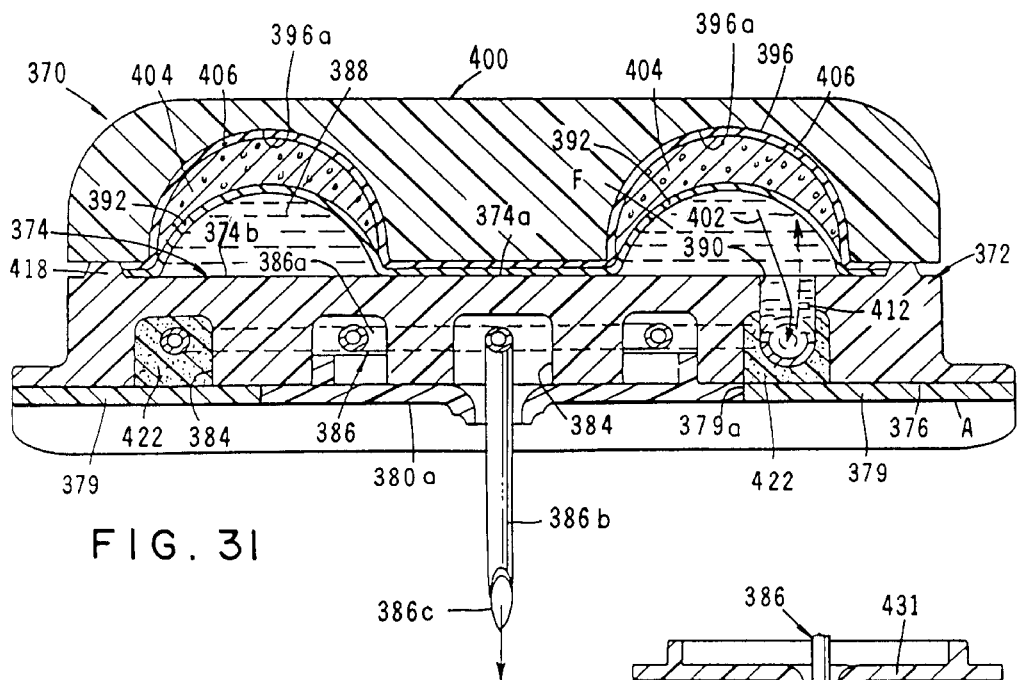
FIG. 31 is an enlarged, cross-sectional view taken along lines 31—31 of FIG. 27.

Referring to FIGS. 27 through 32, yet another form of the ultra low profile device of the invention is there shown and generally designated by the numeral 370. This latest embodiment of the invention is somewhat similar to the embodiment shown in FIGS. 7 through 17, but uniquely includes a generally toroidal-shaped, conformable ullage and reservoir (see FIG. 29). More particularly, the device here comprises a base 372, having an upper surface 374 including a central portion 374a and a peripheral portion 374b circumscribing central portion 374a. As best seen in FIG. 30B, base 372 is provided with a lower surface 376 to which a patient interconnection means or assembly 378 is connected. The patient interconnection means here comprises an apertured planar member 379 having an adhesive layer "A" on its upper and lower surfaces. As shown in FIG. 30 and 30B, a needle cap or sheath 380, which includes having a generally circular base 380a, is receivable within circular opening 379a of member 379. Depending from base 380a of the sheath is a tear-away needle cover 380b which can be separated from base 380a along a serration 380c (FIG. 30).

Formed within base 372 is a circuitous channel 384 (FIG. 30B) within which a novel spiral-like hollow cannula or capillary 386 is uniquely mounted in a manner presently to be described.

Figure 32:
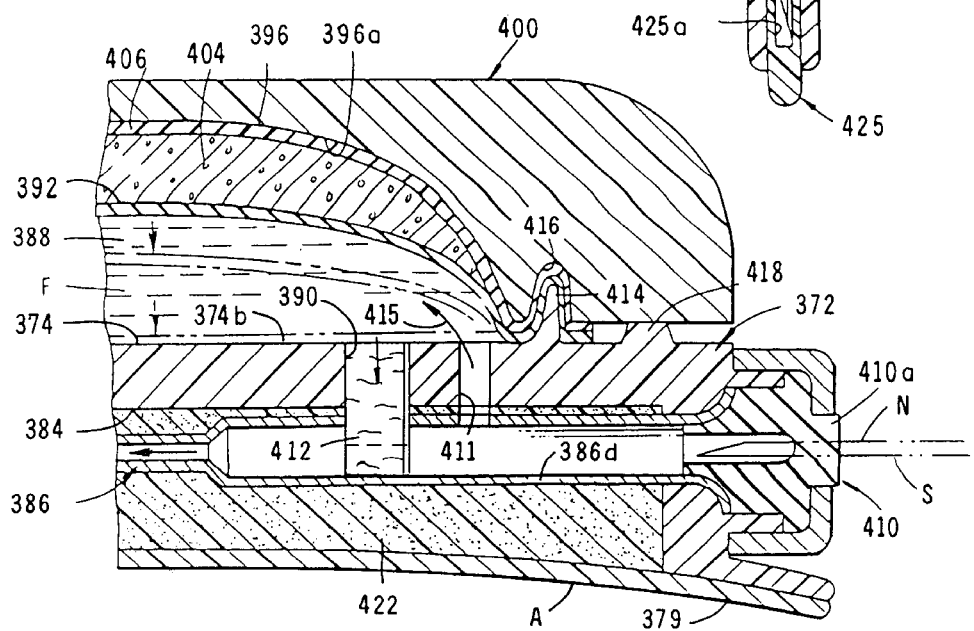
FIG. 32 is a greatly enlarged, cross-sectional view taken along lines 32—32 of FIG. 27.

As in the previously described embodiments, the barrier means or barrier membrane 392 cooperates with the upper surface 374 of base 372 to form a reservoir 388 having an inlet 411 and an outlet port 390 (FIG. 32) which are superimposed over channel 384 in the manner shown in FIGS. 30 and 30B. The barrier means is here provided in the form of at least one yieldable membrane 392 which is superimposed over base 372. A stored energy means is, in turn, superimposed over the fluid reservoir barrier membrane. The stored energy means is here provided in the form of at least one distendable elastomeric membrane 406. Membranes 392 and 406 are distendable as a result of pressure imparted on the membrane by fluids "F" introduced into reservoir 388 through port 411 (FIG. 32). As membrane 406 is distended, internal stresses will be established, which stresses tend to move the membrane toward a less distended configuration and in a direction toward base 372. As previously mentioned, a unique feature of this latest embodiment of the invention resides in the fact that the reservoir is generally toroidal in shape with the outer boundary thereof being defined by a toroidal-shaped chamber 396 formed in a cover member 400.

Provided within the toroidal-shaped chamber 396 is ullage defining means for engagement with barrier membrane 392 and distendable membrane 406, which cooperate to encapsulate the ullage defining means. The ullage defining means in the embodiment of the invention shown in FIGS. 28 through 32, uniquely comprises a conformable mass which substantially conforms to the shape of the distendable membrane as the membrane is distended. More particularly, as the distendable membrane returns toward its original, less distended configuration, the conformable ullage and the barrier membrane will conformably follow its movement toward engagement with the upper surface 374 of base 372 and fluid contained within the reservoir will flow uniformly outwardly of the device through port 390 in the direction of the arrow 402 of FIG. 31.

The stored energy means, while shown in the drawings as one distendable membrane 406, can comprise a laminate construction made up of a plurality of layers of elastomeric materials. The conformable ullage, which is identified in FIGS. 28 through 32 by the numeral 404, can be constructed from a number of materials such as various types of gels, foams, fluids and soft elastomers. Here the conformable ullage comprises a gel which is encapsulated between a barrier membrane 392 and distendable membrane 406 in the manner best seen in FIG. 29. Materials suitable for use in constructing the base, the cover and the distendable membrane are discussed in detail in U.S. Pat. No. 5,205,820.

Referring particularly to FIG. 29, in this latest form of the invention, the infusion means for infusing medicinal fluids from reservoir 388 into the patient comprises the previously identified circuitously shaped hollow cannula 386. Cannula 386 includes a body portion 386a which is mounted within circuitous channel 384 in a highly novel manner presently to be described. Cannula 386 also includes an outlet end 386b, here provided in the form of a needle-like segment, which extends generally perpendicularly downward from surface 376 of base 372 for subdermal infusion of medicinal fluids into the patient. For this purpose, segment 386b is provided with a sharp, pointed extremity 386c (see also FIG. 31). As previously discussed, protective sheath 380 surrounds and protects segment 386b of the cannula (FIG. 29).

Figure 27:
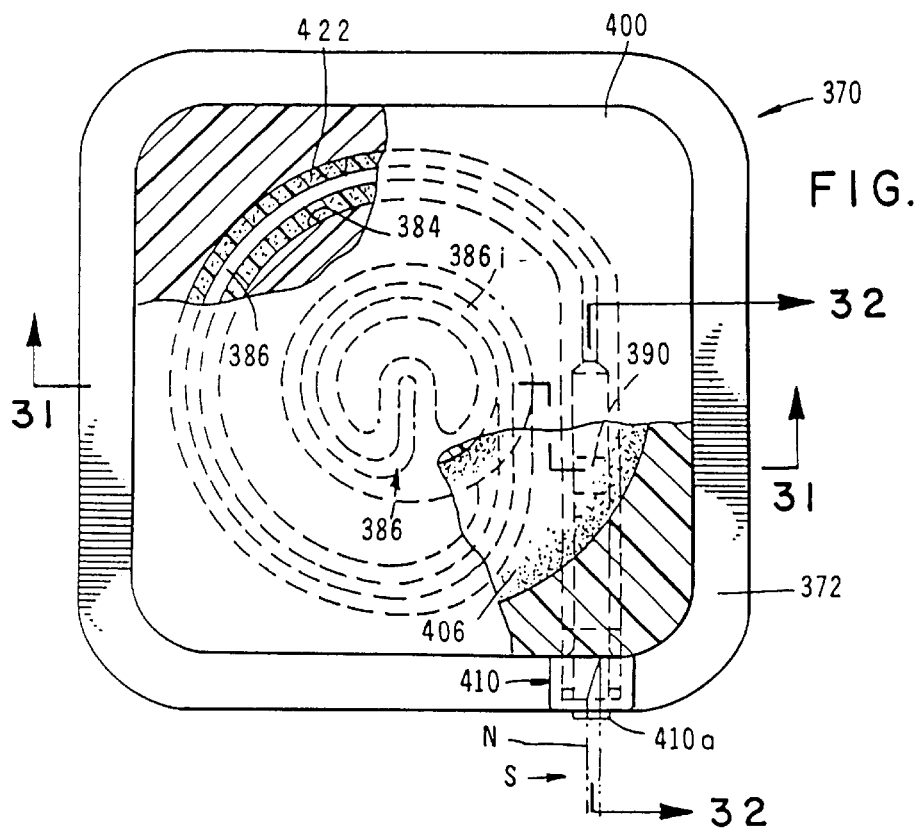
FIG. 27 is a top plan view of yet another embodiment of the invention partly broken away to show internal construction.
Figure 28:
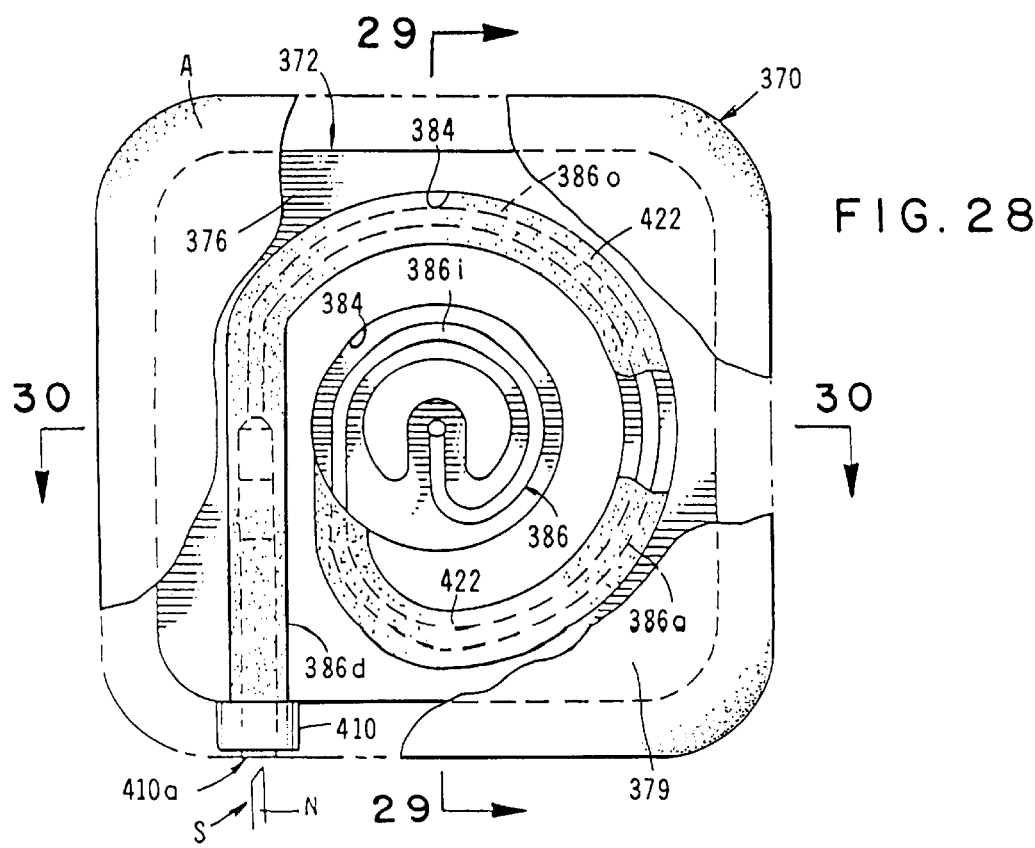
FIG. 28 is a bottom view of the apparatus shown in FIG. 27, again partly broken away to show internal construction.

Filling reservoir 388 is accomplished in the manner previously described by introducing fluid into the reservoir under pressure via a septum assembly 410 mounted in base 372 (FIGS. 27 and 32). Using a conventional syringe assembly "S", fluid can be introduced into the enlarged diameter portion 386d of cannula 386 via the septum assembly 410. During this filling step, barrier membrane 392 is yieldably distended outwardly against the conformable ullage 404 controllably moving it along with distendable member 406 toward cover 400. As the ullage assembly engages the upper wall of channel 396, it will uniquely conform to the channel surface as well as to the varying shape of barrier membrane 392. With this construction, when the fluid is dispensed from the device, the conformable ullage will permit the distendable membrane to provide a constant fluid expelling pressure on the fluid contained within the reservoir throughout the fluid delivery cycle, thereby avoiding undesirable delivery rate tail off at the end of the delivery period. This novel substantially linear performance permits the device to meet even the most stringent medicinal fluid delivery requirements.

As best seen in FIG. 32, during the fluid delivery step, fluid will flow from reservoir 388, through port 390, through a flow control means and then into the enlarged diameter portion 386d of cannula 386. The flow control means here comprises a flow control assembly 412 (FIG. 31) of a character similar to that shown in FIG. 4A and previously described herein in connection with the embodiment of FIGS. 1 through 4. After flowing through the flow control assembly, the fluid will flow outwardly of the device via the hollow cannula 386.

Barrier member 392, along with distendable membrane 406 are secured to base 372 in the manner best seen in FIG. 32. More particularly, the peripheral portion of base 372 is provided with an upstanding, generally circularly shaped tongue 414 which is received within a groove 416 provided in cover 400 as the cover assembly mateably engages base 372. Base 372 is also provided with an upstanding, circumferentially extending membrane cutting means or protuberance 418 (FIG. 30A). Protuberance 418 functions to cleanly cut both barrier membrane 392 and distendable membrane 406 upon the cover assembly being brought into pressural engagement with the base. As before, protuberance 418 also uniquely functions as a sonic energy director for the sonic weldment of base 372 and cover 400. With this construction, following cutting of the distendable membrane and the barrier membrane, the cover can be sonically welded to the base in the proximity of the upstanding tongue of the base and the mating groove in the cover by techniques well understood by those skilled in the art. After the sonic welding step, the cover, the distendable membrane, and the barrier membrane are all interconnected with the base in a manner to provide a tightly sealed enclosure.

Turning once again to FIGS. 28, 29, and 31, it can be seen that part of the body portion of the very small diameter spiral cannula 386 is uniquely supported within channel 384 of base 372 by a cannula encapsulation means shown here as a standard potting compound 422. Compound 422 rigidly supports the body portion of the cannula within channel 384 and dynamically supports the outer extremity 386o of the cannula body so that the spring-like inner portion 386i thereof (FIGS. 28 and 30) is free to move three dimensionally within channel 384. With this highly novel construction, when the device is connected to the patient with the needle portion 386b of the cannula penetrating the patient's body, as, for example, the patient's arm or leg, normal movement by the patient will permit the cannula to move within a potion of channel 384 while the base remains completely stationary. Without this important feature, normal movements by the patient causing flexing of the muscle and tissue would impart loosening forces to the device which, in time, could cause the adhesive pad "A" provided on the base of the device to separate from the patient's skin.

With the cannula enclosure subassembly 380 in position over cannula segment 386b, the reservoir of the device can be filled with the beneficial agent to be infused through use of a standard syringe assembly "S" having a needle "N" adapted to penetrate the septum 410a of the septum assembly (FIG. 32). Fluid flowing under pressure from the syringe will enter the enlarged diameter portion 386d of cannula 386 and flow in the direction of the arrow 415 in FIG. 32 inwardly of port 411 and toward the reservoir of the device. As the fluid under pressure flows into the reservoir, barrier membrane 392 will be distended outwardly against the conformable ullage 404 in a manner to cause distendable membrane 406 to move into engagement with the inner surface 396a of the toroidal-shaped channel formed in cover 400.

After the reservoir of the apparatus has been filled with the appropriate beneficial agent, the needle cap or covering 380b can be separated from the assemblage 380 by breaking it along the serration 380c (FIG. 29). This done, the device is interconnected with the patient by penetrating the patient's skin with the point 386c of the infusion cannula 386. As the patient's skin and tissue is penetrated by the infusion needle, the adhesive pad "A" provided on the lower surface of member 379 will cause the base of the device to adhere to the patient's skin. In some instances, it is desirable to provide a protective peel layer over the adhesive pad until the time the device is to be used. In such instances, the protective layer is peeled from the lower surface of member 379 immediately prior to use of the device.

As previously mentioned, the highly novel manner in which the very small diameter cannula 386 is mounted within channel 384 formed in base 372 permits the central portion 386i of the infusion cannula to move three dimensionally relative to the base within the limits of channel 384. This important feature permits the base of the device to remain stationary even though movement of the patient's extremities, which cause flexing of the muscles, skin, and tissue, tend to impart forces on the needle portion of the cannula which, but for its ability to free float within channel 384, would cause loosening of the adhesive pad.

With the device securely interconnected with the patient, and with sheath 380b removed from base 380, distendable membrane 406 will tend to return to its less distended configuration. As the distendable membrane moves toward base 372, the conformable ullage 404 will closely conform to the outer surface of the barrier membrane thereby assuring a complete and substantially linear flow of fluid from the reservoir 388, through the cannula 386, and into the patient.

Figure 30C:
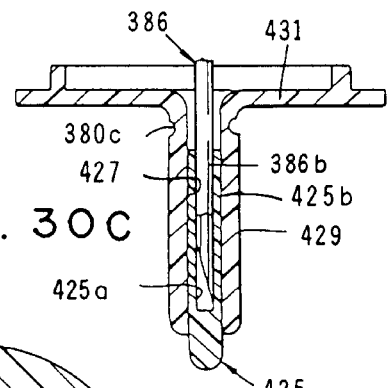
FIG. 30 is a cross-sectional view taken along lines 30—30 of FIG. 28.

Referring to FIG. 30c, an alternate form of needle cover is there illustrated. This form of the needle cover is similar to that just described save for the fact that a protective sheath assembly further includes a closure means or cap 425 having an inner bore 425a within which cannula portion 386b is sealably received. The outer surface 425b of cap 425 is telescopically received within a central bore 427 provided in the downwardly protruding stem-like extremity 429 of the sheath assembly in the manner shown in FIG. 30C. It is to be noted that the sheath assembly of this form of the invention also includes a portion 431 which is receivable within aperture 379a provided in base portion 379. With this construction, cap 425 prevents fluid flow from the hollow cannula until sheath 429 is broken away along serration 300c and cap 425 is removed from extremity 386b of the infusion cannula.

Figure 33:
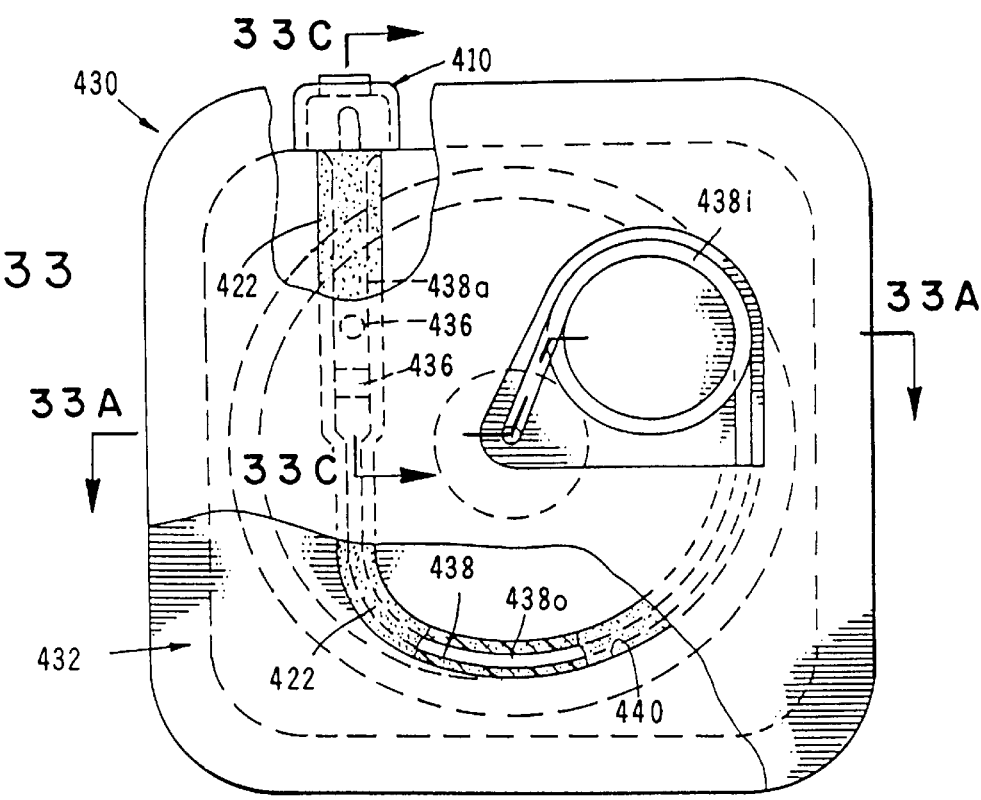
FIG. 33 is a top plan view of another form of the invention partly broken away to show internal construction.
Figure 33A:
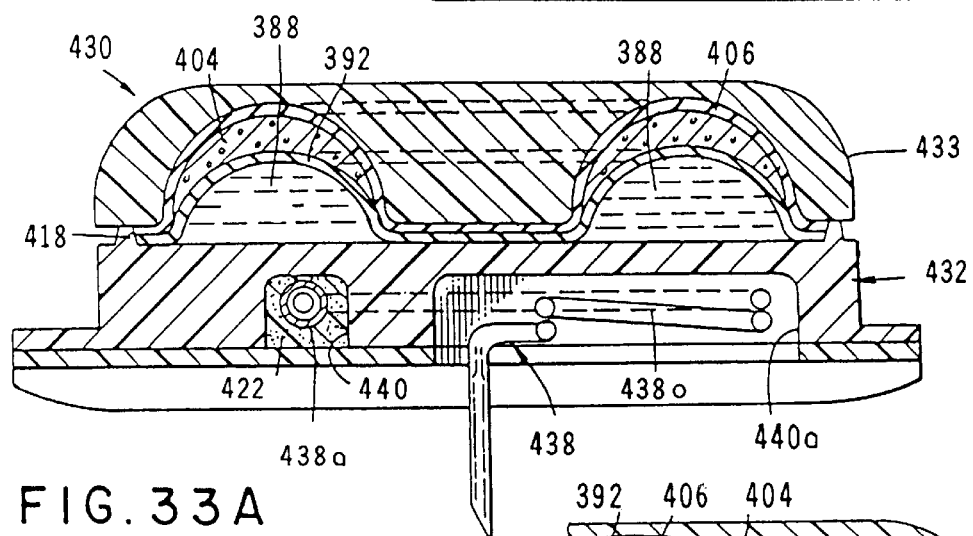
FIG. 33A is a cross-sectional view taken along lines 33A—33A of FIG. 33.
Figure 33C:
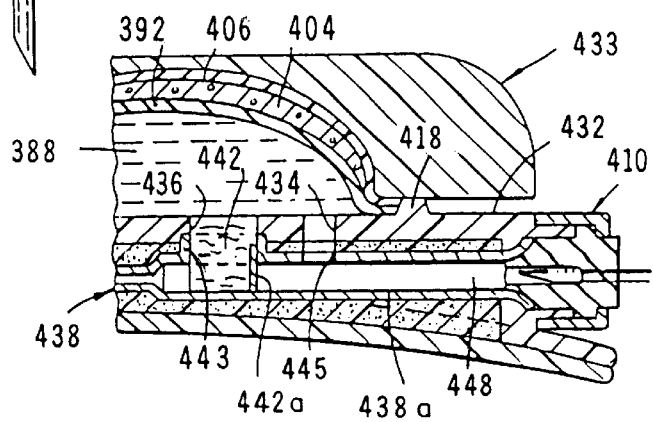
FIG. 33C is a cross-sectional view taken along lines 33C—33C of FIG. 33.

Turning to FIGS. 33, 33A, and 33C, still a further form of the ultra low profile device of the invention is there illustrated and generally designated by the numeral 430. This embodiment of the invention is similar in many respects to that shown in FIGS. 27 through 32 and, therefore, like numbers are used in these figures to identify like components. This apparatus is unique in that the microbore tubing used to form the body portion of the hollow cannula functions not only as a fluid delivery means, but also as a flow rate control means for controlling the rate of fluid flow from the device. Additionally, the inner body portion of the cannula is coiled in a unique manner to enhance the ability of the cannula body to move relative to the base of the device.

The apparatus of this latest form of the invention includes a base 432 which cooperates with a barrier membrane 392, a conformable ullage 404, a distendable membrane 406 and a cover 433 to form a generally toroidal-shaped reservoir 388, having an inlet 434 and an outlet 436 both of which communicate with a delivery cannula 438. As before, a portion of cannula 438 is receivable within a circuitous channel 440 formed in base 432. Cannula 438 has an outer segment 438o, an inner coiled portion 438i, and an enlarged diameter end portion 438a. Filter means, here provided as a porous filter 442 with fluid impermeable layment 442a (FIG. 33C), is disposed between the outlet of reservoir 388 and an inlet 443 formed in enlarged diameter portion 438a of cannula 438. Also formed in the enlarged diameter portion 438a of the cannula is an outlet port 445 which communicates with inlet 434 of reservoir 388. Fluid impermeable layer 442a serves to interrupt the flow and direct it to inlet 445. Outlet port 445 also communicates with a fluid passageway 448 formed in enlarged diameter portion 438a, which passageway is sealed at its outboard end by a septum assembly 410 of the character previously described. Fluid introduced into the device via septum assembly 410 will flow through passageway 448 and then into reservoir 388 via inlet 434. As the fluid enters the reservoir, it will distend the distendable membrane and moves the conformable ullage in the manner previously discussed.

Figure 33B:
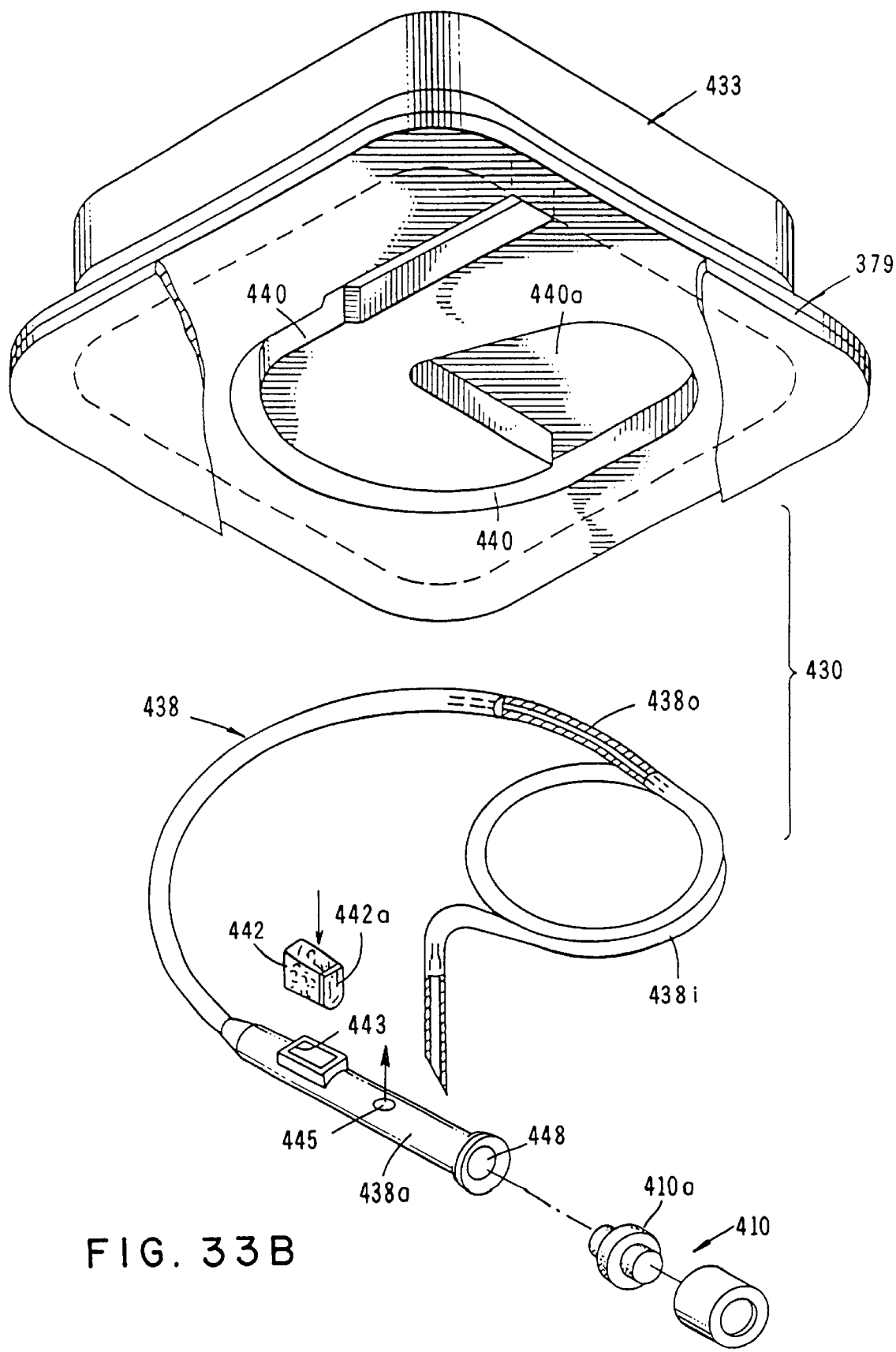
FIG. 33B is a generally perspective, exploded view of the apparatus shown in FIG. 33.

Turning particularly to FIGS. 33A and 33B, it is to be noted that the outer portion 438o of the cannula is secured in place within channel 440 by a suitable encapsulation means, such as the previously described potting compound 422. With this construction, the coiled inner portion 438i of the cannula is free to move within the portion of channel 440 designated as 440a in FIG. 33A. With this unique arrangement, normal movement by the patient will permit the cannula to move three dimensionally within channel 440a while the base remains completely stationary. Without this important feature, each movement by the patient that causes flexing of the skin, muscles and tissue could impart undesirable loosening forces to the adhesive pad which, in turn, could cause the base of the device to become separated from the patient.

Once the device has been removably interconnected with the patient, infusion of the beneficial agent contained within reservoir 388 via cannula 438 is accomplished in the manner previously described. However, in this latest embodiment of the invention, the rate of fluid flow from the device is closely controlled by controlling the size of the microbore portion 438o of the cannula which communicates with passageway 448. The diameter of the bore of the microbore tubing used to construct cannula portion 438o can range from between about 0.0002 and about 0.005 inches so that the beneficial agent can be controllably disposed over relatively long periods of time up to 24 hours or longer.

Referring to FIGS. 34 through 37A, still another form of the ultra low profile device of the invention is there shown and generally designated by the numeral 460. As best seen by referring to FIGS. 34 and 34A, this latest embodiment of the invention is similar in some respects to that shown in FIGS. 27 through 32. Accordingly, like numbers are used to describe like components. This embodiment of the invention is unique in that it includes dual reservoirs which communicate with a novel, serpentine-shaped hollow cannula (FIG. 37A), the character of which will presently be described.

As best seen in FIGS. 36 and 36a, the apparatus here comprises a base 462 having an upper surface 464, including a central portion 464a and a peripheral portion 464b circumscribing central portion 464a. Base 462 is also provided with a lower surface 466. Formed within base 462 is a circuitous channel 470 (FIG. 34A), which receives a portion of the infusion means, or serpentine-shaped hollow cannula 472, of the invention.

The apparatus shown in FIGS. 34 through 37A also includes stored energy means for forming, in conjunction with the base 462, a pair of reservoirs 474 and 476 having outlets 478 and 480 respectively. As best seen in FIG. 34A, outlet 478 is in communication with a first inlet port 482 provided in cannula 472, while outlet 480 is in communication with a second inlet port 484 provided in cannula 472 (FIGS. 34A and 37A). Filling of outer reservoir 474 is accomplished via a first septum assembly 486 which fills through a reservoir inlet 474a and a filter F-1, while filling of central reservoir 476 is accomplished via a second septum assembly 488 which fills through a reservoir inlet 476a and a filter F-2 (FIG. 34A) Filters F-1 and F-2 comprise a part of the filler means of the invention. Both septum assemblies include a pierceable septum 486a and are used in the same manner as previously described.

As before, the stored energy means is provided in the form of at least one distendable membrane 496 which is superimposed over base 462. An ullage defining means is disposed within each reservoir for engagement with membrane 496 which, after being distended, will tend to return to its less distended configuration. Once again, the ullage defining means of this latest embodiment of the invention comprises a conformable ullage of the general character previously described which uniquely conforms to the shape of the distendable membrane as the membrane tends to return to its less distended configuration. The first conformable ullage, which is disposed within outer reservoir 474, is identified in FIGS. 36 and 36A by the numeral 492. The second conformable ullage, which is disposed within central reservoir 476, is designated by the numeral 494. Ullages 492 and 494 each comprise a deformable mass constructed from materials such as gels, foams, fluids and soft elastomers. Where, as is here the case, the conformable ullage comprises a gel, an encapsulation barrier membrane 490 is used to encapsulate the ullage medium and separate it from the fluid reservoir. Once again, the conformable ullage is located between the barrier membrane and cover 500. More particularly, ullage 492 is located between membrane 490 and an oval shaped channel 502 formed in cover 500, while ullage 494 is located between membrane 490 and a generally domed-shaped cavity 504 formed in cover 500 (FIG. 36B).

Turning particularly to FIG. 37A the serpentine-shaped cannula 472 of the device includes a body portion 472a constructed from a length of microbore tubing, an enlarged diameter portion 472b and a needle-like outboard extremity 472c. Receivable within inlets 482 and 484 formed in portion 472b are filter means for filtering fluids flowing from the dual reservoirs. These filter means are here provided as porous filter members 507 and 509 which can be constructed from various materials such as polysulfone.

As indicated in FIG. 37, the peripheral portion of the cover 500 is provided with a capture groove 510 and an adjacent tongue 512. Similarly, base 462 is provided with tongue 514 which mates with groove 510 as the cover moves into engagement with base 462. Base 462 is further provided with an upstanding membrane cutting means, or protuberance 516 which functions to cleanly cut the stored energy means and the barrier membrane 490 upon cover 500 being brought into pressural engagement with base 462. With this construction, following cutting of the membrane the cover can be sonically welded to the base in the manner previously described.

When the cover and base are sealably joined together extremity 472c of the infusion cannula extends from the assemblage in the manner shown in FIG. 36B and is covered by a protective cover means or cap assembly 520. Cap assembly 520 comprises an elongated needle cover 520a having a central bore which closely receives portion 472c of cannula 472 in the manner shown in FIG. 36B. Cap 520a has an outside diameter closely corresponding to the inside diameter of a sheath 522 which is joined with a base extension 462e by means of a serrated portion 462f which enables sheath portion 522 to be broken away from the base assembly, and along with cap 520a slidably removed from portion 472c of the cannula.

In using the apparatus of this latest form of the invention, reservoir 474 can be filled via septum assembly 486 using a conventional fluid containing syringe assembly having a needle "N" adapted to penetrate septum 486a of septum assembly 486. Similarly, central reservoir 476 can be filled via septum assembly 488 using a second syringe assembly containing a second fluid which is the same or different from the first fluid used to fill chamber 474. With the chambers thus filled, the protective covering means which covers 472c of the cannula can be broken away and removed and the needle end portion 472c of the device inserted into the vein of the patient. As before, the base of the device is provided with a suitable adhesive to enable the device to be removably affixed to the patient's body such as to the arm or leg of the patient. Further, the device includes a butterfly assemblage 523 which is integrally formed with base 462. Assemblage 523 provides appropriate surface area for tape used to secure the infusion cannula in place.

Once the device is interconnected with the patient, it will be appreciated that the fluids contained within first chamber 474 and central chamber 476 will be urged to flow through the cannula as the stored energy means, or distendable membrane 496 tends to return to its less distended configuration. As before, the conformable ullages contained within the reservoirs will closely conform to the changing shape of the stored energy means as the stored energy means moves toward surface 464a and 464b of base 462. However, because the fluid outlet 478 of the outer chamber of the device communicates with the enlarged diameter portion of the cannula at a location further removed from extremity 472a, fluid flowing from the outer reservoir will flow toward the patient at a slower rate than will fluid flowing from the central reservoir via outlet 480. Since the fluid flowing through outlet 480 has a shorter distance to travel through the cannula than the fluid flowing from the outer chamber, the rate of flow of this fluid will be greater than the rate of flow of the first fluid contained within the outer chamber. The microbore tubing portion of the cannula assembly 472 thusly functions both as a fluid conduit and as a rate control means for variably controlling the rate of fluid flowing from the outer and central reservoirs of the device.

Referring to FIGS. 38 through 42B, yet another form of the ultra low profile device of the invention is there shown and generally designated by the numeral 525. This latest embodiment of the invention is quite similar to the embodiment shown in FIGS. 28 through 32 in that it also includes a generally toroidal-shaped, conformable ullage and reservoir (see FIG. 38). Because of the similarity of this latest form of the invention to that shown in FIGS. 28 through 32, like numerals will be used to identify like components.

Figure 38:
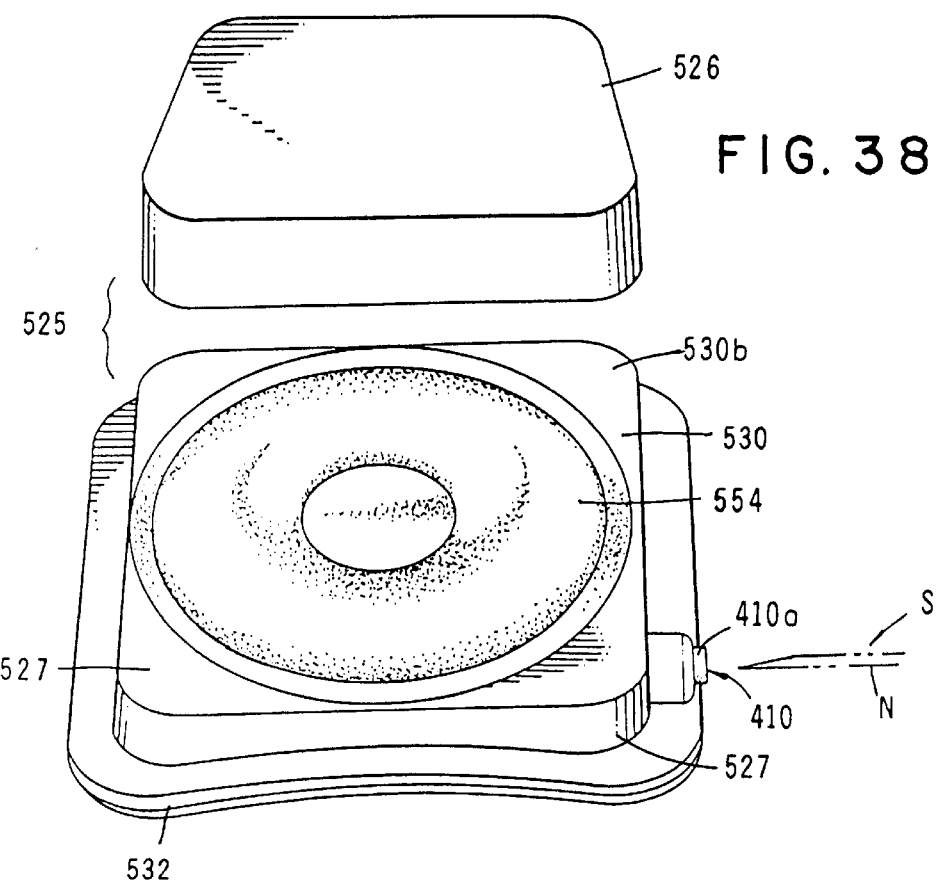
FIG. 38 is a generally perspective view of yet another form of low profile fluid delivery apparatus of the present invention.
Figure 39:
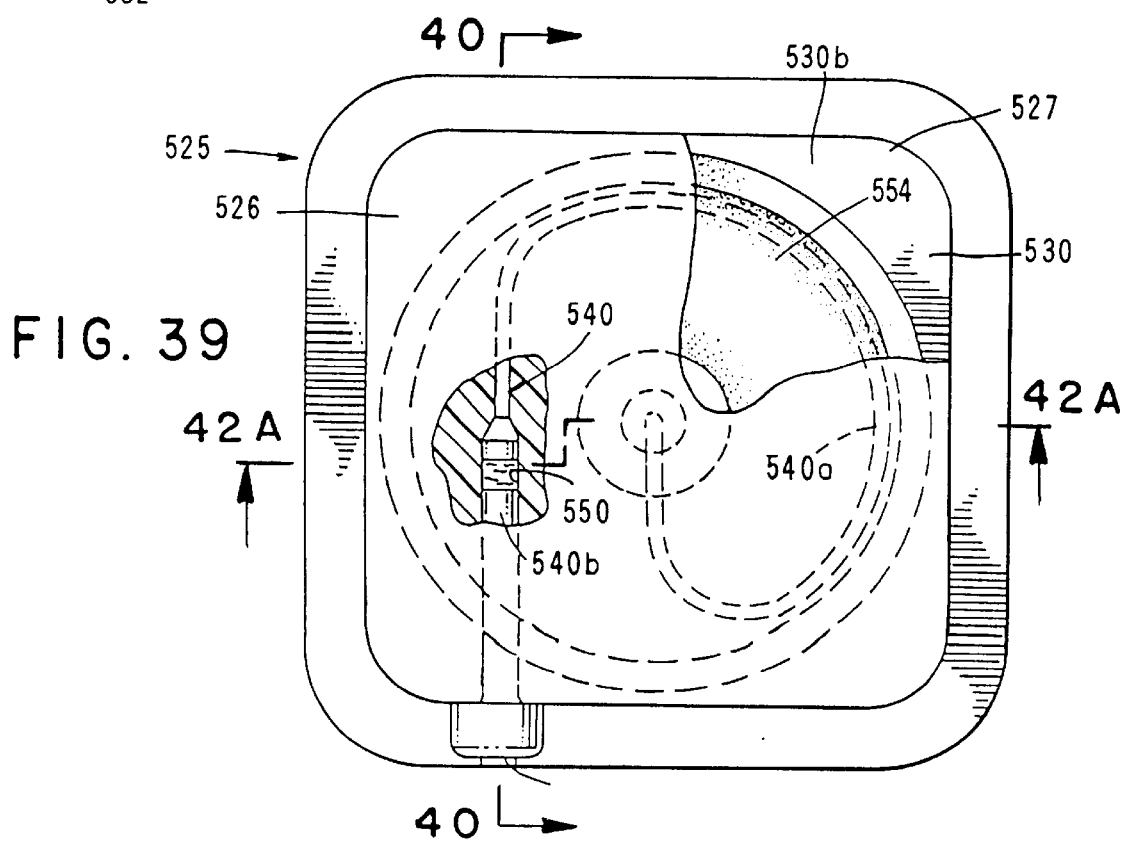
FIG. 39 is a top view of the embodiment shown in FIG. 38, partly broken away to show internal construction.

As best seen in FIGS. 38, 39, and 40, the device here comprises a base 527, having an upper surface 530 including a central portion 530a and a peripheral portion 530b circumscribing central portion 530a. As before, base 527 is provided with a lower surface to which a patient interconnection means or member 532 is connected. Member 532 functions to releasably interconnect the device to the patient by means of an adhesive layer "A". Also connected to base 527 is a protective cover means including a needle cap or sheath subassembly 534 of a construction similar to that shown in FIG. 30C. Subassembly 534 includes a protective sheath 536 within which a closure means or cap 538 is telescopically received. Cap 538 has an inner bore within which penetrable cannula portion 540c is sealably received. The upper portion of sheath 536 is provided with a serration 537 so that the sheath, along with cap 538, can be separated from the cannula at time of use.

Figure 42:
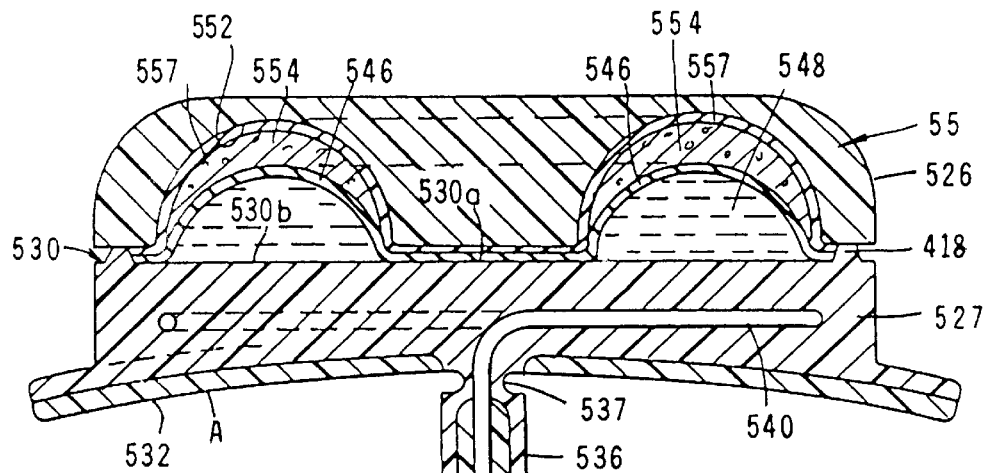
FIG. 42 is an enlarged, cross-sectional view taken along lines 42—42 of FIG. 41.
Figure 42B:
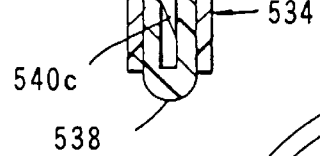
FIG. 42B is an enlarged, generally perspective view of the hollow cannula subassembly of this latest form of the invention.
Figure 42A:
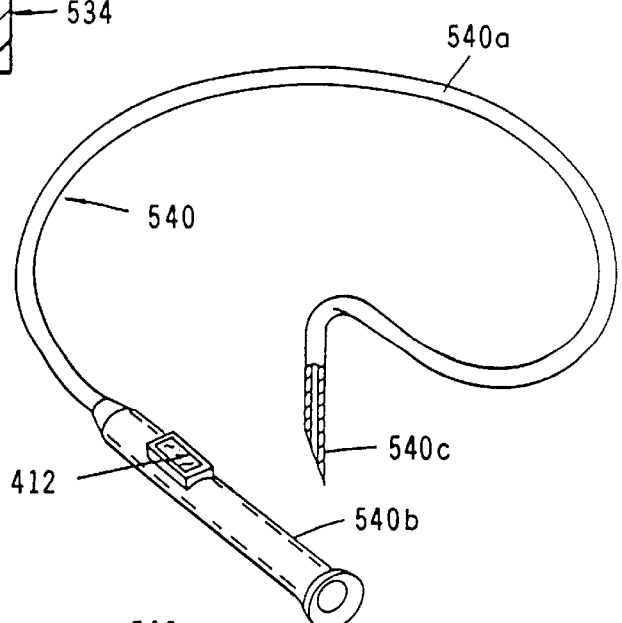
FIG. 42A is a cross-sectional view similar to FIG. 42, but showing the stored energy means having moved into a less distended configuration.

Unlike the apparatus shown in FIGS. 28 through 32, the hollow cannula or capillary 540 of this embodiment of the invention is insert molded within base 527 in the manner shown in FIG. 40. However, as in the previously described embodiments, barrier membrane 546 cooperates with the upper surface of base 527 to form a reservoir 548 having an inlet/outlet port 550 (FIG. 40) which is superimposed over enlarged diameter portion 540b of cannula 540 in the manner shown in FIG. 40. The barrier membrane 546, functions in the same manner to accomplish the same result as previously described herein. As previously mentioned, the reservoir is generally toroidal in shape with the outer boundary thereof being defined by a toroidal-shaped channel 552 formed in a cover member 525 (FIG. 42A).

Provided within the toroidal-shaped reservoir is ullage defining means for engagement with membrane 546 as the membrane moves into its distended configuration. The ullage defining means in the present embodiment, shown here as 554, also operates in the same manner to accomplish the same result as previously described.

In this latest form of the invention, the infusion means for infusing medicinal fluids from reservoir 548 into the patient comprises the previously identified circuitously shaped hollow cannula 540. Cannula 540 includes a body portion 540a which is molded in base 527 in a manner well known by those skilled in the art. Cannula 540 also includes an outlet end, here provided in the form of the needle-like segment 540c, which extends generally perpendicularly downward from base 527 for subdermal infusion of medicinal fluids into the patient. As before, a protective sheath assembly 534 surrounds and protects segment 540c of the cannula (FIG. 40).

Filling reservoir 548 is accomplished in the manner previously described by introducing fluid into the reservoir under pressure via a septum assembly 410 mounted in base 527 (FIGS. 40 and 40a). Using a conventional syringe assembly "S", fluid can be introduced into the enlarged diameter portion 540b of cannula 540 via the septum assembly 410. During this filling step, barrier membrane 546 is distended outwardly against the conformable ullage 554 controllably moving it, along with a distendable membrane 557, toward cover 525. As the ullage assembly engages the upper wall of channel 552, it will uniquely conform to the channel surface as well as the varying shape of distendable membrane 557. With this construction, when the fluid is dispensed from the device, the conformable ullage will permit the distendable membrane to provide a constant fluid expelling pressure on the fluid contained within the reservoir throughout the fluid delivery cycle, thereby avoiding undesirable delivery rate tail off at the end of the delivery period.

As best seen in FIG. 40, during the fluid delivery step, fluid will flow from reservoir 548, through port 550 through a flow control means shown here as flow control assembly 412 then into the enlarged diameter portion 540b of cannula 540. Flow control assembly 412 is identical to that shown in FIG. 30B and functions as described herein.

Distendable member 557, along with barrier membrane 546, is secured to base 527 in the manner previously described as is cover member 525. As before, protuberance 418 also uniquely functions as a sonic energy director for the sonic weldment of base 527 and cover 525.

The device of this latest form of the invention is used in a manner similar to the apparatus shown in FIGS. 27 through 32 and, therefore, the details of operation of the device will not here be discussed.

Referring to FIGS. 43 through 48A, another form of the ultra low profile device of the invention is there shown and generally designated by the numeral 560. As best seen by referring to FIGS. 43, 44 and 45, this embodiment of the invention is similar in some respects to that shown in FIGS. 34 through 37A save that the reservoir configuration is different as is the filling means.

Figure 43:
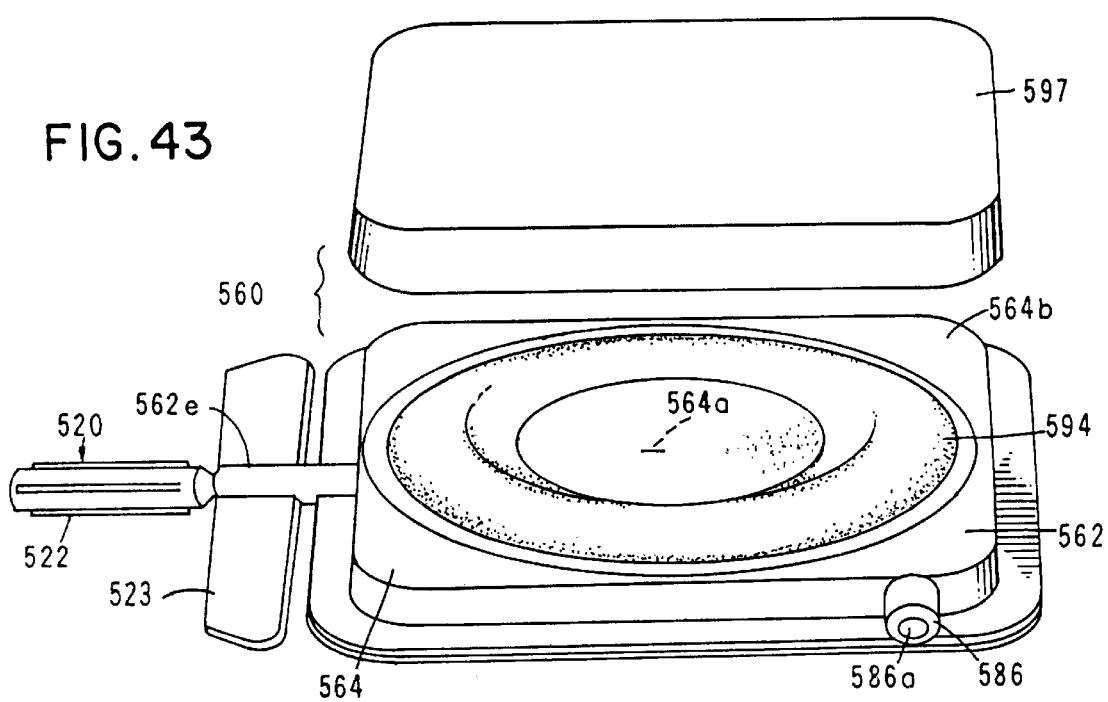
FIG. 43 is a generally perspective, exploded view of yet another embodiment of the fluid delivery apparatus of the invention.
Figure 45:
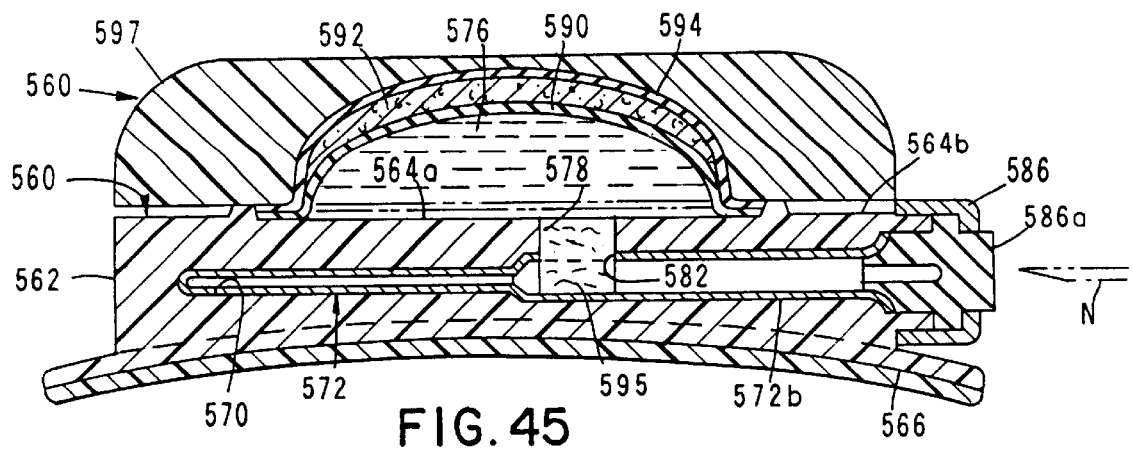
FIG. 45 is an enlarged cross-sectional view taken along lines 45—45 of FIG. 44.
Figure 47:
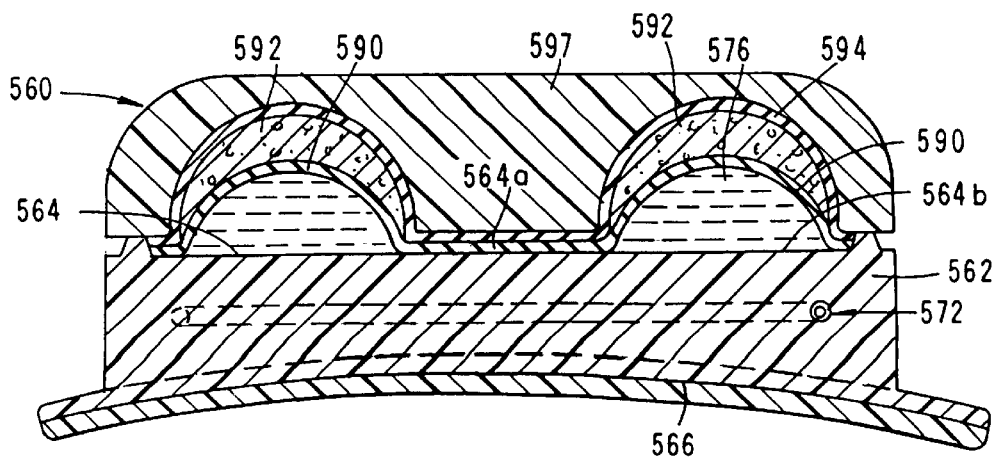
FIG. 47 is an enlarged cross-sectional view taken along lines 47—47 of FIG. 46.

As best seen in FIGS. 43 and 45, the apparatus here comprises a base 562 having an upper surface 564, including a central portion 564a and a peripheral portion 564b circumscribing central portion 564a. Base 562 is also provided with a lower surface 566. Formed within base 562 is a circuitous channel 570 (FIG. 44), which receives a portion of the infusion means, or serpentine-shaped hollow cannula 572, of the invention.

As before, this latest form of the invention includes a stored energy means for forming, in conjunction with the base 562, a generally toroidal shaped reservoir 576 having an outlet 578. As best seen in FIG. 45, outlet 578 is in communication with an inlet port 582 provided in cannula 572. Filling of reservoir 576 is accomplished in the manner previously described via a septum assembly 586, which includes a pierceable septum 586a that is pierceable by a syringe needle "N" (FIG. 45).

As before, the stored energy means comprises at least one distendable membrane 594 which is superimposed over base 562. An ullage defining means is disposed within reservoir 576 for engagement with membrane 594 which, after being distended, will tend to return to its less distended configuration. Once again, the ullage defining means of this latest embodiment of the invention comprises a conformable ullage 592 of the general character previously described which uniquely conforms to the shape of the distendable membrane as the membrane tends to return to its less distended configuration. Ullage 592 is of the general character previously described and includes an encapsulation barrier membrane 590 which functions to encapsulate the ullage medium.

Figure 44:
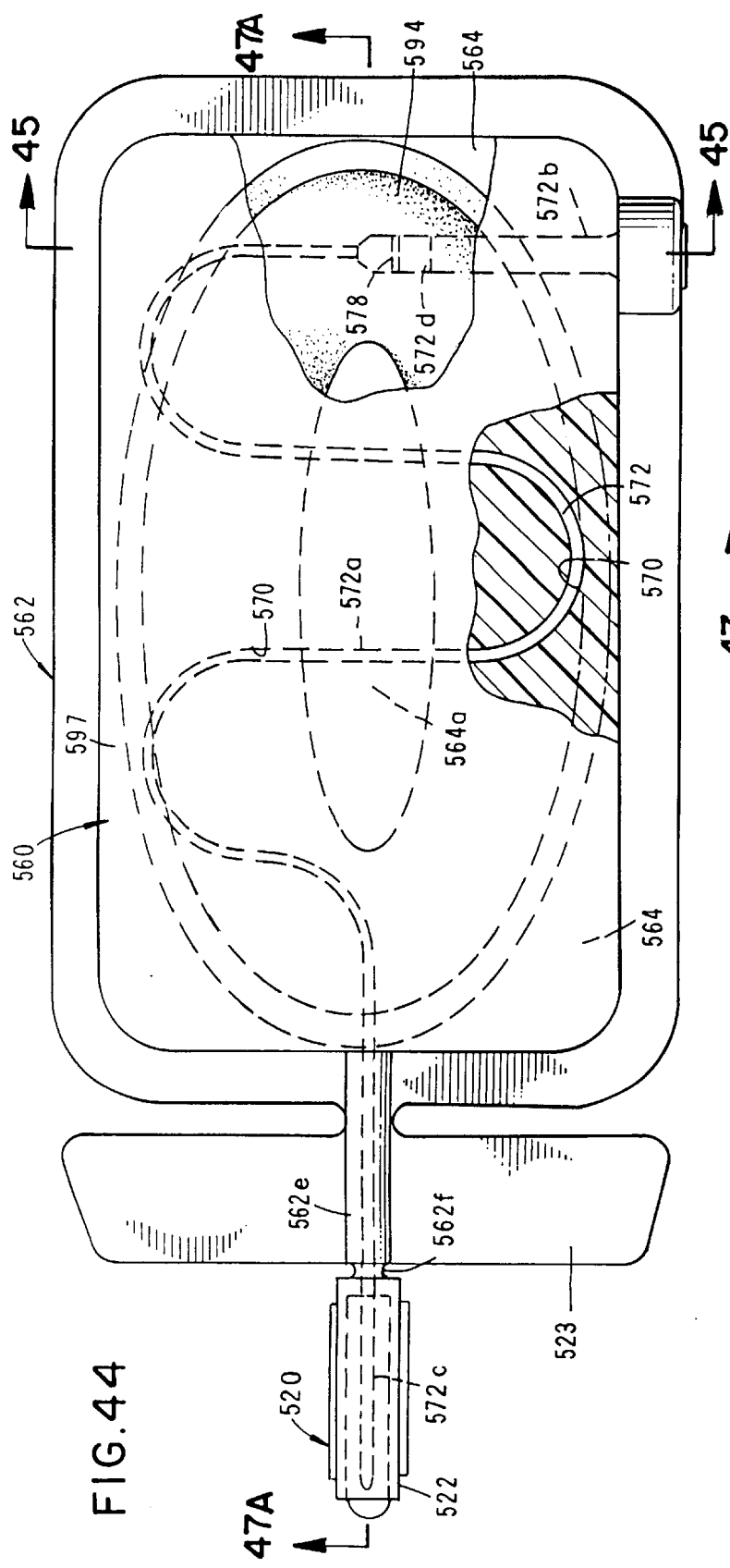
FIG. 44 is an enlarged top plan view of the embodiment shown in FIG. 43 partially broken away to show internal construction.

Turning particularly to FIGS. 44 and 47C the serpentine-shaped cannula 572 of the device includes a body portion 572a constructed from a length of microbore tubing, an enlarged diameter portion 572b and a needle-like outboard extremity 572c. Receivable within an inlet 572d formed in portion 572b is filter means for filtering fluids flowing from reservoir 576. This filter means is here provided as a porous filter member 595 which can be constructed from various materials such as polysulfone.

A cover 597 is receivable over base 562 and includes a capture groove 600 and an adjacent tongue 602 (FIG. 47B). Similarly, base 562 is provided with tongue 604 which mates with groove 600 as the cover moves into engagement with base 562. As before, base 562 is also provided with an upstanding membrane cutting means, or protuberance 606 which functions to cleanly cut the stored energy means and the barrier membrane upon the cover being brought into pressural engagement with base. With this construction, following cutting of the membrane, the cover can be sonically welded to the base in the manner previously described.

Figure 46:
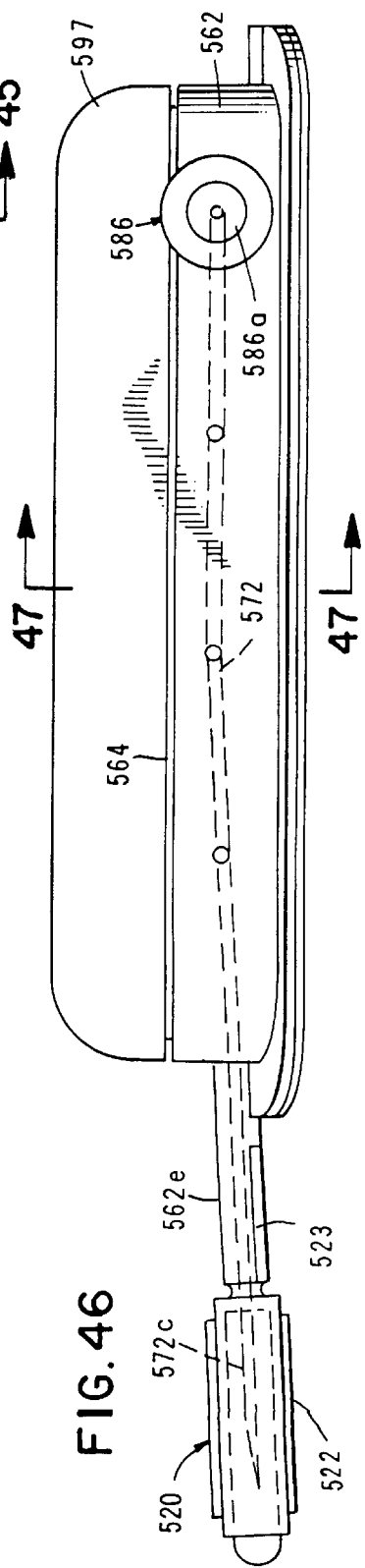
FIG. 46 is a front view of the apparatus shown in FIG. 44.

When the cover and base are sealably joined together extremity 572c of the infusion cannula extends from the assemblage in the manner shown in FIGS. 44 and 46 and is covered by a protective cover means or cap assembly 520 of the character previously described herein. As before, cap assembly 520 includes a sheath 522 which is joined with a base extension 562e by means of a serrated portion 562f which enables sheath portion 522 to be broken away from the base assembly, and along with the closure cap, slidably removed from portion 572c of the cannula.

In using the apparatus of this latest form of the invention, reservoir 576 can be filled via septum assembly 586 using a conventional fluid containing syringe assembly having a needle "N" adapted to penetrate septum 586a of septum assembly 586. With the reservoir thus filled, the protective covering means which covers the end of the cannula can be broken away and removed and the needle end portion 572c of the device inserted into the vein of the patient. As before, the base of the device is provided with a suitable adhesive to enable the device to be removably affixed to the patient's body such as to the arm or leg of the patient. Further, the device includes a butterfly assemblage 523 which is integrally formed with base 562 and provides an appropriate surface area for tape used to secure the infusion cannula in place.

Once the device is interconnected with the patient, it will be appreciated that the fluids contained within reservoir 576 will be urged to flow through the cannula as the stored energy means, or distendable membrane 594 tends to return to its less distended configuration. As before, the conformable ullages contained within the reservoirs will closely conform to the changing shape of the stored energy means as the stored energy means moves toward the upper surface of the base. During the infusion step, the microbore tubing portion of the cannula assembly functions both as a fluid conduit and as a rate control means for variably controlling the rate of fluid flowing from the reservoir of the device.

Referring to FIGS. 48 through 52, various forms of hollow cannula constructions usable with ultra low profile devices of the general nature described in the preceding paragraphs are there shown. Turning first to the hollow cannula construction shown in FIGS. 48 and 48A, it is to be observed that this cannula construction is similar in many respects to that shown in FIG. 47C. However, in this construction, the enlarged diameter portion 615b of the hollow cannula 615 is provided with a fluid outlet port 617 which is adapted to communicate with a reservoir inlet of a reservoir defined by an elastomeric membrane superimposed over a base having an upper surface. More particularly, in the construction of the embodiment of the invention shown in FIGS. 44 through 47C, the reservoir of the device is filled by fluids flowing outwardly of the enlarged diameter portion 572b via outlet 572d and flow control member 595. In the cannula construction shown in FIG. 48, fluid flows directly to the reservoir through outlet 617 and flow of the fluid is not impeded by the flow control device 595.

As was the case in the earlier described hollow cannula construction, the hollow cannula shown in FIGS. 48 and 48A comprises a needle-like outboard extremity 615c and a central portion 615a. At least a portion of the central section 615a of the cannula 615 is formed from a length of microbore tubing 619 having a very small diameter microbore fluid flow path 621. By adjusting the size of the microbore fluid passageway 621, it is apparent that the rate of fluid flow through the cannula can be closely controlled.

As was the case with the earlier constructions, enlarged diameter portion 615b of the hollow cannula includes a swagged end portion 623 which receives the pierceable septum 586*a* in the manner shown in FIG. 48A.

With the cannula construction shown in FIGS. 48 and 48A, filling of the reservoir can be accomplished very quickly through the use of a conventional syringe having a needle adapted to pierce septum 586*a* so that fluid can flow into enlarged diameter portion 615*b*. The fluid flowing into the enlarged diameter portion can then freely flow into the reservoir via outlet 617 without impedance from the small diameter tubing which makes up the body of the hollow cannula and without impedance from the flow control device or filter media 595 with fluid impermeable layer 595*a*. Fluid is expelled from the reservoir by the stored energy means in the same manner as previously described herein. During the infusion process, the fluid flows from the fluid reservoir as a result of the urging of the stored energy means, through filter media 595, and into the body portion 615*a* of the cannula. By regulating the diameter of the microbore 621, the amount of fluid flowing from the device as a function of time can be closely regulated.

Turning next to FIGS. 49 through 50A, an alternate form of hollow cannula construction is there illustrated. This type of cannula construction is similar in many respects to that shown in FIG. 30B. This cannula construction, generally designated by the numeral 625, also includes a central body portion 625*a* constructed of a microbore tubing, an enlarged diameter end portion 625*b*, and a needle-like extremity 625*c* which can be used for subdermal infusion of fluids into a patient. As in the construction shown in FIG. 30B, end portion 625*c* extends outwardly from the base of the device generally at right angles to the base so that it can penetrate the skin and tissue of the patient as the base is moved into proximity with the patient's body.

Like the cannula construction shown in FIG. 48, the enlarged diameter portion 625*b* of this latest form of hollow cannula also includes an outlet port 627 which is adapted to communicate with a fluid reservoir defined by an elastomeric membrane overlaying a base member.

As best seen by referring to FIGS. 50 and 50A, the flow control means, or filter member 630 of this form of the invention, is of a slightly different construction than that previously described and is closely received within a specially configured opening 632 provided in enlarged diameter portion 625*b*. More particularly, as shown in FIG. 50, flow control means, or member 630 includes a lower portion 630*a* which, when inserted into opening 632, engages the lower wall of the enlarged diameter portion 625*b* so as to impede fluid flow in a direction toward capillary tube portion 625*a*. As illustrated in FIG. 50A, due to the resistance of fluid flow through member 630, fluid introduced into the device via septum assembly 586 will tend to flow outwardly of the hollow cannula through port 627 and into the fluid reservoir of the device. However, as indicated by the arrow 634, in FIG. 50A, fluid flowing outwardly of the reservoir will flow through the flow control means or member 630 in the manner illustrated and toward capillary tube portion 625*a* of the hollow cannula.

It is also to be observed by referring to FIG. 49 that the outboard extremity 625*c* of the hollow cannula includes an enlarged diameter fluid flow passageway 636 which extends substantially the entire length of the perpendicularly extending portion 625*c* of the hollow cannula. This enlarged diameter fluid passageway permits a more rapid fluid flow through the extremity than does the capillary bore portion of the central body of the hollow cannula.

Turning to FIGS. 51 and 52, yet another form of hollow cannula of the invention is there illustrated. This hollow cannula is similar in some respects to that shown in FIG. 49, but includes a plurality of inner spirals which terminate in a needle-like, tissue-penetrating extremity also having an enlarged diameter fluid passageway 640. More particularly, this hollow cannula construction includes a central body portion 642 which spirals inwardly from the swagged end portion 644 of an enlarged diameter portion 646 of the hollow cannula and terminates at the generally perpendicularly extending needle-like extremity 648. Once again, flared portion 646*a* is provided with a cavity 650 which closely receives a flow control means or member 652.

FIG. 52 is a foreshortened, side-elevational, cross-sectional view of the cannula construction shown in FIG. 51, but illustrated in an uncoiled linear configuration. As indicated in FIG. 52, the central portion of the cannula is provided in the form of a microbore tubing having a small diameter microbore fluid passageway 655 which communicates with enlarged diameter fluid passageway 640 provided in extremity 648. As was the case in the earlier described hollow cannula constructions, enlarged diameter portion 646 is provided with a fluid outlet 657 which communicates with the fluid reservoir of the device within which the cannula is mounted. Like the earlier described forms of the invention, enlarged diameter portion 646*a* includes a flared end 646*a* which is adapted to receive a septum assembly of the character previously described.

Referring to FIGS. 53 through 60, still another form of the ultra low profile device of the invention is there shown and generally designated by the numeral 660. This latest embodiment of the invention is similar in some respects to the embodiment shown in FIGS. 34 through 37A. However, this embodiment is unique in that while it comprises a single fluid reservoir 664 disposed within a central chamber 665 it also includes dual ullages which are in communication. More particularly, the device includes a central conformable ullage 662, which is in a superior position to a central fluid reservoir 664 and a toroidal-shaped, conformable ullage 666. In a manner presently to be described, this construction permits the use of elevated pressures within chamber 665 without having to increase the overall height of the device.

As best seen in FIGS. 54 and 55, the apparatus here comprises a base 668 having an upper surface 670, including a central portion 670*a* and a peripheral portion 670*b* circumscribing central portion 670*a*. Base 668 is also provided with a lower surface 672. Formed within base 668 is a circuitous channel 674 (FIG. 53), which receives a portion of the infusion means, or serpentine-shaped hollow cannula 678, of the invention (FIG. 59).

The apparatus shown in FIGS. 53 through 60 also includes a barrier means for forming, in conjunction with the central portion 670*a* of the base, reservoir 664 which has an inlet port 680 and an outlet port 682. As best seen in FIG. 55, inlet port 680 is in communication with an outlet port 684 provided in an enlarged diameter portion 686 of cannula 678. Filling of fluid reservoir 664 is accomplished via a septum assembly 586 of the character previously described. As before, a flow control means or filter media 688 with fluid impermeable layer 688*a* impedes fluid flow toward the micro bore portion of the cannula and causes the fluid flowing into the enlarged diameter portion of the cannula via septum assembly 586 to flow through port 684 and toward reservoir 664.

Figure 53:
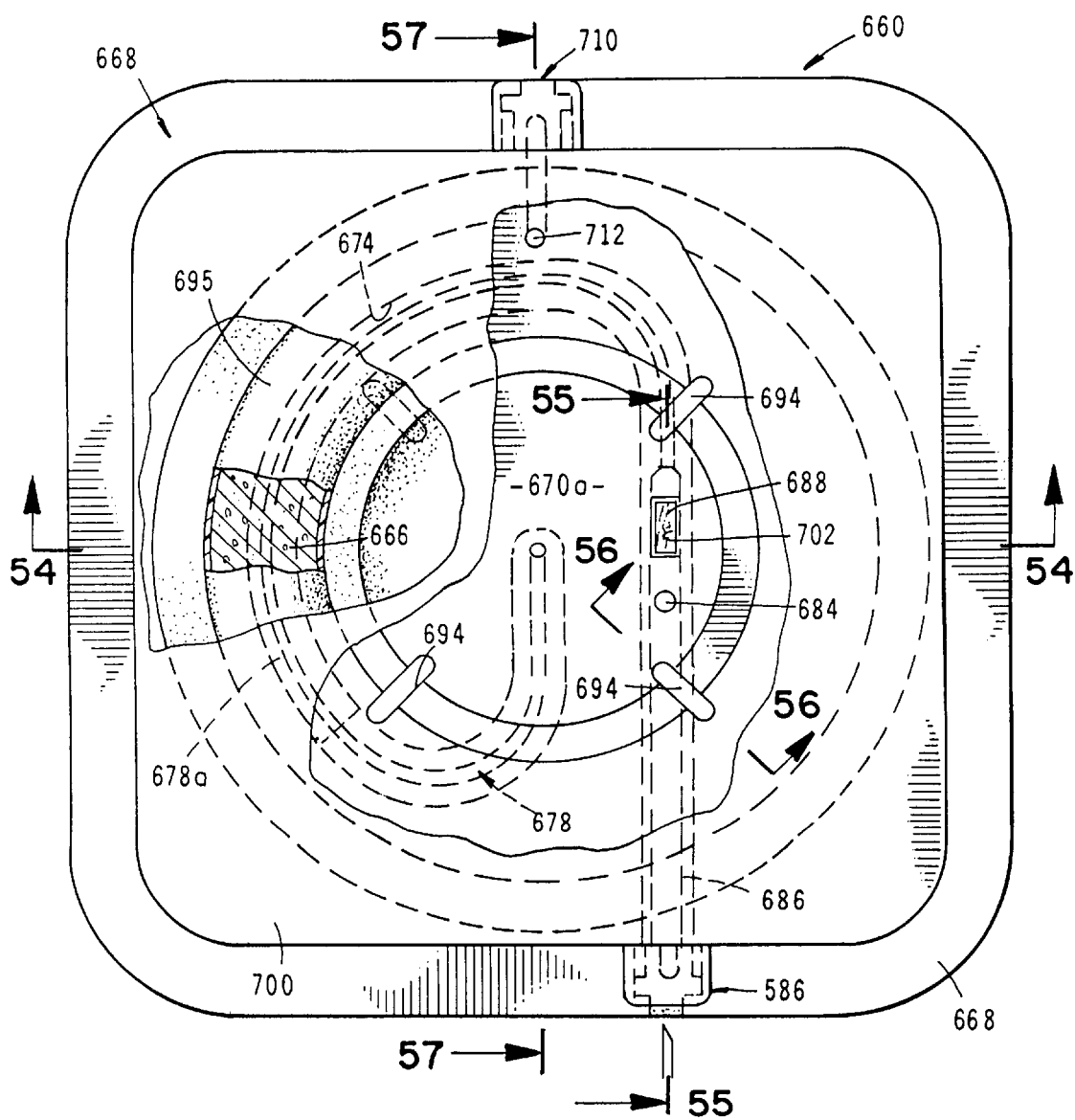
FIG. 53 is a top plan view of still another form of the low profile infusion apparatus of the invention partly broken away to show internal construction.
Figure 56:
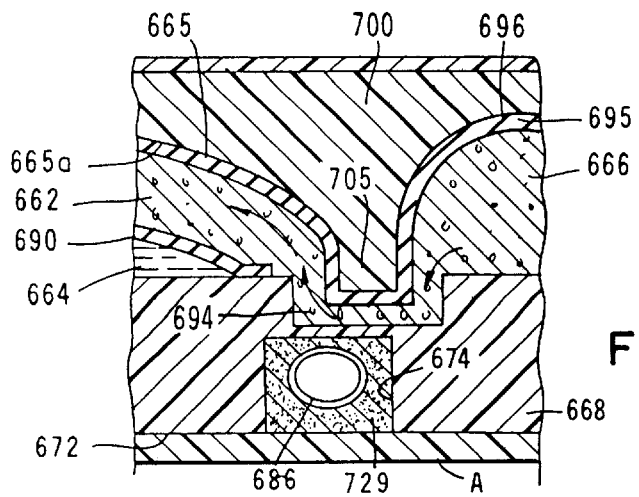
FIG. 56 is a cross-sectional view taken along lines 56—56 of FIG. 54

A stored energy means is provided in the form of at least one distendable membrane 695 which is superimposed over central portion 670*a* and peripheral parts 670*b* of the base. The central ullage 662 of the ullage defining means is disposed within chamber 665 for engagement with membrane 695 which, after being distended, will tend to return to its less distended configuration. As previously mentioned, the ullage defining means of this latest embodiment of the invention uniquely comprises not only the central conformable ullage 662, but also the outer toroidal shaped, conformable ullage 666 both of which vary in shape as the distendable membrane distends and, then, during the infusion step, tends to return to its less distended configuration. As best seen in FIGS. 53 and 56, the central conformable ullage 662 communicates with the outer toroidal ullage 666 via a plurality of passageways 694 which interconnect central chamber 665 with a toroidal-shaped chamber 696 which contains ullage 666. Ullages 662 and 666 here each comprise a flowable mass constructed from a gel material. Where, as is here the case, the conformable ullage comprises a flowable gel, an encapsulation barrier member 690 is used to cooperate in encapsulating the ullage medium. As best seen in FIG. 54, barrier member 690 comprises a single yieldably deformable membrane which overlays the central portion of the base and functions to define the fluid reservoir to be filled with the fluid to be delivered. On the other hand, the distendable barrier membrane 695 overlays the ullages and in its fully extended configuration closely conforms to the inner surface 665a of generally domed-shaped chamber 665 formed in cover 700 and to the inner surface 698 of toroidal chamber 696.

Figure 59:
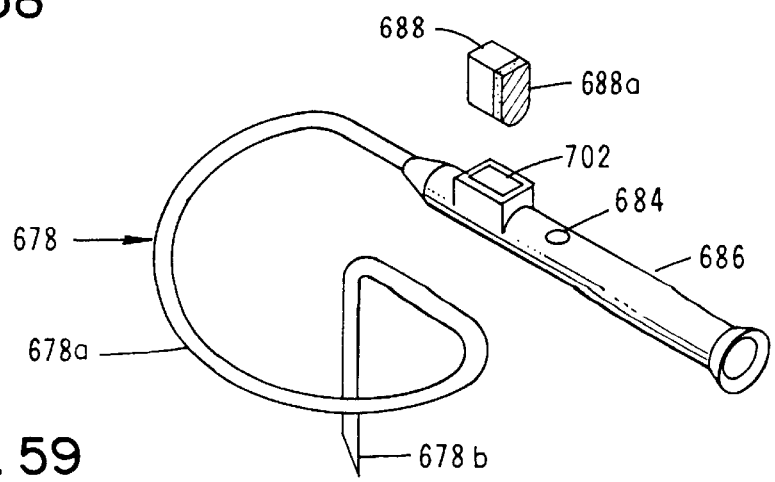
FIG. 59 is a generally perspective, exploded view of the capillary tube and flow control means of the form of the invention shown in FIGS. 53 through 58.

Turning particularly to FIGS. 53 and 59, the serpentine-shaped cannula 678 of the device includes a body portion 678a which is constructed from a length of microbore tubing, the previously identified enlarged diameter portion 686, and a needle-like outboard extremity 678b. Receivable within an opening 702 formed in portion 686 is the previously identified media for filtering fluids flowing from fluid reservoir 664. Filter 688 is preferably constructed from a porous material such a polysulfone.

As indicated in FIG. 54, cover 700 is provided with a tongue 705 and base 668 is provided with a mating groove 707 which clamp inboard portion 695a of the distendable membrane 695 in position relative to the base upon cover being brought into pressural engagement with base 668. Similarly, the outboard portion 695b of membrane 695 is clamped against the base upon joining the cover to the base by a sonic welding technique of the character previously described. Prior to joining the cover and the base the distendable membrane is bonded to the base along its periphery 690a in the manner shown in FIG. 54. When the cover and base are sealably joined together, conformable ullage 662 is captured between distendable membrane 695 and barrier membrane 690. In like fashion, conformable ullage 666 is captured between base portion 670b and the outer periphery of distendable member 695.

In using the apparatus of this latest form of the invention, chambers 664 and 666 are first partially filled with a suitable gel via septum assembly 710 (FIG. 60) using a conventional syringe assembly having a needle "N-1" adapted to penetrate septum 710a of septum assembly 710. During the gel filling step, the gel will flow first into toroidal chamber 666 via passageway 712 and then into central chamber 664 via circumferentially spaced passageways 694 (FIGS. 53 and 56). This done, fluid reservoir 664a can be filled via septum assembly 586 using a second syringe assembly containing the beneficial agent to be delivered to the patient. As the fluid chamber fills, conformable ullage 662 will conform to distendable membrane 695 causing the gel which comprises ullage 662 to be compressed. When chamber 664 reaches capacity, the gel contained therein can overflow into toroidal chamber 698 via passageways 694. With this construction elevated fluid pressures can be accommodated without having to increase the height of chamber 664 and, therefore, the overall height of the device. During the fluid expelling step, the gel can, of course, flow in the opposite direction from toroidal chamber 698 to central chamber 664 so as to conform to distendable membrane 695 as it tends to return toward its less distended configuration.

With chambers 664 and 698 filled with gel and with fluid reservoir 664a filled with the selected beneficial agent to be delivered to the patient, the device can be safely stored until time of use. At time of use, the novel needle protection means, or protective cover 720 can be broken away from base 668 along serration 722 (FIG. 57).

As best seen in FIG. 60, protective cover 720 is of unique design comprising a lower arcuate shaped sheath-like portion 724 which is separated from a connector portion 726 by serration 722. Sheath portion 724, sealably encloses the free floating end 678b of the hollow cannula while the upper top open, arcuately shaped segment 726a of the connector portion 726 is sealably receivable within an opening 727 formed in base 668. To hold the protective cover in place, an intermediate, flange-like segment 726b, which is integrally formed with segment 726a, is bonded to the lower surface 672 of the base by any suitable means such as adhesive bonding.

Figure 58:
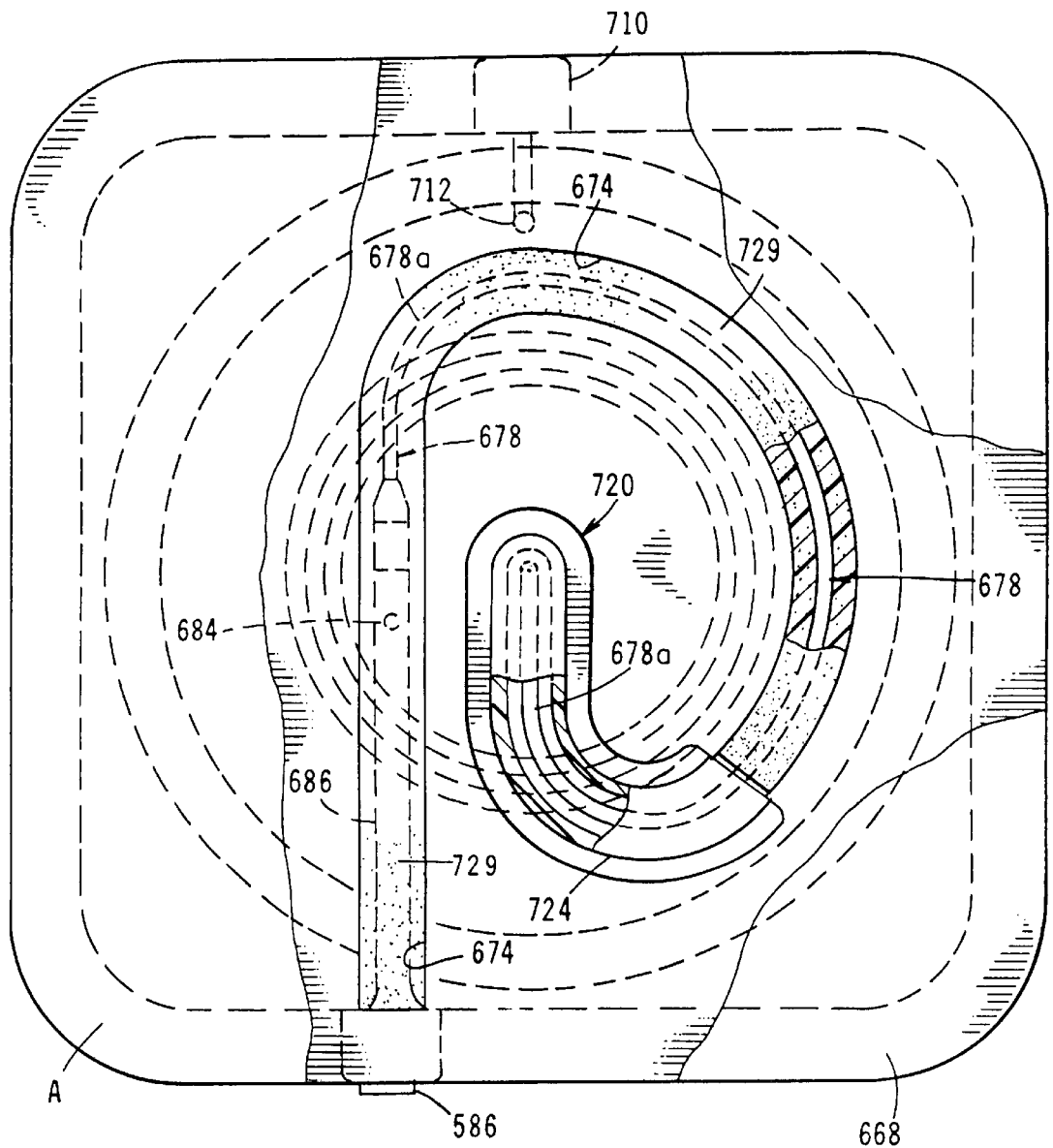
FIG. 58 is a bottom view of this latest embodiment, partly broken away to show internal construction.

Turning to FIGS. 57 and 58, it can be seen that part of the body portion 678a and enlarged diameter portion 686 of spiral cannula 678 is uniquely supported within channel 674 of base 668 by a cannula encapsulation means shown here as a standard potting compound 729. Compound 729 rigidly supports the body portion of the cannula within channel 674 and dynamically supports the outer extremity 678b of the cannula so that the spring-like outer extremity is free to move three dimensionally within segment 726a. With this highly novel construction, when the device is connected to the patient with the needle portion 678b of the cannula penetrating the patient's body, as, for example, the patient's arm or leg, normal movement by the patient will permit the cannula to move within segment 726a and within the outer portions of channel 674 while the base remains completely stationary. Without this important feature, normal movements by the patient causing flexing of the muscle and tissue would impart loosening forces to the device which, in time, could cause the adhesive pad "A" provided on the base of the device to separate from the patient's skin.

Referring to FIGS. 61 through 66, another form of the ultra low profile device of the invention is there shown and generally designated by the numeral 770. As best seen by referring to FIGS. 61, 62, and 63, this embodiment of the invention is similar in some respects to that shown in FIGS. 43 through 48A save that the filling means is located in a different location and the device includes a highly novel hydrogel film rate control device the character of which will presently be described.

As best seen in FIGS. 61 and 63, the apparatus here comprises a base 772 having an upper surface 774, including a central portion 774a and a peripheral portion 774b circumscribing central portion 774a. Base 772 is also provided with a lower surface 776. Formed within base 772 is an inlet passageway 778 and an outlet passageway 780.

As before, this latest form of the invention includes a stored energy means for forming, in conjunction with the base 772, a generally toroidal-shaped fluid reservoir 782 which is in communication with outlet passageway 780. As best seen in FIG. 63, reservoir 782 is also in communication with an inlet passageway 778 which, in turn, is in communication with a septum assembly 786. Filling of reservoir 782 is accomplished in the manner previously described via septum assembly 786, which is of similar construction to the septum assemblies previously described herein, and includes a pierceable septum 786a that is pierceable by a syringe needle "N".

Once again, the stored energy means comprises at least one distendable membrane 796 which is superimposed over base 742. An ullage defining means is disposed within a generally toroidal chamber 792 defined by an inner surface 792a formed in a cover 793. Chamber 792 also contains fluid reservoir 782 which is disposed between the inner surface of membrane 788 and the upper surface 774 of the base. The ullage defining means here comprises a conformable ullage 794 which is interposed between membrane 796 and a yieldably deformable barrier membrane 788. As before distendable membrane 796 will distend outwardly upon fluid being introduced into reservoir 782 and, after being distended, will tend to return to its less distended configuration. Conformable ullage 794 is of the same general character as previously described herein and is made up of a deformable mass which uniquely conforms to the shape of the distendable membrane as the membrane distends and as it tends to return to its less distended configuration. As encapsulation barrier membrane 788 expands, ullage 794 will pressurally engage membrane 796 urging it outwardly into engagement with surface 792a of cover 793. Distendable membrane 796, which is elastically deformable, can be constructed from various materials including polyurethane, silicone, flurosilicone and synthetic rubber.

In the manner previously described, cover 793 is receivable over base 772 and, as shown in FIG. 66, includes a capture groove 796 and an adjacent tongue 798. Similarly, base 772 is provided with tongue 800 which mates with groove 796 as the cover moves into engagement with base 772. As before, base 772 is also provided with an upstanding membrane cutting means, or protuberance 802 which functions to cleanly cut the stored energy means and the barrier membrane upon the cover being brought into pressural engagement with base. With this construction, following cutting of the membrane, the cover can be sonically welded to the base.

When the cover and base are sealably joined together, a reservoir inlet port 804 communicates with inlet passageway 778, while a reservoir outlet port 806 communicates with outlet passageway 780. In order to precisely control the rate of fluid flow outwardly of outlet port 806, rate control means in the form of the previously mentioned hydrogel rate control device 807 is interposed between reservoir 782 and outlet port 806. Rate control 807 is constructed from a hydrogel film that swells upon imbibing fluid entering reservoir 782 and, in its swollen condition, precisely regulates the rate of fluid flow toward outlet passageway 780 and then outwardly of the device through a delivery luer assembly 810 of a character well known in the art. To collect fluid flowing through rate control 807 a fluid collection cavity 812 is formed in base 772 directly below outlet 806.

In using the apparatus of this latest form of the invention, reservoir 782 can be filled via septum assembly 786 using a conventional fluid containing syringe assembly having a needle "N" adapted to penetrate septum 786a of septum assembly 786. During filling any gases contained within the chamber defined by inner surface 792a of cover 793, will be vented to atmosphere via porous plugs 814 provided in vent apertures 816 formed in cover 793 (FIG. 65). With the reservoir thus filled, a cover 818, which covers the outlet end of luer assembly 810, can be removed and fluid delivered to the patient in a conventional manner well known in the art. As before, the base of the device is provided with a suitable adhesive pad 811 to enable the device to be removably affixed to the patient's body such as to the arm or leg of the patient.

Turning next to FIGS. 67 through 71, still another form of the ultra low profile infusion device of the invention is there shown and generally designated by the numeral 830. This latest embodiment of the invention is similar in some respects to the embodiment shown in FIGS. 53 through 59 in that it also comprises a single fluid reservoir 832 disposed within a central chamber 834 formed in a cover 835 and includes a plurality of conformable ullages which are in communication (FIG. 69). More particularly, the device includes a central conformable ullage defining means, or first conformable mass 836 which is in an inferior position to central fluid reservoir 832 and a toroidal-shaped, conformable ullage defining mass, or second conformable mass 838 circumscribing ullage 836. This construction permits the use of elevated pressures within chamber 834 without having to increase the overall height of the device.

Figure 68:
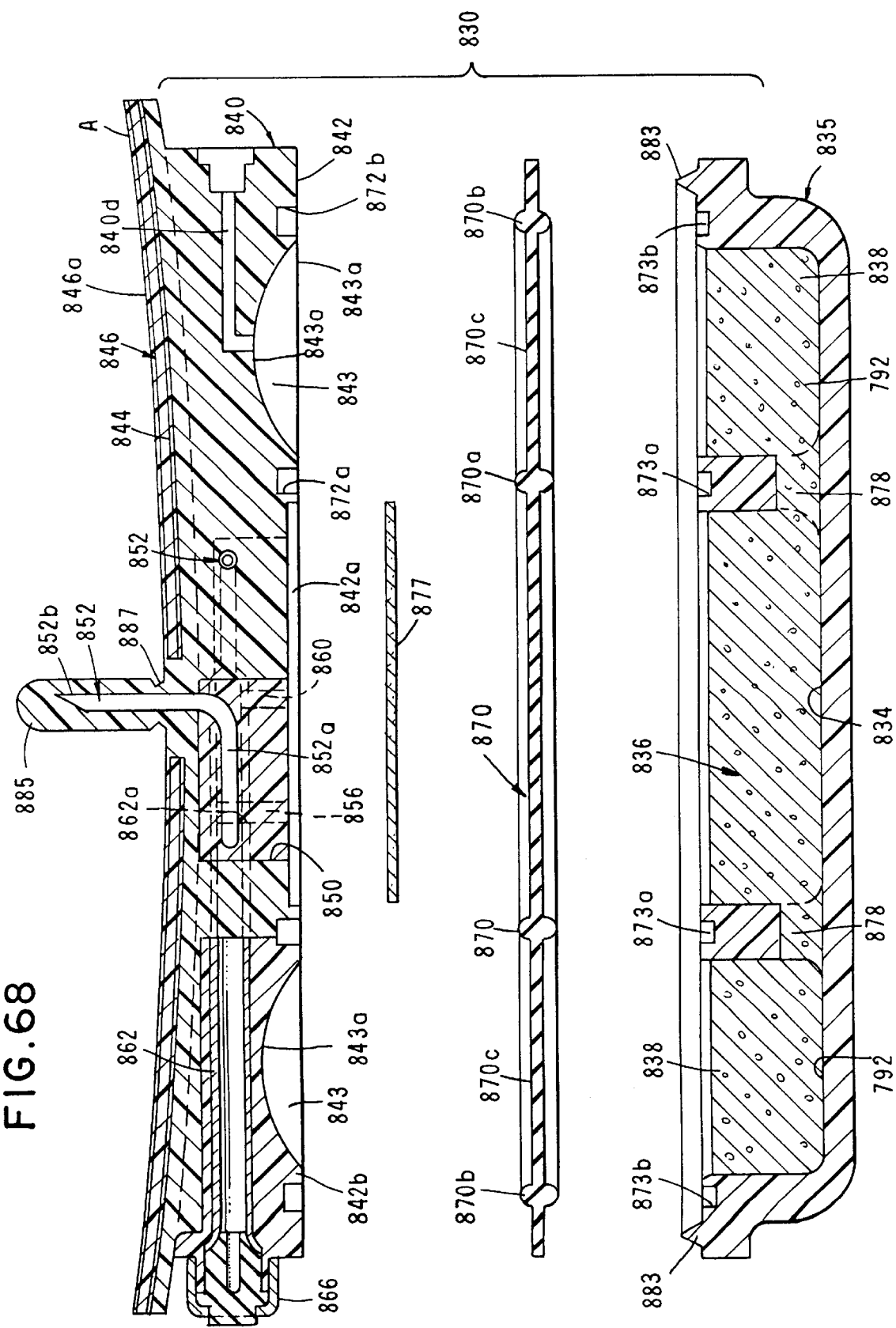
FIG. 68 is an exploded, cross-sectional view of this latest form of the invention showing the base portion superimposed over the separation membrane, the distendable membrane and the cover of the apparatus.

As best seen in FIGS. 67, 68 and 69, the apparatus here comprises a base 840 having a first surface 842, including a central portion 842a and a peripheral portion 842b circumscribing central portion 842a. Peripheral portion 842b includes a concave surface 843a which defined a generally toroidal-shaped expansion channel or groove 843 formed within base 840. Base 840 is also provided with a second surface 844 to which an adhesive pad assembly 846 is affixed. After a peal strip 846a is removed from the pad assembly to expose an adhesive layer "A", the device can be conveniently affixed to the patient's body. Formed within base 840 is a circuitous channel 850 (FIG. 67), which receives a portion of the infusion means, or serpentine-shaped hollow cannula 852, of the invention.

The apparatus shown in FIGS. 67 through 71 also includes a uniquely configured stored energy means for forming, in conjunction with the central portion 842a of the base, the fluid reservoir 832. Fluid reservoir 832 has an inlet port 856 and an outlet port 860. Inlet port 856 is in communication with an outlet port 862a which is provided in an enlarged diameter portion 862 of cannula 852. Filling of fluid reservoir 832 is accomplished via a septum assembly 866 of the character previously described having a pierceable septum 866a (FIG. 71). As before, a flow control means comprises the micro bore portion 852a of the cannula.

The stored energy means is here provided in the form of a generally planar distendable membrane 870 which overlays surface 842 of the base. Membrane 870 includes an inner O-ring like protuberance or portion 870a and a radially spaced, outer O-ring like protuberance portion 870b. These O-ring like protuberances form a part of the sealing means of the invention for sealably interconnecting base 840 and cover 835 and are sealably received within generally circular-shaped, radially spaced inner and outer O-ring grooves 872a and 872b formed in surface 842 of base 840 (see FIGS. 67 and 68). Grooves 872a and 872b also form a part of the sealing means of the invention. When the apparatus is assembled in the manner shown in FIG. 69, membrane 870 spans central portion 842a as well as the circumferentially extending grooved outer portion 842b of base 840. The inner and outer O-ring like protuberances are also sealably receivable within O-ring grooves 873a and 873b which are formed in cover 835 and which also comprise a part of the sealing means of the invention. Materials suitable for use in constructing the base, the cover and the distendable membrane are discussed in detail in U.S. Pat. No. 5,205,820 (FIG. 68).

Disposed within a generally circular shaped recess 875 formed in base 840 is a barrier means or separation membrane 877 which prevents fluid within fluid chamber 832 from contacting distendable membrane 870. Membrane 877 can be formed from any suitable elastomeric material such as polyurethane, silicone or synthetic rubber.

With the construction shown in FIG. 69, the central or first conformable mass 836 of the ullage defining means is disposed within chamber 834 for engagement with membrane 870 which, after being distended, will tend to return to its less distended configuration. As was the case with the previously discussed embodiment shown in FIGS. 53 through 59), the ullage defining means of this latest embodiment of the invention comprises not only the central conformable ullage 836, but also the outer toroidal shaped, conformable ullage 838. Both of the conformable masses 836 and 838 are uniquely covered by distendable membrane 870 and both continuously vary in shape as the distendable membrane distends outwardly from the base (FIG. 69).

A unique feature of this latest embodiment of the invention results in the fact that the first conformable mass ullage 836 communicates with the second outer toroidal-shaped mass 838 via a plurality of passageways 878 which interconnect the first or central chamber 834 formed in cover 835 with the second toroidal-shaped chamber 792 formed in cover 835 (FIG. 69). As before, conformable masses 836 and 838 preferably comprise a deformable, flowable mass constructed from a suitable gel material. Accordingly, in a manner presently to be described, the gel which makes up first conformable mass 836 can expand into chamber 792 formed in cover 835 via passageways 878 as the distendable membrane 870 distends outwardly during filling of fluid chamber 832.

Turning particularly to FIGS. 67, 68 and 69, the serpentine-shaped cannula 852 of the device includes the previously identified enlarged diameter portion 862 and the microbore portion 852a which terminates in a needle-like outboard extremity 852b. As best seen in FIG. 70, the enlarged diameter portion 862 of the cannula is held in position within channel 850 by a potting compound 422 of the character previously described.

Turning particularly to FIG. 68, it can be seen that cover 835 is provided with an upstanding protuberance 883 which permits joining of the cover 835 to the base 840 by a sonic welding technique of the character previously described. Prior to joining the cover and the base and, prior to positioning the distendable membrane over the cover, chambers 834 and 792 are filled with gel. Also, barrier membrane 877 is, at this time, appropriately bonded to the base along its periphery by adhesive bonding or like techniques well known to those skilled in the art. When the cover and base are sealably joined together, the O-ring protuberances 870a and 870b are guided into sealable engagement with grooves 872a and 872b respectively so as to seal distendable membrane 870 relative to the base. If desired, a suitable adhesive can be placed within grooves 872a and 872b to bond the O-ring-like portions 870a and 870b to the base to enhance sealing. After the cover and base have been interconnected, conformable ullages 836 and 838 are sealably captured between distendable membrane 870 and the inner surfaces of cover 835 which define chambers 834 and 792.

Following the interconnection of base 840 with cover 835 in the manner described in the preceding paragraphs, fluid reservoir 832 can be filled via septum assembly 866 using a suitable syringe assembly containing the beneficial agent to be delivered to the patient. As the fluid chamber fills, conformable mass 836 will conform to the central portion of the distendable membrane in the manner shown in FIG. 69 causing the gel which comprises mass 836 to be forced inwardly and to overflow into the second toroidal-shaped chamber 792 via passageways 878. As the gel flows under pressure into chamber 792, the outer peripheral portion 870c of distendable membrane 870 will deform toward concave surface 843a and into base channel 843 permitting this channel to, at least, partially fill with gel. As the peripheral portion 870c of the distendable membrane 870 distends into channel 843, any gases contained therein will be vented to atmosphere via vent means which here comprises a passageway 840d and a vent plug 879 (see FIG. 69). With this novel construction, elevated fluid pressures within the fluid chamber 834 can readily be accommodated without having to increase the height of the chamber and, therefore, the overall height of the device. During the fluid expelling step, the gel can, of course, flow in the opposite direction from toroidal-shaped chamber 792 into first or central chamber 834 so as to conform to distendable membrane 870 as it tends to return toward its less distended configuration.

With chambers 834 and 792 filled with gel and with fluid reservoir 832 filled with the selected beneficial agent to be delivered to the patient, the device can be safely stored until time of use. At time of use, the novel needle protection means, or protective cover 885 can be broken away from base 840 along serration 887 (FIG. 69) and removed from the cannula thereby permitting fluid to flow outwardly of cannula end 852b.

Figure 72:
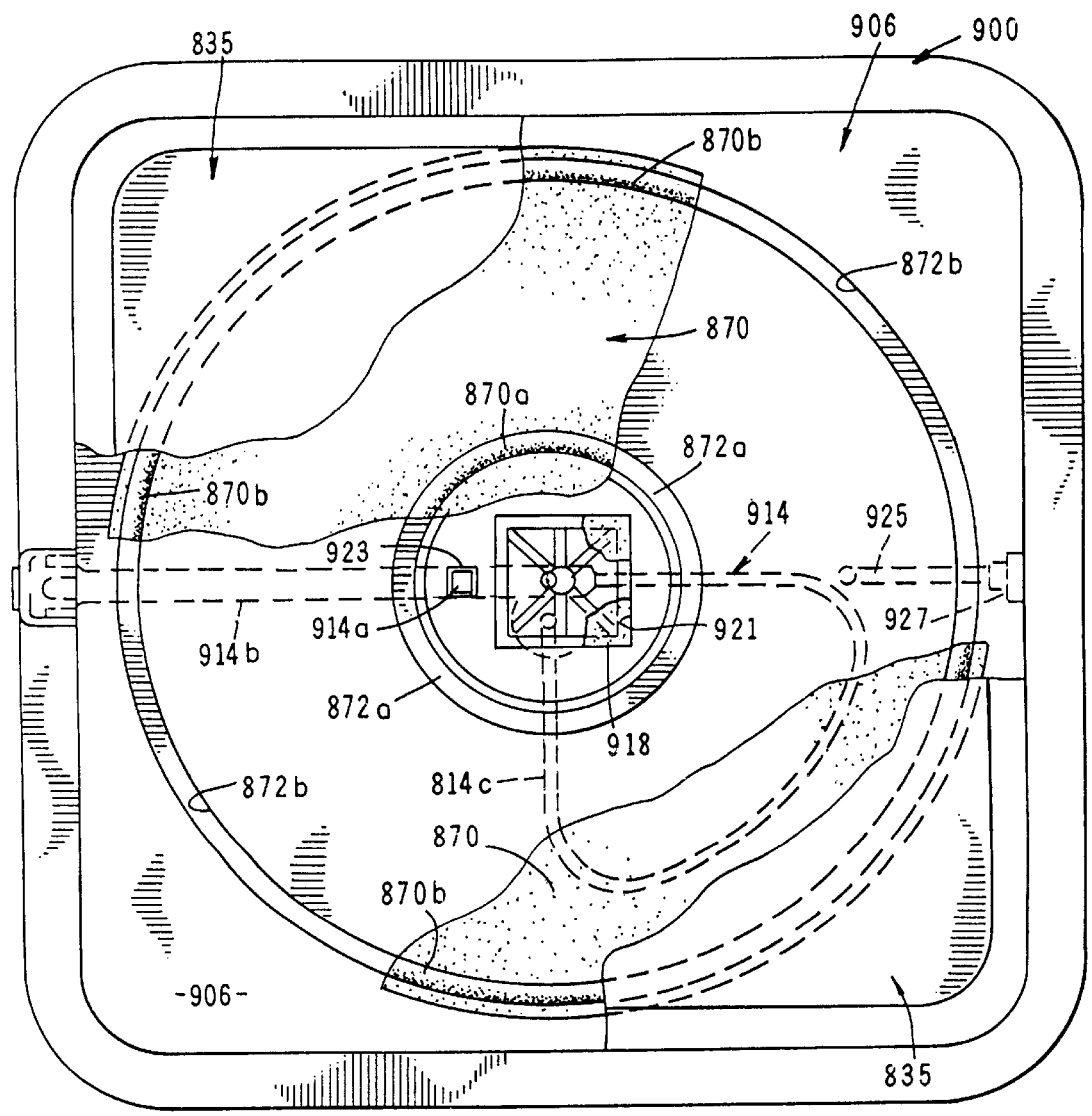
FIG. 72 is a top plan view of the base portion of yet another form of the low profile infusion apparatus of the invention partly broken away to show internal construction.
Figure 73:
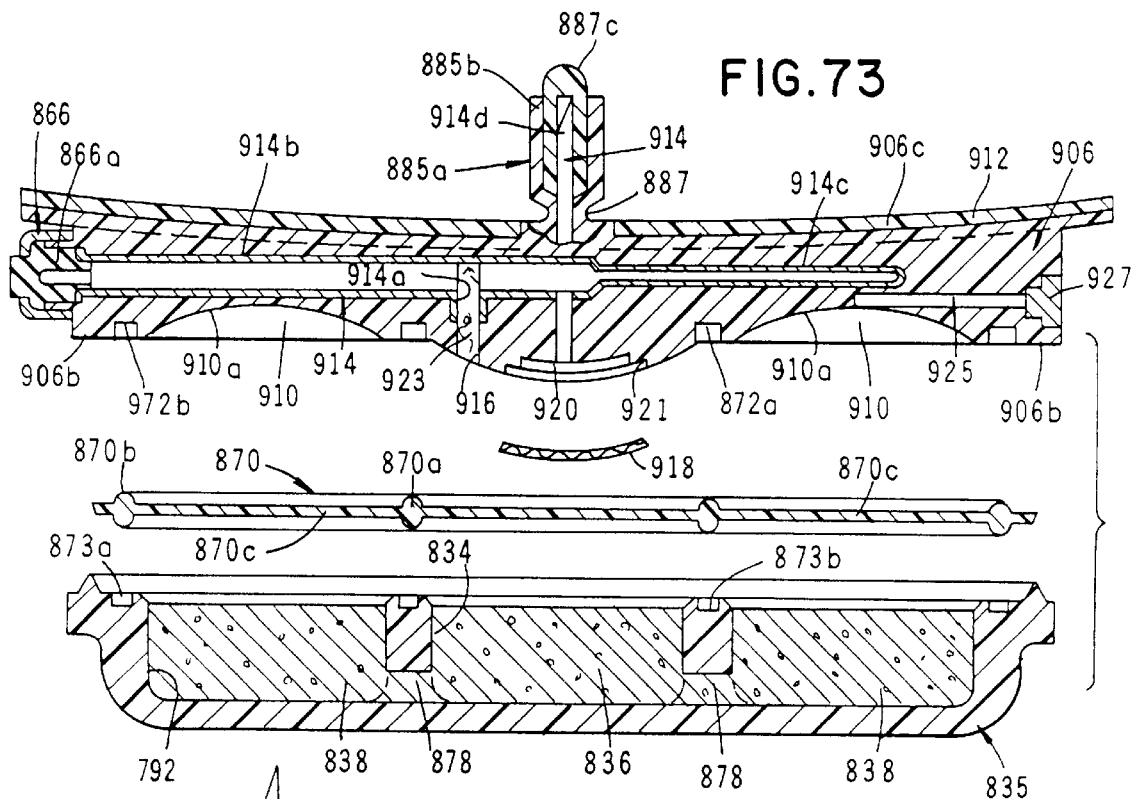
FIG. 73 is an exploded, cross-sectional view of the form of the invention shown in FIG. 72 illustrating the base portion superimposed over the rate control device, the distendable membrane, and the cover of the apparatus.
Figure 74A:
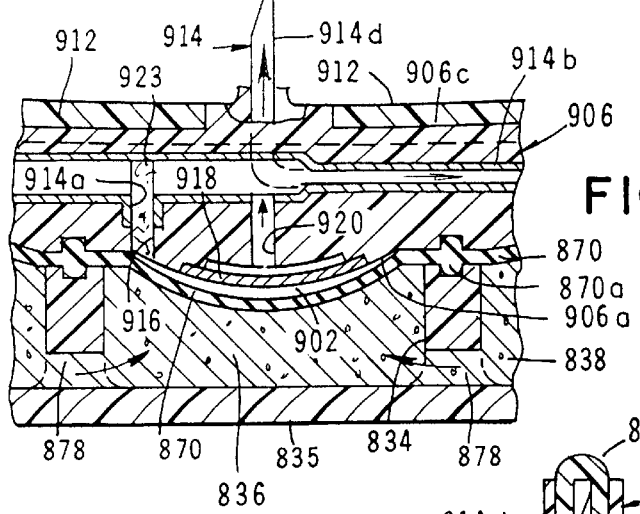
FIG. 74A is a fragmentary, cross-sectional view similar to FIG. 74, but showing fluid being expelled from the fluid reservoir of the device.
Figure 74:
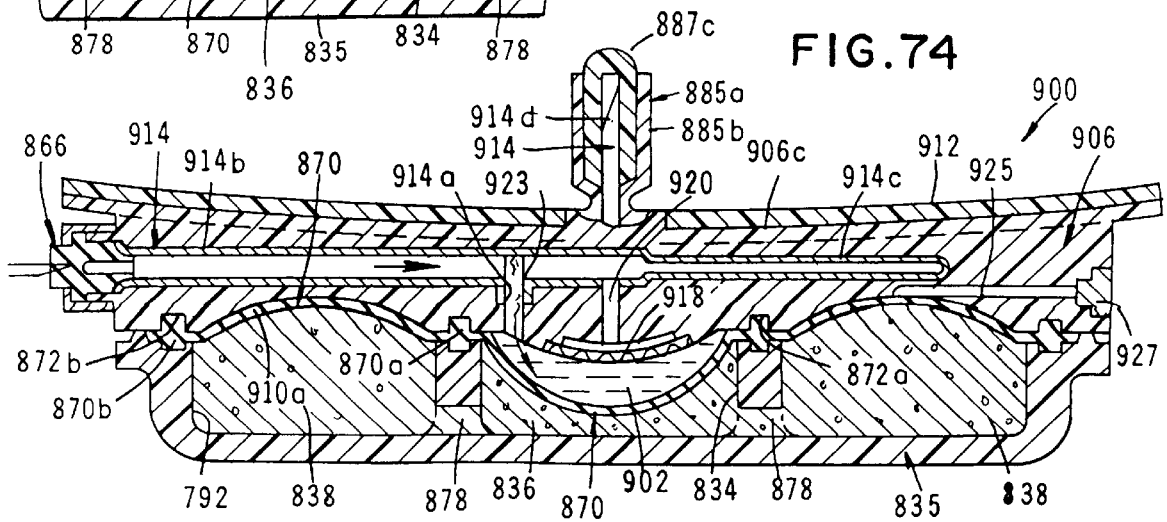
FIG. 74 is a cross-sectional view of the apparatus of FIG. 73 shown in an assembled configuration.

Referring now to FIGS. 72, 73, and 74, another form of the ultra low profile infusion device of the invention is there shown and generally designated by the numeral 900. This latest embodiment of the invention is similar in many respects to the embodiment shown in FIGS. 67 through 71 and like numbers are used to identify like components. This latest embodiment of the invention comprises a single fluid reservoir 902 (FIG. 74) disposed within a first central chamber 834 formed in a cover 835 which is identical to that previously described and includes conformable masses 836 and 838 of the character previously described which are in communication via passageways 878.

As best seen in FIGS. 73 and 74, base 906 of this embodiment is of a slightly different construction having a central, generally convex surface 906a and a peripheral portion 906b which includes a concave surface 910a which defines a generally toroidal-shaped expansion channel or groove 910 formed within base 906. In this latest form of the invention, convex portion 906a, in cooperation with the conformable masses 836 and 838, comprise the ullage means of the invention. As before, base 906 has a surface 906c to which an adhesive pad assembly 912 is affixed. Integrally molded within base 906 is a serpentine-shaped hollow cannula 914, which comprises a part of the infusion means of this form of the invention.

The apparatus shown in FIGS. 72 through 74 includes a uniquely configured stored energy means identical to that described in connection with the embodiment shown in FIGS. 67 through 71 and forms, in conjunction with the central portion 906a of the base, the fluid reservoir 902. Fluid reservoir 902 has an inlet port 916 and an outlet port 920. Inlet port 916 is in communication with an outlet port 914a which is provided in an enlarged diameter portion 914b of cannula 914. Filling of fluid reservoir 902 is accomplished via a septum assembly 866 of the character previously described having a septum 866a.

In this latest form of the invention, flow control means comprises both a uniquely shaped hydrogel rate control device 918 as well as the micro bore portion 914c of the cannula. Rate control device 918 is held in place within a recess 921 formed in base 906 by any suitable means such as adhesive bonding. In use, the hydrogel rate control device swells upon imbibing fluid and functions to precisely control the rate of fluid flow from reservoir 902.

As in the earlier described form of the invention, the stored energy means or membrane 870, overlays the base and includes an inner O-ring like protuberance 870a and a radially spaced, outer O-ring like protuberance 870b. These O-ring like protuberances are sealably received within generally circular-shaped, radially spaced inner and outer O-ring grooves 872a and 872b formed in base 906 (see FIGS. 73 and 74). As before, grooves 872a and 872b also form a part of the sealing means of the invention. When the apparatus is assembled in the manner shown in FIG. 74, membrane 870 spans the central portion of the base as well as the circumferentially extending grooved outer portion 906b. The inner and outer O-ring like protuberances are also sealably receivable within O-ring grooves 873a and 873b formed in cover 835 (FIG. 73) and which comprise a part of the sealing means of the invention.

In the construction shown in FIG. 74, the central convex portion 906a of the base forms the rigid ullage portion of the ullage means and ullage portions 836 and 838 form the conformable ullage portions of the ullage means. As before, the conformable ullage portions of the ullage means are covered by distendable membrane 870 and both continuously vary in shape as the distendable membrane distends outwardly from the base as fluid is introduced into reservoir 902 via the septum assembly. Once again, central conformable ullage 836 communicates with the outer toroidal ullage 838 via passageways 878 so that, as fluid chamber 902 is filled, the gel which makes up the central ullage is engaged by membrane 870 urging it outward and causing it to flow into chamber 792 of cover 835. This causes the gel contained within this chamber to, in turn, expand, along the membrane 870 into channel 910 formed in base 906 in the manner shown in FIG. 74.

Figure 72A:
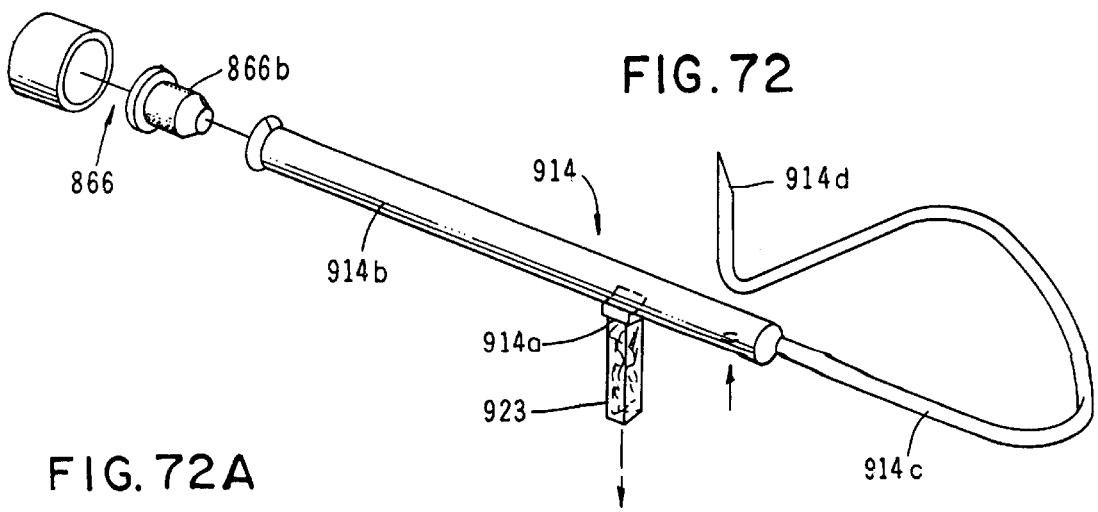
FIG. 72A is a generally perspective view of the cannula and septum assembly of this latest form of the invention.

Turning particularly to FIGS. 72, 72A, and 73, the serpentine-shaped cannula 914 of the device there illustrated includes the previously identified enlarged diameter portion 914b and the microbore portion 914c which terminates in a needle-like outboard extremity 914d. Cannula 914 is molded in place with a base 906 in a manner well known by those skilled in the art. Extremity 914d is protected by a protective cover 885a which is similar to the previously discussed cover 885. However, cover 885a includes an outer sheath 885b which is connected to the base along a serration line 887. Sheath 885b telescopically receives a removable plug 887c which closely surrounds extremity 914d of the cannula.

Prior to joining the cover and the base as by sonic welding and, prior to positioning the distendable membrane over the cover, chambers 834 and 792 are filled with gel. Also, rate control device 918 is, at this time, emplaced into cavity 921. When the cover and base are sealably joined together, the O-ring portions 870a and 870b are guided into sealable engagement with grooves 873a and 873b respectively so as to seal distendable membrane 870 relative to the base. If desired, a suitable adhesive can be placed within grooves 872a and 872b to bond the O-ring-like portions 870a and 870b to the base to enhance sealing. After the cover and base have been interconnected, conformable ullages 836 and 838 are sealably captured between distendable membrane 870 and the inner surfaces of cover 835 which define chambers 834 and 792.

Following the interconnection of base 906 with cover 835 in the manner described in the preceding paragraphs, fluid reservoir 902 can be filled via septum assembly 866 using a suitable syringe assembly containing the beneficial agent to be delivered to the patient. Filter means, shown here as a porous filter member 923, filters the fluid flowing out of outlet 914a. Filter 923 can be constructed from any suitable filter material such as a polycarbonate. As the fluid chamber fills, the peripheral portion 870c of the distendable membrane 870 will distend into channel 910, and any gases contained therein will be vented to atmosphere via passageway 925 and vent plug 927 (see FIG. 74). During the fluid expelling step, the gel can, of course, flow in the opposite direction from toroidal chamber 792 into central chamber 834 so as to conform to distendable membrane 870 as it tends to return toward its less distended configuration.

Turning next to FIGS. 75 through 79, still another form of the ultra low profile infusion device of the invention is there shown and generally designated by the numeral 950. This latest embodiment of the invention is somewhat similar to the embodiment shown in FIGS. 72 through 74 and like numbers are used to identify like components. This latest embodiment of the invention uniquely comprises a dual chamber fluid reservoir 952 (FIG. 76) which extends into a central chamber 954 formed in a cover 956 which is similar to that previously described. However, central chamber 954 is slightly larger to accommodate the dual chamber fluid reservoir. As before, cover 956 contains a plurality of conformable masses of the character previously described which are in communication via passageways 957.

As best seen in FIGS. 75 and 76, base 960 of this embodiment is of a slightly different construction having first and second filling means for separately filling the dual reservoirs 952a, and 952b. Like the earlier described embodiment, base 960 has a central, surface 960a and a peripheral portion 960b which includes a generally toroidal-shaped expansion channel or groove 962 formed within base 960 and defined by concave surface 962a. In this latest form of the invention, portion 960a is generally planar in shape. Base 960 also has a surface 960c to which an adhesive pad assembly 964 is affixed. Integrally molded within base 960 is a uniquely-shaped hollow cannula 966 (FIG. 79), which comprises a part of the infusion means of this form of the invention.

The apparatus shown in FIGS. 75 through 77 includes a uniquely configured stored energy means very similar to that previously described and, in conjunction with the central portion 960a of the base, forms the two fluid reservoirs 952a and 952b. As best seen in FIGS. 75, 76, and 77, fluid reservoir 952a has an inlet port 968 and an outlet port 970. Similarly, fluid reservoir 952b has an inlet port 972 and an outlet port 974. Outlet ports 970 and 974 communicate with inlet ports 975 and 977 respectively provided in enlarged diameter portion 966a of cannula 966 (FIG. 79). Filling of reservoir 952a is accomplished via a first septum assembly 980 of the character previously described, while fluid reservoir 952b is filled via septum assembly 982. As best seen in FIG. 78, each of the septum assemblies communicate with an elongated tubular member "T" which terminates at its reduced diameter end at the inlets of fluid reservoirs 952a and 952b.

In this latest form of the invention, flow control means are provided in the form of first and second rate control members 983 and 984 respectively which are disposed within cavities 983a and 984a formed in base 960 proximate outlets 970 and 974. Members 983 and 984 are preferably constructed from a polycarbonate material.

As in the earlier described form of the invention, the stored energy means or membrane 986, overlays the base and includes an inner O-ring like protuberance 986*a* and a radially spaced, outer O-ring like protuberance 986*b*. These O-ring like protuberances are sealably received within generally circular-shaped, radially spaced inner and outer O-ring grooves 987*a* and 987*b* formed in base 960 (see FIG. 75A). When the apparatus is assembled in the manner shown in FIG. 76, membrane 986 spans the central portion of the base as well as the circumferentially extending grooved outer portions 960*b*. The inner and outer O-ring like protuberances are also sealably receivable within O-ring grooves 989*a* and 989*b* formed in cover 956 (FIG. 75A).

Provided in the construction shown in FIGS. 75 and 77, is a highly novel barrier or separation means, shown here as a yieldable separation membrane 990. As best seen in FIG. 75, membrane 990 is bonded to the base along the peripheral portions "P" thereof and along a central dividing line "L" that divides the membrane into first and second portions 990*a* and 990*b*. More particularly, the membrane is bonded to the base along the bond areas designated generally as 991. Areas 991*a* circumscribe central portion 960*a* while area 991*b* bisects the central portion. With this novel construction, as fluid under pressure is introduced into the device via the first and second filling means, both the stored energy membrane 986 and the barrier membrane 990 will deform outwardly in the manner shown in FIG. 76 to form the two fluid reservoirs.

As before, the ullage means are covered by distendable membrane 986 and both continuously vary in shape as the distendable membrane distends outwardly from the base as fluid is introduced into reservoirs 952*a* and 952*b* via septum assemblies 980 and 982. Once again, the central conformable ullage or mass 994 communicates with the outer toroidal ullage or mass 995 via passageways 957 so that, as fluid chambers 952*a* and 952*b* are filled, the mass which makes up the central ullage contained within central chamber 954 is engaged by membrane 986 urging it outward and causing it to flow into toroidal chamber 956*b* of cover 956. This causes the mass contained within this chamber along with membrane 986 to, in turn, expand into channel 962 formed in base 960 in the manner shown in FIG. 76. As before, gases contained in this channel will be vented via passageway 925 and vent plug 927. As the fluid is expelled from the reservoirs, the gel-like masses will return to the central chamber in the manner shown in FIG. 77A.

Turning particularly to FIGS. 77 and 79, the uniquely-shaped cannula 966 of the device there illustrated includes the previously identified enlarged diameter portion 966*a* and the smaller diameter portion 966*b* which terminates in a needle-like outboard extremity 966*c*. Cannula 966 is molded in place with a base 960 in a manner well known by those skilled in the art.

Prior to joining the cover and the base as by adhesive bonding or sonic welding and, prior to positioning the distendable membrane over the cover, chambers 954 and 956*b* are filled with the gel which comprises the conformable masses 994 and 995. Also, rate control membranes 983 and 984 are, at this time, emplaced into cavities 983*a* and 984*a* and barrier membrane 990 is adhesively bonded to base 960 along bond areas 991*a* and 991*b*. When the cover and base are sealably joined together, the O-ring protuberances 986*a* and 986*b* are guided into sealable engagement with grooves 987*a* and 987*b* respectively so as to seal distendable membrane 986 relative to the base. If desired, a suitable adhesive can be placed within the grooves to bond the O-ring-like protuberances to the base and to the cover to enhance sealing. After the cover and base have been interconnected, conformable ullages 994 and 995 are sealably captured between distendable membrane 986 and the inner surfaces of cover 956 which define chambers 954 and 956*b*.

Following the interconnection of base 960 with cover 956 in the manner described in the preceding paragraphs, fluid reservoir 952*a* can be filled via septum assembly 980 using a suitable syringe assembly containing the beneficial agent to be delivered to the patient. As the fluid is introduced via septum assembly 980 and tube "T", it will impinge upon portion 990*a* of membrane 990 causing it, along with a portion of distendable membrane 986, to distend outwardly to form reservoir 952*a*. In similar fashion, fluid reservoir 952*b* can be filled via septum assembly 982. Once again, as fluid is introduced into the device via septum assembly 982, and tube "T" it will impinge upon portion 990*b* of membrane 990 causing it, along with a portion of distendable membrane 986, to distend outwardly to form reservoir 952*b*. As the central portions of the distendable membrane 986 thusly extends outwardly, the peripheral portion thereof will extend into channel 962 in the manner shown in FIG. 76. Fluid flowing into reservoirs 952*a* and 952*b* will be filtered by filter means shown here as porous filter "F" which are carried within tubes "T".

As fluid is expelled from reservoirs 952*a* and 952*b* in the manner shown in FIG. 77A, the central portion of the distendable membrane will move toward the central portion of the base causing fluid to flow into inlet ports 975 and 977 of the cannula via rate controls 983 and 984. At the same time, the peripheral portion of the distendable membrane will cause conformable mass 995 to flow toward central chamber 954 in the manner shown in FIG. 77*a*.

Turning next to FIGS. 80 through 87, another form of the ultra low profile infusion device of the present invention is there shown and generally designated by the numeral 1000. This latest embodiment of the invention is similar in some respects to the embodiment shown in FIGS. 67 through 71, but comprises a sealing means of different construction for sealably interconnecting the distendable membrane with the base and with the cover. This latest form of the invention also comprises a single fluid reservoir 1002 disposed within a central chamber 1004 formed in a cover 1005 and includes a plurality of conformable ullages which are in communication (FIG. 86). More particularly, the device includes a central conformable ullage defining means, or first conformable mass 1006 which is in an inferior position to central fluid reservoir 1002 and a toroidal-shaped, conformable ullage defining mass, or second conformable mass 1008 circumscribing ullage 1006.

As best seen in FIGS. 83 and 86, the apparatus here comprises a base 1010 having a first surface 1012, including a central portion 1012*a* and a peripheral portion 1012*b* circumscribing central portion 1012*a*. Peripheral portion 1012*b* includes a concave surface 1013*a* which defined a generally toroidal-shaped expansion channel or groove 1013 formed within base 1010. As before, base 1010 is also provided with a second surface 1014 to which an adhesive pad assembly 1016 is affixed. After a peal strip is removed from the pad assembly to expose a thin adhesive layer "A", the device can be conveniently affixed to the patient's body. Formed within base 1010 is a bore 1020 (FIG. 83), which receives a portion of the infusion means, or hollow cannula 1022, of the invention.

The apparatus shown in FIGS. 80 through 87 also includes a stored energy means for forming, in conjunction with the central portion of the base, the fluid reservoir 1002. Fluid reservoir 1002 has an inlet port 1026 and an outlet port 1030. Inlet port 1026 is in communication with an outlet port 1032*a* which is provided in an enlarged diameter portion 1022*a* of cannula 1022. Filling of fluid reservoir 1002 is accomplished via a septum assembly 1036 of the character previously described having a pierceable septum 1036*a* (FIG. 84). As before, a flow control means comprises the micro bore portion 1022*b* of the cannula. The flow control means in this latest embodiment of the invention also comprises a flow control member 1038, the character of which will presently be described.

The stored energy means is here provided in the form of a generally planar distendable membrane 1040 which overlays surface 1012 of the base. When the apparatus is assembled in the manner shown in FIG. 86, membrane 1040 spans central portion 1012*a* as well as the circumferentially extending channeled outer portion 1012*b* of base 1010. Membrane 1040 is sealably receivable within ring-like grooves 1043 and 1045 which are formed in cover 1005 (FIG. 83). Grooves 1043 and 1045 form a part of the sealing means of this embodiment of the invention as do inner and outer ring-like protuberances 1047 and 1049 formed on base 1010. As best seen by referring to FIG. 86, when base 1010 and cover 1005 are joined together, protuberance 1047 is closely received within groove 1043 and protuberance 1049 is closely received within groove 1045 in a manner to sealably clamp inner and outer ring-like portions 1040*a* and 1040*b* of distendable membrane 1040 between base 1010 and cover 1005.

Disposed within a generally circular shaped recess 1054 formed in base 1010 is a barrier means or separation membrane 1056 which prevents fluid within fluid reservoir 1002 from contacting distendable membrane 1040. Membrane 1056 can be formed from any suitable elastomeric material such as polyurethane, silicon or synthetic rubber.

With the construction shown in FIG. 86, the central or first conformable mass 1006 of the ullage defining means is disposed within chamber 1004 for engagement with membrane 1040 which, after being distended, will tend to return to its less distended configuration. As was the case with the previously discussed embodiment, the ullage defining means of this latest embodiment of the invention comprises not only the central conformable ullage 1006, but also the outer toroidal shaped, conformable ullage 1008. Both of the conformable masses 1006 and 1008 are uniquely covered by distendable membrane 1040 and both continuously vary in shape as the distendable membrane distends outwardly from the base (FIG. 86).

As before in this latest embodiment of the invention first conformable mass ullage 1006 communicates with the second outer toroidal-shaped mass 1008 via passageways 1061 which interconnect the first or central chamber 1004 formed in cover 1005 with the second toroidal-shaped chamber 1064 formed in cover 1005 (FIG. 83). As before, conformable masses 1006 and 1008 preferably comprise a deformable, flowable mass constructed from a suitable gel material. Accordingly, in a manner presently to be described, the gel which makes up first conformable mass 1006 can expand into chamber 1064 formed in cover 1005 via passageways 1061 as the distendable membrane 1040 distends outwardly during filling of fluid chamber 1002.

Turning particularly to FIGS. 81, 83 and 86, the generally straight cannula 1022 of the device includes the previously identified enlarged diameter portion 1022*a* and the microbore portion 1022*b* which terminates in an outboard extremity 1022*c* which is suitably interconnected with a luer connector 1065. In this latest form of the invention, the cannula is molded in place within bore 1020.

Turning particularly to FIG. 83, it can be seen that, as before, cover 1005 is provided with an upstanding protuberance 1067 which permits joining of the cover 1005 to the base 1010 by a sonic welding technique of the character previously described. Prior to joining the cover and the base and, prior to positioning the distendable membrane over the cover, chambers 1004 and 1064 are filled with gel. Also barrier membrane 1056 is, at this time, appropriately bonded to the base by adhesive bonding or like techniques well known to those skilled in the art. When the cover and base are sealably joined together, the ring-like protuberances 1047 and 1049 are guided into grooves 1043 and 1045 respectively so as to sealably clamp distendable membrane 1040 securely between the base and the cover. If desired, a suitable adhesive can be placed within grooves 1043 and 1045 to bond portions 1040*a* and 1040*b* of the distendable membrane to the cover to enhance sealing. After the cover and base have been interconnected, conformable ullages 1006 and 1008 are sealably captured between distendable membrane 1040 and the inner surfaces of cover 1005 which define chambers 1004 and 1064. It is to be noted that chambers 1004 and 1064 can also be filled with gel via a fill port 1005*f* and a passageway 1005*p* (FIG. 86)

Following the interconnection of base 1010 with cover 1005 in the manner described in the preceding paragraphs, fluid reservoir 1002 can be filled via septum assembly 1036 using a suitable syringe assembly containing the beneficial agent to be delivered to the patient. As the fluid chamber fills, conformable mass 1006 will conform to the central portion of the distendable membrane in the manner shown in FIG. 86 causing the gel which comprises mass 1006 to be forced inwardly and to overflow into the second toroidal-shaped chamber 1064 via passageways 1061. As the gel flows under pressure into chamber 1064, the outer peripheral portion of the distendable membrane 1040 will deform toward concave surface 1013*a* and into base channel 1013 permitting this channel to, at least, partially fill with gel. As the peripheral portion of the distendable membrane distends into channel 1013, any gases contained therein will be vented to atmosphere via vent means which here comprises a passageway 1069 and a vent plug 1071 (see FIGS. 80 and 82).

During the fluid expelling step, the gel can, of course, flow in the opposite direction from toroidal-shaped chamber 1064 into first or central chamber 1004 so as to conform to distendable membrane 1040 as it tends to return toward its less distended configuration.

With chambers 1004 and 1064 filled with gel, with fluid reservoir 1002 filled with the selected beneficial agent to be delivered to the patient and with the luer connector 1065 connected to a valved administration line, the device can be safely stored until time of use. At time of use, the administration line can be opened to fluid flow toward the patient.

Turning to FIG. 85 a slightly different form of cannula and septum is there illustrated. Here the fill end of cannula 1023 is bell shaped to sealably receive a matching shaped septum 1037*a*. This alternate design is better suited for certain end applications of the device.

Referring now to FIGS. 88 through 94, still another form of the ultra low profile infusion device of the invention is there shown and generally designated by the numeral 1100. This latest embodiment of the invention is similar in many respects to the embodiment shown in FIGS. 80 through 87 and like numbers are used to identify like components. This latest embodiment of the invention comprises a single fluid reservoir 1102 (FIG. 93) disposed within a first central chamber 1004 formed in a cover 1005 which is identical to that previously described in connection with the embodiment of FIGS. 80 through 87 and includes conformable masses 1006 and 1008 of the character previously described which are in communication via passageways 1061.

As best seen in FIGS. 91 and 93, base 1106 of this embodiment is of a slightly different construction having a central, generally convex surface 1106a and a peripheral portion 1106b which includes a concave surface which defines a generally toroidal-shaped expansion channel or groove 1110 formed within base 1106. In this latest form of the invention, convex portion 1106a, in cooperation with the conformable masses 1006 and 1008, comprise the ullage means of the invention. As before, base 1106 has a surface 1106c to which an adhesive pad assembly 1016 is affixed. Integrally molded within base 1106 is a hollow cannula 1114, which comprises a part of the infusion means of this form of the invention.

The apparatus shown in FIGS. 88 through 94 includes a uniquely configured stored energy means identical to that described in connection with the embodiment shown in FIGS. 80 through 87 and forms, in conjunction with the central portion 1106a of the base, the fluid reservoir 1102. Fluid reservoir 1102 has an inlet port 1116 and an outlet port 1120. Inlet port 1116 is in communication with an outlet port 1114a which is provided in an enlarged diameter portion 1114b of cannula 1114. Filling of fluid reservoir 1102 is accomplished via a septum assembly 1036 of the character previously described having a septum 1036a.

In this latest form of the invention, flow control means comprises both a uniquely shaped hydrogel rate control device 1118 as well as the micro bore portion 1114c of the cannula. Rate control device 1118 is held in place within a recess 1121 formed in base 1106 by any suitable means such as adhesive bonding. In use, the hydrogel rate control device swells upon imbibing fluid and functions to precisely control the rate of fluid flow from reservoir 1102.

As in the earlier described form of the invention, the stored energy means or membrane 1040, overlays the base and is sealably interconnected with cover 1005 in the same manner as described in connection with the form of the invention shown in FIGS. 80 through 87. When the apparatus is assembled in the manner shown in FIG. 93, membrane 1040 spans the central portion of the base as well as the circumferentially extending channeled outer portion 1106b. Inner and outer ring-like protuberances 1123 and 1125 are sealably receivable within ring-like grooves 1043 and 1045 which are formed in cover 1005 (FIG. 91) and which comprise a part of the sealing means of the invention.

In the construction shown in FIG. 94, the central convex portion 1106a of the base forms the rigid ullage portion of the ullage means and ullage portions 1006 and 1008 form the conformable ullage portions of the ullage means. As before, the conformable ullage portions of the ullage means are covered by distendable membrane 1040 and both continuously vary in shape as the distendable membrane distends outwardly from the base as fluid is introduced into reservoir 1102 via the septum assembly. Once again, central conformable ullage 1006 communicates with the outer toroidal ullage 1008 via passageways 1061 so that, as fluid chamber 1102 is filled, the gel which makes up the central ullage is engaged by a barrier membrane 1128 which is disposed between distendable membrane 1040 and cover 1005. With this construction, as reservoir 1102 fills membranes 1040, 1127, and 1128 will distend outwardly in the manner shown in FIG. 93 causing gel 1006 to flow into chamber 1064 of cover 1005. This causes the gel contained within this chamber to, in turn, expand, along with the membrane 1040 into channel 1110 formed in base 1106 in the manner shown in FIG. 93.

As before, in FIG. 89, cannula 1114 includes the previously identified enlarged diameter portion 1114b and the microbore portion 1114c which terminates in an extremity 1114d which communicates with a novel delivery luer assembly 1131, the character of which will presently be described.

Prior to joining the cover and the base as by sonic welding and, prior to positioning the distendable membrane 1040 and the containment film 1128 over the cover, chambers 1004 and 1064 are filled with the conformable mass or gel. Containment film 1128 can be constructed from various materials such as cellulose acetate, polyethylene, polypropylene polyvinyl films and the like and functions to contain the mass or gel within the cover. Also, rate control device 1118 is, at this time, emplaced into cavity 1121 and a first barrier membrane 1127 is affixed along its periphery to the central portion of base 1106. When the cover and base are sealably joined together, the ring-like protuberances 1123 and 1125 formed on base 1106 are guided into sealable engagement with grooves 1043 and 1045 respectively so as to sealably clamp both distendable membrane 1040 and film 1128 between the base and the cover. If desired, a suitable adhesive can be placed within grooves 1043 and 1045 to bond to the two membranes and to the cover to enhance sealing. After the cover and base have been thusly interconnected, conformable ullages 1006 and 1008 are sealably captured between containment film 1128 and the inner surfaces of cover 1005 which define chambers 1004 and 1064.

Following the interconnection of base 1106 with cover 1005 in the manner described in the preceding paragraphs, fluid reservoir 1102 can be filled via septum assembly 1036 using a suitable syringe assembly containing the beneficial agent to be delivered to the patient. Filter means, shown here as a porous filter member 1135, filters the fluid flowing out of outlet 1114a. Filter 1135 can be constructed from any suitable filter material such as a polycarbonate and is backed by a fluid blocking means shown here as a blocking membrane 1135a. Blocking membrane 1135a functions to direct the fluid flowing into cannula portion 1114b toward fluid reservoir 1102. As the fluid chamber fills, the peripheral portions of the distendable membrane 1040 and the barrier membrane 1128 will distend into channel 1110, and any gases contained therein will be vented to atmosphere via passageway 1006a and vent plug 1071 (see FIG. 88). During the fluid expelling step, the gel can, of course, flow in the opposite direction from toroidal chamber 1064 into central chamber 1004 so as to conform to barrier membrane 1128 as it tends, along with the distendable membrane, to return toward their less distended configuration.

Turning particularly to FIG. 92 the novel dispensing means of the form of the invention is there illustrated. This dispensing means includes the previously identified quick connect delivery fitting 1131 having a tapered inboard end 1131a which is telescopically and sealably receivable within a tapered bore 1142 formed in base 1106 (FIG. 91). In order to releasably lock fitting 1131 in position within bore 1142 and in fluid communication with end 1114d of cannula 1114, locking means shown here as resiliently deformable locking tabs 1144 are provided on base 1106. Extending from the end of quick connect fitting assembly 1131 is an infusion set 1146 having a soft cannula assembly 1150, the operation of which is well understood by those skilled in the art. Once the soft cannula 1150a has been introduced into the patients subdermal tissues "ST" in the manner shown in FIG. 92, the cannula insertion assembly 1152, which includes a trocar 1152a, can be removed leaving the soft cannula 1150a in position within the patient. Needle cannula interconnect 1154a of the connector assembly 1154 of the infusion set 1146 can then be inserted into assembly 1150 and interconnected therewith using the latch mechanism 1155. Connector assembly 1154 which forms a part of infusion set 1146, when connected with assembly 1150, places soft cannula 1150a in a fluid communication with reservoir 1102. Infusion set 1146 is of a character well known in the art and is readily available from several commercial sources including Pharma-Plast International A/S of Lynge, Denmark. By pushing inwardly on locking tabs 1144, delivery quick connect 1131 can be urged into bore 1142 to a position wherein locking tabs 1144 will close about member 1131 and in engagement with a shoulder 1131b formed on member 1131 so as to securely lock the dispensing means to the base.

In each of the embodiments of the invention described in the foregoing paragraphs which include ullage defining means, this means can be constructed not only from the previously described materials, but also from oils, such as mineral oil, corn oil, peanut oil, silicon oil, and cottonseed oil. Additionally, the ullage defining means can be constructed from materials such as sodium palmitate and sodium stearate, water, glycerine, air and methyl cellulose.

Similarly, in each of the embodiments of the invention as previously described which include barrier membranes, the barrier membranes can be formed from materials such as polyurethane, fluorosilicone, polypropylene, polyethylene and copolymers of these materials. A material particularly well suited for use in constructing the barrier membrane is a copolymer of polyethylene and polypropylene sold by Shell Oil Company under the name and style "Krayton".

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A device for use in infusing medicinal fluid into a patient at a controlled rate comprising:
   (a) a base having an upper surface including a central portion and a peripheral portion circumscribing said central portion, a lower surface and a channel formed in said base, said channel having non-linear shaped portions and first and second ends;
   (b) stored energy means for forming in conjunction with said base, a generally toroidal-shaped reservoir having an outlet, said stored energy means comprising at least one distendable membrane superimposed over said base, said membrane being distendable as a result of pressure imparted by fluids introduced into said reservoir to establish internal stresses, said stresses tending to move said membrane toward a less distended configuration;
   (c) ullage defining means disposed within said reservoir for engagement by said distendable membrane, said ullage defining means comprising a yieldable mass that is substantially conformable to the shape of said distendable membrane as said membrane tends to move toward a less distended configuration; and
   (d) infusion means for infusing medicinal fluid from said fluid reservoir into the patient, said infusion means having an inlet end disposed proximate said channel and including a hollow cannula having:
      (i) a central body portion disposed within said channel; and
      (ii) an outlet end portion including a portion extending substantially perpendicularly outward substantially from said lower surface of said base for insertion into the patient.

2. A device as defined in claim 1 further including fluid flow control means disposed between said reservoir and said inlet end of said infusion means.

3. A device as defined in claim 1 further including a cover affixed to said base, said cover having a concave surface formed therein for receiving said ullage means.

4. A device as defined in claim 1 further including fluid inlet means for introducing fluid into said fluid reservoir, said fluid inlet means comprising a pierceable septum mounted in said base.

5. A device as defined in claim 4 in which said hollow cannula includes an inlet portion for receiving a portion of said pierceable septum.

6. A device as defined in claim 4 further including a protective sheath removably connected to said base for surrounding and protecting said pierceable portion of said hollow cannula.

7. A device as defined in claim 6 further including a cannula closure telescopically receivable within said protective sheath, said closure having a central bore for receiving said pierceable portion of said hollow cannula.

* * * * *